United States Patent [19]
Vermeer

[11] Patent Number: 5,880,076
[45] Date of Patent: Mar. 9, 1999

[54] COMPOSITIONS COMPRISING GLYCACARBAMATE AND GLYCAUREA COMPOUNDS

[75] Inventor: Robert Vermeer, Nutley, N.J.

[73] Assignee: Lever Brothers Company, Division of Conopco, Inc., New York, N.Y.

[21] Appl. No.: 905,583

[22] Filed: Aug. 4, 1997

[51] Int. Cl.⁶ ............................... C11D 1/02; C11D 1/94; C11D 3/26

[52] U.S. Cl. .................. 510/123; 510/119; 510/126; 510/128; 510/130; 510/136; 510/137; 510/138; 510/141; 510/155; 510/156; 510/158; 510/159; 510/433; 510/501; 560/160

[58] Field of Search ....................... 510/119, 123, 510/126, 128, 130, 136, 137, 138, 141, 155, 156, 158, 159, 433, 501; 560/160

[56] References Cited

U.S. PATENT DOCUMENTS 5,354,510  10/1994  Vanlerberghe et al. ................. 252/548

FOREIGN PATENT DOCUMENTS 056458  7/1982  European Pat. Off. .
666251  8/1995  European Pat. Off. .

*Primary Examiner*—Paul Lieberman
*Assistant Examiner*—Gregory R. Delcotto
*Attorney, Agent, or Firm*—Ronald A. Koatz

[57] ABSTRACT

Novel personal product and detergent compositions comprising new and known glycacarbamate, glycaurea compounds or mixtures thereof are disclosed. The personal product compositions exhibit mild cleansing, opacifying/pearlescent and suspending action. The liquid detergent compositions exhibit enhanced viscosity and improved detergency. The powdered detergent compositions exhibit improved flow characteristics and improved detergency. Also, disclosed are novel glycacarbamate and glycaurea compounds which have enhanced water solubility and do not become turbid or produce sedimentation in aqueous compositions as well as an improved method of manufacture.

18 Claims, No Drawings

COMPOSITIONS COMPRISING GLYCACARBAMATE AND GLYCAUREA COMPOUNDS

FIELD OF THE INVENTION

The present invention relates to novel personal product and detergent compositions comprising new and known glycacarbamate and glycaurea compounds. In particular, the invention relates to glycacarbamate and glycaurea compounds which are useful as mild cleansing, opacifying/pearlescent or suspending agents for personal product compositions; as viscosity modifying, gelling or thickening agents for liquid detergent compositions and as process flow aids for powdered detergent compositions. Furthermore, the detergent compositions of the present invention also exhibit improved cleaning and detergency on oily soils and stains.

The present invention also relates to certain novel glycacarbamate and glycaurea compounds which have enhanced water solubility and do not become turbid or produce sedimentation in aqueous personal product and detergent compositions as well as an improved method of manufacture of new and known glycacarbamate and glycaurea compounds.

BACKGROUND OF THE INVENTION

The demand for mild, biodegradable, environmentally friendly ingredients has been steadily rising. In general, most ingredients are based on, or derived from petrochemicals. Since these materials can sometimes have handling, storage and environmental hazards associated with them, it would be most desirable to use ingredients which are instead derived from agriculturally grown materials, such as carbohydrates. These naturally occurring compounds represent a source of renewable raw materials that are synthetically versatile, readily available, inexpensive, biodegradable, aquatically favorable and optically pure. In addition, it is most desirable to have ingredients that provide mild cleansing, opacifying/pearlescent and suspending action in personal product compositions, as well as provide improved viscosity (thickening) and flow for detergent compositions. Furthermore, it is most desirable to have ingredients that provide improved cleaning and detergency on oily soils and stains. This has been a difficult challenge to meet and it is not surprising to find considerable resource and effort have been directed towards the discovery and development of new ingredients that provide improved benefits in personal product and detergent compositions. The patent literature, cosmetic journals and formularies describe many such ingredients, however, they still do not provide all the answers to the problems encountered in making a totally satisfactory personal product and detergent composition.

It has now been found that novel personal product and detergent compositions comprising glycacarbamate and glycaurea compounds can be effectively formulated. For example, the personal product compositions of the present invention exhibit mild cleansing while simultaneously providing a soft, silvery and pearly luster which often has very favorable consumer appeal. Also, the personal product compositions of the present invention exhibit uniform suspending action of certain performance ingredients (e.g. zinc pyridinethione, silicone fluid etc.) thereby assisting with the delivery of the desirable performance attributes associated with these ingredients. Furthermore, the liquid detergent compositions of the present invention exhibit improved viscosity (thickening) and the powdered detergent compositions of the present invention exhibit improved flow or handling characteristics particularly in the presence of certain hygroscopic performance ingredients (e.g. 2,2'-oxydisuccinate, sulfocarboxymethylsuccinate, etc) while simultaneously providing excellent oily soil and stain removal.

In addition, it has also been found that certain novel glycacarbamate and glycaurea compounds of the invention which contain a disaccharide head group or oxygen heteroatom, exhibit enhanced solubility in water as well as in aqueous personal product and detergent compositions.

Furthermore, an improved method of manufacture of new and known glycacarbamate and glycaurea compounds has been also found wherein said compounds are prepared in good yield, high purity and desirable color without hydroxyl group protection, oligomerization or polymerization.

The glycacarbamate and glycaurea compounds of the present invention represent a naturally derived, cost-effective, biodegradable class of nonionic surfactant compound which has properties equal to, or better than other well known petrochemically derived ingredients, thereby indicating that they are viable, environmentally sound alternatives to traditional petrochemical ingredients.

These findings are quite unexpected and have not been recognized or appreciated in the art.

BACKGROUND ART

Some glycacarbamate and glycaurea compounds are known in the art. For Example, U.S. Pat. No. 2,834,775 to Boettner (1958) disclose N-alkyl-N-sorbitylcarbamic acid and N-alkyl-N-sorbitylurea compounds of the general formulas:

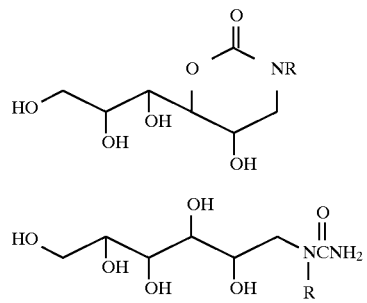

wherein R is a C1–C18 straight chain or branched chain alkyl group. The N-alkyl-N-sorbitylurea compounds are said to have application in the paper industry as rewetting agents and the N-alkyl-N-sorbitylcarbamic acid compounds are said to be useful as depressants of water surface tension, foam stabilizers, detergents and antibacterial/fungicidal agents. There is no teaching or suggestion of using such compounds as mild cleansing, opacifying/pearlescent and suspending agents for personal product compositions. Also, there is no teaching or suggestion of using such compounds as viscosity modifying, gelling and thickening agents for liquid detergent compositions or as process flow aids for powdered detergent compositions. Furthermore, there is no teaching or suggestion of using a di-, tri- or polysaccharide head group, or a heteroatom for enhanced solubility in water and aqueous personal product and detergent compositions as well as the improved method of manufacture of new and known glycacarbamate and glycaurea compounds.

U.S. Pat. No. 2,922,784 to Boettner (1960) disclose N-alkyl-N-sorbitylurea compounds of the general formula:

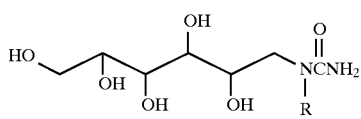

wherein R is a $C_1$–$C_{18}$ straight chain or branched chain alkyl group. The compounds are said to have application in the paper industry as rewetting agents and enhance the water absorptivity onto paper towels. There is no teaching or suggestion of using such compounds as mild cleansing, opacifying/pearlescent and suspending agents for personal product compositions. Also, there is no teaching or suggestion of using such compounds as viscosity modifying, gelling and thickening agents for liquid detergent compositions or as process flow aids for powdered detergent compositions. Furthermore, there is no teaching or suggestion of using a di-, tri- or polysaccharide head group, or a heteroatom for enhanced solubility in water and aqueous personal product and detergent compositions as well as the improved method of manufacture of new and known glycacarbamate and glycaurea compounds.

DE Application 3,904,247 and EP Application 0,383,024 to Schneider et al. (1990) disclose N-polyhydroxy-N'-alkylurea compounds of the formulas:

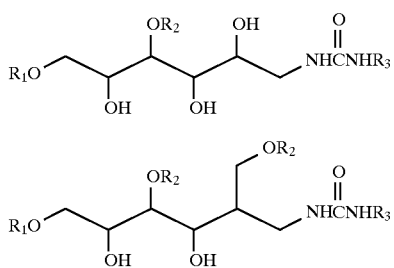

wherein $R_1$ and $R_2$ are hydrogen or a mono- or oligosaccharide, $R_3$ is a $C_4$–$C_{21}$ alkyl group. The compounds are said to be useful as surface-active agents, emulsifying agents or as humectants in cosmetic formulations. They are also said to be used for detergent purposes and as auxiliaries in the food and pharmaceutical industries. The compounds of DE Application 3,904,247 and EP Application 0,383,024 are prepared by the reaction of glycamine with alkyl isocyanate, whereas the compounds of the present invention are prepared by the reaction of glycamine with urea, alkylurea or potassium cyanate. The net result is a structurally different glycaurea compound from DE Application 3,904,247 and EP Application 0,383,024.

U.S. Pat. Nos. 5,560,872 and 5,562,865 to Rahman et al. (1994) disclose personal product and detergent compositions comprising oxazolidine and tetrahydrooxazine amide surfactants as well as methods for their manufacture. The compounds are of the general formulas:

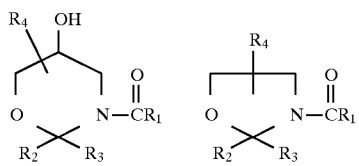

wherein $R_1$ is a linear or branched, saturated or unsaturated hydrocarbon having 1 to 50 carbons and may be interrupted with heteroatoms such as oxygen, sulfur or nitrogen; $R_2$ and $R_3$ are hydrogen or a linear or branched, saturated or unsaturated hydrocarbon group having 1 to 50 carbons; and $R_4$ is selected from the group consisting of —(CHOH)$_n$CH$_2$OH, where n is an integer from 1 to 5. The compounds of U.S. Ser. Nos. 08/444,333 and 08/444,335 are structurally different from the compounds of the present invention.

Carbohydrate Research 210, 155 (1991) to Kovacs et al. discloses the preparation of glycosylamine 1,2-(cyclic carbamates) also generally known as glycofurano/pyrano [1,2-d] oxazolid-2-ones of the general formulas:

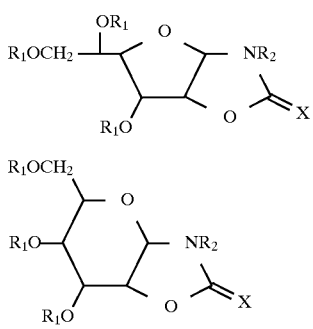

wherein $R_1$ and $R_2$ are hydrogen (H) or an acetyl group and X is a sulfur (S) or oxygen (O) atom. The compounds are prepared by the treatment of certain pentoses and hexoses with potassium cyanate in aqueous solutions, buffered with sodium dihydrogen phophate or ammonium chloride. The net result is a set of compounds containing a cyclic sugar head group that are structurally different from the compounds of the present invention. Similar cyclic sugar head group containing compounds are taught in Bull. Chem. Soc. Jpn. 54, 1834 (1981) to Takagi et al., J. Antibiot. 31, 394 (1978) to Tresner et al., Cabohydr. Res. 141, 57 (1985), 166, 101 (1987) to Kovacs et al., Chem Ber. 100, 845 (1967) to Jochims et al., Cabohydr. Res. 198, 358 (1990) to Kovacs et al., Cabohydr. Res. 163, 132 (1987) to Galbis Perez et al., Cabohydr. Res. 2, 439 (1983) to Benzing-Purdie et al., Acta Crystallogr., Sec B 32, 2329 (1976) to Singh et al., Tetrahedron 31, 1873 (1975) to Meresz et al., Adv. Carbohydr. Chem. Biochem. 41, 27 (1983) to Bock et al., Tetrahedron Letters 25 (18), 1901 (1984) to Plusquellec et al., Tetrahedron 46(2), 465 (1990) to Plusquellec et al. and U.S. Pat. No. 3,086,010 to Matthaeus.

Thus the ability to find and effectively formulate several naturally derived, environmentally friendly, new and known glycacarbamate and glycaurea compounds in personal product and detergent compositions is a significant achievement.

Accordingly, it is an object of the present invention to provide several novel personal product and detergent compositions comprising glycacarbamate and glycaurea compounds.

It is another object of the present invention to provide novel personal product compositions that exhibit mild cleansing.

It is another object of the present invention to provide novel personal product compositions that exhibit a soft, silvery and pearly luster.

It is another object of the present invention to provide novel personal product compositions that exhibit effective suspending action of performance ingredients for improved delivery of desirable performance attributes.

It is still another object of the present invention to provide novel liquid detergent compositions that exhibit improved viscosity and thickness.

It is still another object of the present invention to provide novel powdered detergent compositions that exhibit improved flow and handling characteristics.

It is still another object of the present invention to provide novel detergent compositions that exhibit improved detergency and performance on oily soil.

It is still another object of the present invention to provide several novel naturally derived, cost-effective, biodegradable glycacarbamate and glycaurea compounds that are useful as surfactants.

It is still another object of the present invention to provide an improved class of glycacarbamate and glycaurea compound that exhibits enhanced water solubility.

It is still another object of the present invention to provide an improved class of glycacarbamate and glycaurea compound that does not become turbid or produce sedimentation upon standing in aqueous personal product and detergent compositions.

It is still another object of the present invention to provide an improved class of glycacarbamate and glycaurea compound that is prepared in good yield, high purity and desirable color without hydroxyl group protection, oligomerization or polymerization.

It is a final object of the present invention to provide improved method of manufacture of new and known glycacarbamate and glycaurea compounds.

These and other objects will become readily apparent from the detailed description that follows.

SUMMARY OF THE INVENTION

The present invention relates to novel personal product and detergent compositions comprising new and known glycacarbamate and glycaurea compounds. In particular, the invention relates to glycacarbamate and glycaurea compounds which are useful as mild cleansing, opacifying/pearlescent or suspending agents for personal product compositions; as viscosity modifying, gelling or thickening agents for liquid detergent compositions; and as process flow aids for powdered detergent compositions. Furthermore, the detergent compositions of the present invention also exhibit improved cleaning and detergency on oily soils and stains.

The present invention also relates to certain novel glycacarbamate and glycaurea compounds which have enhanced water solubility and do not become turbid or produce sedimentation in aqueous personal product and detergent compositions as well as an improved method of manufacture of new and known glycacarbamate and glycaurea compounds.

The glycacarbamate (a) and glycaurea (b) compounds of the present invention are most generally defined by the formulas:

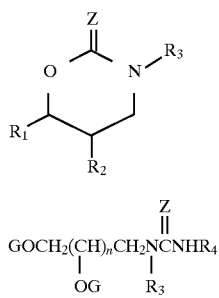

wherein:
$R_1$ is $GOCH_2(CHOG)_n$-, $GOCH_2(CHOH)_n(CHOG)$- or $GOCH_2(CHOG)_{n-1}(CH_2OG)CH—$;
$R_2$ is GO— or $GOCH_2$—;
Z is sulfur (S) or oxygen (O);

G is hydrogen, $SO_3M$, $PO_3M_2$, mono-, di-, oligo-, polysaccharide, $(CH_2CH_2O)_q$—H, $(CH_2CHCH_3O)_r$—H group or mixtures thereof;

M is hydrogen, an alkali metal, alkaline earth metal, ammonium, substituted alkyl ammonium group, or mono-, di-, trialkanolammonium group comprising 1 to 3 carbon atoms.

n is an interger from 0 to 6;

q and r are intergers from 1 to 50;

$R_3$, $R_4$ and $R_5$ are the same or different and can be hydrogen, a straight or branched chain, saturated or unsaturated hydrocarbon radical with may be unsubstituted or substituted with an aromatic, cycloaliphatic or mixed aromatic aliphatic group comprising from 1 to 35 carbon atoms. $R_3$ and $R_4$ can also be selected from the group consisting of;

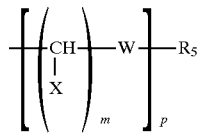

X is hydrogen, a saturated hydrocarbon radical comprising 1 to 4 carbon atoms or mixtures thereof;

W is an amine (NH or NA), amine salt (NHA+M−), urea (NHCONHA), ether (O), ester (COO or OOC), hydroxyl (CHOH or HOCOH), sulfur (S), sulfur monoxide (SO), sulfur dioxide ($SO_2$), amide (NACO, CONA or NCOA) or mixtures thereof;

m is an interger from 1 to 6;

p is an interger from 0 to 50;

A is the same as $R_3$ and $R_4$.

DETAILED DESCRIPTION OF THE INVENTION

The present invention relates to novel personal product and detergent compositions comprising new and known glycacarbamate and glycaurea compounds. In particular, the first embodiment of the invention relates to glycacarbamate and glycaurea compounds which are useful as mild cleansing, opacifying/pearlescent or suspending agents for personal product compositions.

The second embodiment of the invention relates to glycacarbamate and glycaurea compounds which are useful as viscosity modifying, gelling or thickening agents for liquid detergent compositions.

The third embodiment of the invention relates to glycacarbamate and glycaurea compounds which are useful as process flow aids for powdered detergent compositions.

The forth embodiment of the invention relates to detergent compositions comprising glycacarbamate and glycaurea compounds that have improved detergency on oily soils and stains.

The fifth embodiment of the invention relates to certain novel glycacarbamate and glycaurea compounds which have enhanced water solubility and do not become turbid or produce sedimentation in aqueous personal product and detergent compositions.

The sixth embodiment of the present invention relates to an improved method of manufacture of new and known glycacarbamate and glycaurea compounds.

A glycacarbamate compound is defined as a 1,3-cyclic carbamate or glycaoxolidin-2-one of an glycamine or alkylglycamine, which in turn, is defined as a sugar substance in which the pseudoaldehyde or pseudoketose group, generally found at the $C_1$ or $C_2$ position of the sugar, has been reduced to an amino group or alkylamino group through a reductive amination reaction with ammonia or alkylamine and hydrogen in the presence of a metal catalyst such as nickel. The reaction is typically done in water or organic solvent, but is usually done in a mixture of both.

A glycaurea compound is defined as a urea of an glycamine or alkylglycamine, which in turn, is defined as a sugar substance in which the pseudoaldehyde or pseudoketose group, generally found at the $C_1$ or $C_2$ position of the sugar, has been reduced to an amino group or alkylamino group through a reductive amination reaction with ammonia or alkylamine and hydrogen in the presence of a metal catalyst such as nickel. The reaction is typically done in water or organic solvent, but is usually done in a mixture of both. Methods of preparing such glycamines are well known in the art and are described in the J. Chem. Soc. 1682, (1922) to Ling et al.; J. Amer. Chem. Soc. 62, 3315, (1940) to Wayne et al., 72, 5416, (1950) to Holly et al., 79, 3541, (1957) to Kagan et al.; Methods in Carbohydr. Chem. 2, 79, (1963) to Long et al.; U.S. Pat. No. 2,016,962 to Flint et al., U.S. Pat. No. 2,621,175 to Holly et al.; and EP Application No. 0,536,939 to Beck, U.S. Pat. No. 5,334,764 to Scheibel et al., U.S. Pat. No. 2,016,962 to Flint et al., J. Amer. Chem. Soc. 66, 483 (1944) and J. Dispersion Science and Technology 12 (3&4), 227, (1991) all of which are incorporated herein by reference.

A glycacarbamate may be based on carbohydrates comprising one saccharide unit [e.g., glucocarbamates (sorbitylcarbamates)or fructocarbamates], two saccharide units [e.g., lactocarbamates], three saccharide units [e.g., maltotriocarbamates] or they may be based on compounds comprising more than three saccharide units [e.g., maltoheptocarbamates]. It should be noted that any carbohydrate can be used as long as the sugar has an amino group or a pseudoaldehyde or pseudoketose group available for reduction to an amino group.

A glycaurea may be based on carbohydrates comprising one saccharide unit [e.g., glucoureas (sorbitylureas)or fructoureas], two saccharide units [e.g., lactoureas], three saccharide units [e.g., maltotrioureas] or they may be based on compounds comprising more than three saccharide units [e.g., maltoheptoureas]. It should be noted that any carbohydrate can be used as long as the sugar has an amino group or a pseudoaldehyde or pseudoketose group available for reduction to an amino group.

The glycacarbamate (a) and glycaurea (b) compounds of the present invention are most generally defined by the formulas:

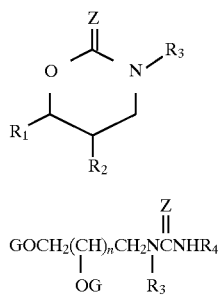

a $$GOCH_2(CH)_nCH_2NCNHR_4 \atop OG \quad R_3 \overset{Z}{\underset{\|}{}}$$

b wherein:
R$_1$ is GOCH$_2$(CHOG)$_n$-, GOCH$_2$(CHOH)$_n$(CHOG)- or GOCH$_2$(CHOG)$_{n-1}$(CH$_2$OG)CH—;

R$_2$ is GO— or GOCH$_2$—;
Z is sulfur (S) or oxygen (O);
G is hydrogen, SO$_3$M, PO$_3$M$_2$, mono-, di-, oligo-, polysaccharide, (CH$_2$CH$_2$O)$_q$—H, (CH$_2$CHCH$_3$O)$_r$—H group or mixtures thereof;
M is hydrogen, an alkali metal, alkaline earth metal, ammonium, substituted alkyl ammonium group, or mono-, di-, trialkanolammonium group comprising 1 to 3 carbon atoms.
n is an interger from 0 to 6;
q and r are intergers from 1 to 50;
R$_3$, R$_4$ and R$_5$ are the same or different and can be hydrogen, a straight or branched chain, saturated or unsaturated hydrocarbon radical with may be unsubstituted or substituted with an aromatic, cycloaliphatic or mixed aromatic aliphatic group comprising from 1 to 35 carbon atoms. R$_3$ and R$_4$ can also be selected from the group consisting of;

X is hydrogen, a saturated hydrocarbon radical comprising 1 to 4 carbon atoms or mixtures thereof;
W is an amine (NH or NA), amine salt (NHA+M−), urea (NHCONHA), ether (O), ester (COO or OOC), hydroxyl (CHOH or HOCOH), sulfur (S), sulfur monoxide (SO), sulfur dioxide (SO$_2$), amide (NACO, CONA or NCOA) or mixtures thereof;
m is an interger from 1 to 6;
p is an interger from 0 to 50;
A is the same as R$_3$ and R$_4$.

Preferably:
R$_1$ is GOCH$_2$(CHOG)$_n$—;
R$_2$ is GO—;
Z is oxygen (O);
G is hydrogen, SO$_3$M, PO$_3$M$_2$, monosaccharide, (CH$_2$CH$_2$O)$_q$—H, (CH$_2$CHCH$_3$O)$_r$—H group or mixtures thereof;
M is hydrogen, an alkali metal, alkaline earth metal, ammonium, substituted alkyl ammonium group, or mono-, di-, trialkanolammonium group comprising 1 to 3 carbon atoms.
n is an interger from 0 to 5;
q and r are intergers from 1 to 30;
R$_3$, R$_4$ and R$_5$ are the same or different and can be hydrogen, a straight or branched chain, saturated or unsaturated hydrocarbon radical comprising from 2 to 28 carbon atoms. R$_3$ and R$_4$ can also be selected from the group consisting of;

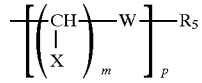

X is hydrogen, a saturated hydrocarbon radical comprising 1 to 3 carbon atoms or mixtures thereof;
W is an amine (NA), amine salt (NHA+M−), ether (O), hydroxyl (CHOH or HOCOH) or mixtures thereof;
m is an interger from 1 to 5;
p is an interger from 0 to 30;
A is a straight or branched chain, saturated or unsaturated hydrocarbon radical comprising from 1 to 28 carbon atoms.

Most preferably:

R$_1$ is GOCH$_2$(CHOG)$_n$—;

R$_2$ is GO—;

Z is oxygen (O);

G is hydrogen, monosaccharide, (CH$_2$CH$_2$O)$_q$—H, (CH$_2$CHCH$_3$O)$_r$—H group or mixtures thereof;

n is an interger from 0 to 4;

q and r are intergers from 1 to 15;

R$_3$ and R$_5$ are a straight or branched chain, saturated or unsaturated hydrocarbon radical comprising from 3 to 22 carbon atoms. R$_3$ can also be selected from the group consisting of;

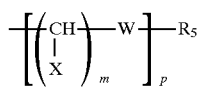

X is hydrogen, a saturated hydrocarbon radical comprising 1 to 2 carbon atoms or mixtures thereof;

W is ether (O);

m is an interger from 1 to 4;

p is an interger from 0 to 15;

R$_4$ is hydrogen.

A specific example of a known monosaccaharide glycacarbamate compound of the invention is N-octyl D-glucocarbamate (also known as N-octyl-N-sorbitylcarbamate) having the formula:

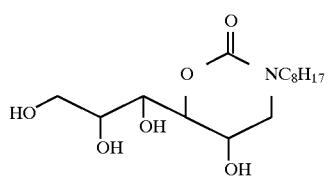

A specific example of a novel monosaccaharide glycacarbamate compound of the invention is N-coconut D-glucocarbamate having the formula:

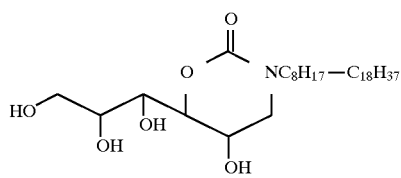

Another specific example of a novel monosaccaharide glycacarbamate compound of the invention is N-octyl/decyloxypropyl D-glucocarbamate having the formula:

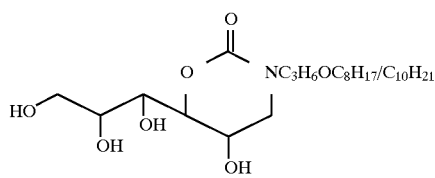

Another specific example of a novel monosaccaharide glycacarbamate compound of the invention is N-tetradecyl (pentaoxyethyl)oxypropyl D-glucocarbamate, also known as N-tetradecyl(pentaoxyethylene)oxypropyl D-glucocarbamate having the formula:

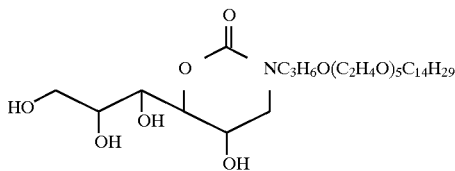

Yet another specific example of a novel monosaccaharide glycacarbamate compound of the invention is polyoxyethylene (6) N-dodecyl/tetradecyl D-glucocarbamate also known as N-dodecyl/tetradecyl D-glucocarbamate hexaoxyethylene ether having the formula:

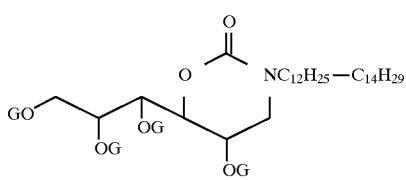

wherein G is an ethylene oxide residue (CH$_2$CH$_2$O)$_q$—H, and q can vary from about 1 to about 12 for a total average of 12.

A specific example of a novel disaccaharide glycacarbamate compound of the invention is N-dodecyl D-maltocarbamate having the formula:

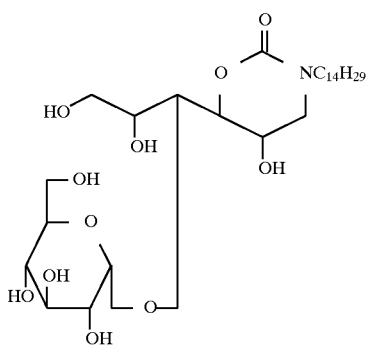

Another specific example of a novel disaccaharide glycacarbamate compound of the invention is N-coconut D-lactocarbamate having the formula:

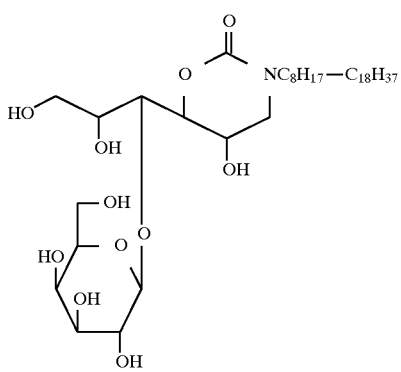

Yet another specific example of a novel disaccaharide glycacarbamate compound of the invention is N-dodecyl (trioxypropylene)oxypropyl D-glucopyranosyl-(1,5)-D-arabincarbamate having the formula:

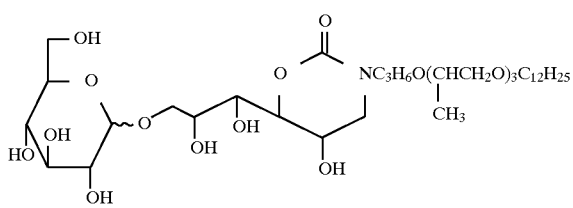

A specific example of a novel monosaccaharide glycaurea compound of the invention is N-coconut D-glucourea (also known as N-coconut-N-sorbitylurea) having the formula:

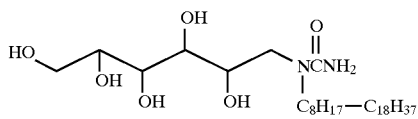

A specific example of a novel monosaccaharide glycaurea compound of the invention is N-dodecyloxypropyl D-glucourea having the formula:

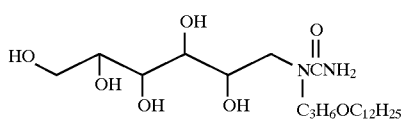

A specific example of a novel monosaccaharide glycaurea compound of the invention is N-dodecyl/pentadecylhepta (oxyethyl)oxypropyl D-glucourea having the formula:

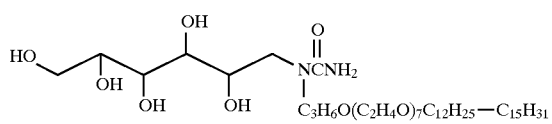

A specific example of a known monosaccaharide glycaurea compound of the invention is N-decyl D-glucourea having the formula:

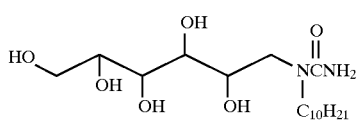

Other examples of other preferred novel compounds of the invention are set forth below:
 alkyloxymethyl D-glucocarbamate/urea
 alkyloxyethyl D-glucocarbamate/urea
 alkyloxybutyl D-glucocarbamate/urea
 alkyloxypentyl D-glucocarbamate/urea
 alkyloxyethyloxymethyl D-glucocarbamate/urea
 alkyldi(oxyethyl)oxymethyl D-glucocarbamate/urea
 alkyldi(oxyethyl) D-glucocarbamate/urea
 alkyltri(oxyethyl) D-glucocarbamate/urea
 alkyltetra(oxyethyl) D-glucocarbamate/urea
 alkylpenta(oxyethyl) D-glucocarbamatelurea
 alkylhexa(oxyethyl) D-glucocarbamate/urea
 alkylhepta(oxyethyl) D-glucocarbamate/urea
 alkylocta(oxyethyl) D-glucocarbamate/urea
 alkydi(oxypropyl)oxyethyl D-glucocarbamate/urea
 alkyltri(oxypropyl)oxyethyl D-glucocarbamate/urea
 alkylocta(oxypropyl)oxyethyl D-glucocarbamate/urea
 alkyldi(oxyethyl)oxypropyl D-glucocarbamate/urea
 alkyltri(oxyethyl)oxypropyl D-glucocarbamate/urea
 alkyltetra(oxyethyl)oxypropyl D-glucocarbamate/urea
 alkylpenta(oxyethyl)oxypropyl D-glucocarbamate/urea
 alkylhexa(oxyethyl)oxypropyl D-glucocarbamate/urea
 alkylhepta(oxyethyl)oxypropyl D-glucocarbamate/urea
 alkylocta(oxyethyl)oxypropyl D-glucocarbamate/urea
 alkyloxymethyl D-lactobionamide/urea
 alkyloxyethyl D-lactocarbamate/urea
 alkyloxybutyl D-lactocarbamate/urea
 alkyloxypentyl D-lactocarbamate/urea
 alkyl(oxyethyl)oxymethyl D-lactocarbamate/urea
 alkyldi(oxyethyl)oxymethyl D-lactocarbamate/urea
 alkyldi(oxyethyl) D-lactocarbamate/urea
 alkyltri(oxyethyl) D-lactocarbamate/urea
 alkyltetra(oxyethyl) D-lactocarbamate/urea
 alkylpenta(oxyethyl) D-lactocarbamate/urea
 alkylhexa(oxyethyl) D-lactocarbamate/urea
 alkylhepta(oxyethyl) D-lactocarbamate/urea
 alkylocta(oxyethyl) D-lactocarbamate/urea
 alkyldi(oxypropyl)oxyethyl D-lactocarbamate/urea
 alkyltri(oxypropyl)oxyethyl D-lactocarbamate/urea
 alkylocta(oxypropyi)oxyethyl D-lactocarbamate/urea
 alkyldi(oxyethyl)oxypropyl D-lactocarbamate/urea
 alkyltri(oxyethyl)oxypropyl D-lactocarbamate/urea
 alkyltetra(oxyethyl)oxypropyl D-lactocarbamate/urea
 alkylpenta(oxyethyl)oxypropyl D-lactocarbamate/urea
 alkylhexa(oxyethyl)oxypropyl D-lactocarbamate/urea
 alkylhepta(oxyethyl)oxypropyl D-lactocarbamate/urea
 alkylocta(oxyethyl)oxypropyl D-lactocarbamate/urea
 alkyloxyethyl D-maltocarbamate/urea
 alkyloxyethyloxymethyl D-maltocarbamate/urea
 alkylhexa(oxyethyl) D-maltocarbamate/urea
 alkyloxyethyl D-glucoheptocarbamate/urea
 alkyloxyethyl D-melicarbamate/urea
 alkyloxyethyl D-cellocarbamate/urea
 alkyloxyethyl D-gentiocarbamate/urea
 alkyloxyethyl D-glucopyranosyl-(1–5)-D-arabincarbamate/urea
 alkyloxypropyl D-gluconamide monooxyethylene ether
 alkyloxypropyl D-gluconamide dioxyethylene ether
 alkyloxypropyl D-glucocarbamate/urea trioxyethylene ether
 alkyloxypropyl D-glucocarbamate/urea tetraoxyethylene ether
 alkyloxypropyl D-glucocarbamate/urea pentaoxyethylene ether
 alkyloxypropyl D-glucocarbamate/urea hexaoxyethylene ether
 alkyloxypropyl D-glucocarbamate/urea heptaoxyethylene ether
 alkyloxypropyl D-glucocarbamate/urea octaoxyethylene ether
 alkyloxypropyl D-glucocarbamate/urea nonaoxyethylene ether
 alkyloxypropyl D-glucocarbamate/urea decaoxyethylene ether alkyloxypropyl D-giucocarbamate/urea trioxypropylene ether alkyloxypropyl D-glucocarbamate/urea oxyethylenedioxypropylene ether alkyloxyethyl D-glucocarbamate/urea dioxyethylenetrioxypropylene ether alkyloxyethyl D-glucocarbamate/urea trioxypropylenedioxyethylene ether alkyloxypropyl D-lactocarbamate/urea monooxyethylene ether alkyloxypropyl D-lactocarbamate/urea dioxyethylene ether alkyloxypropyl D-lactocarbamate/urea trioxyethylene ether alkyloxypropyl D-lactocarbamate/urea tetraoxyethylene ether alkyloxypropyl D-maltocarbamate/urea dioxyethylene ether alkyloxypropyl D-maltocarbamate/urea pentaoxypropylene ether alkyloxypropyl D-maltocarbamate/urea decaoxypropylene ether wherein the alkyl group contains from about 1 to about 35 carbon atoms, preferably from about 2 to about 28 carbon atoms and even more preferably from about 3 to about 22 carbon atoms.

It should noted that phrase "carbamate/urea" represents individual carbamate and urea compounds as well as mixtures thereof.

Suitable examples of the $R_3$, $R_4$ and A group, include but are not limited to $C_1$ to $C_{18}$ alkyl, coconut, soya, tallow, tall oil, castor, corn, cottonseed, palm, rapeseed, safflower, sesame, sunflower, fish oil, allyl, octenyl, nonenyl, decenyl, undecenyl, dodecenyl, tridecenyl, tetradecenyl, pentadecenyl, hexadecenyl, heptadecenyl, octadecenyl (oleyl), linoleyl and linolenyl.

If the $R_3$, $R_4$ and A group is interrupted by an aromatic radical, suitable examples include but are not limited to, benzyl and aniline. Cycloaliphatic radicals are exemplified but are not limited to, cyclopentyl and cyclohexyl. Suitable examples of mixed aromatic aliphatic radicals are exemplified but are not limited to, benzylpropyl, phenylethyl, phenoxyethyl vinylbenzyl and styrene.

The G group can be hydrogen, $SO_3M$, $PO_3M_2$, mono-, di-, oligo-, polysaccharide $(CH_2CH_2O)_qH$, $(CH_2CHCH_3O)_rH$ or mixtures thereof.

Examples of M include but are not limited to hydrogen, sodium, potassium, magnesium, lithium, calcium, ammonia, monoethanolamine, diethanolamine, triethanolamine, glucamine, methylglucamine, hydroxyethylglucamine, methylamine, diethylamine, triethylamine, glucosamine, 2-amino-2-hydroxymethyl-1,3-propanediol, 4-amino-4-(3-hydroxypropyl)-1,7-heptanediol, 2-amino-2-methyl-1,3-propanediol, 2-amino-2-methyl-1-propanol, 3-amino-1-propanol, sodium glycinate, potassium glycinate, sodium alaninate, sodium serinate, potassium leucinate, sodium asparticate, lithium valinate, sodium sarcosinate and the like.

Examples of suitable saccharides that can be reduced to a glycamine or alkylglycamine include aldotrioses, aldotetroses, aldopentoses, aldohexoses, 6-deoxyaldohexoses, aldoheptoses, ketotrioses, ketopentoses, ketohexoses, ketoheptoses, ketooctoses and ketononoses. Specific examples of saccharides that fall within the above classes include, but are not limited to glyceraldehyde, erythrose, threose, ribose, arabinose, xylose, lyxose, allose, altrose, glucose, mannose, gulose, idose, galactose, talose, 6-deoxyallose, 6-deoxyaltrose, 6-deoxyglucose, 6-deoxygulose, 6-deoxytalose, fucose, rahmnose, glycergalactoheptose, glycerglucoheptose, glycermanno-heptose, 1,3-dihydroxy-2-propanone, erythrulose, ribulose, xylulose, psicose, fructose, sorbose, tagatose, alloheptose, altro-3-heptulose, mannoheptulose, sedoheptulose, taloheptulose, glycerogalactooctulose, glycermannooctulose, erythrogalactononulose, erythroglucononulose, sucrose, lactose, maltose, isomaltose, isomalt, isomaltulose (palatinose), α,α-trehalose, cellobiose, gentiobiose, laminarabiose, xylobiose, inulobiose, mannobiose, chondrosine, 3-ketosucrose, leucrose, lactulose, melibiose, turnanose, trehalose, raffinose, planteose, melezitose, gentianose, maltotriose, cellotriose, panose, starchyose, verbascose, cyclohexaamylose, maltoheptanose, cellodextrin, amylose, amylodextrin, dextran, high dextrose corn syrup, high fructose corn syrup, high maltose corn syrup, xylans, mannans, starch, hemicellulose and cellulose. The saccharide may be acyclic or cyclic (including furanose, pyranose, septanose rings or mixtures thereof), have the D or L configuration and contain a α or β hydroxyl group or mixtures thereof at the anomeric position.

When an amino group is present in the alkyl chain it may be converted to the corresponding salt by reaction with, for example an organic or inorganic acid such as hydrochloric acid, sulfuric acid, phosphoric acid, boric acid, oxalic acid, malonic acid, glutaric acid, adipic acid, sebacic acid, tricarballylic acid, butanetetracarboxylic acid, itaconic acid, maleic acid, malic acid, fumaric acid, citraconic acid, glutaconic acid, bis(hydroxymethyl)propionic acid, tartaric acid, citric acid, formic acid, lactic acid, acetic acid, benzoic acid, methanesulfonic acid, ethanesulfonic acid, toluenesulfonic acid and mixtures thereof or quaternization with, for example an alkylating agent such as chloromethane, dimethyl sulfate, diethyl sulfate and benzyl chloride.

The glycacarbamate and glycaurea compounds of the present invention can also be ethoxylated, propoxylated or butoxylated with ethylene oxide, propylene oxide, butylene oxide or mixtures thereof to give a series of novel nonionic polyoxyalkylene ether sugar surfactants.

The glycacarbamate and glycaurea compounds of the present invention can also be sulfated with chlorosulfonic acid, sulfur trioxide, sulfur trioxide/Lewis base complexes, oleum, sulfuric acid, sulfamic acid and the like as well as mixtures thereof, to give a series of novel sulfated sugar based anionic surfactants.

The glycacarbamate and glycaurea compounds of the present invention can also be phosphorylated with phophorus oxychloride, phosphorous pentoxide, polyphosphoric acid, phosphoric acid, phosphorus trichloride and the like as well as mixtures thereof, to give a series of novel phosphated sugar based esters (mono-, di-, and triesters as well as mixtures thereof) as anionic surfactants.

Process of Manufacture of Glycacarbamate and Glycaurea Compounds

In a particular embodiment of the invention, a new and improved process for the manufacture of glycacarbamate and glycaurea compounds is described.

It has been found, in accordance with the present invention, that (I) new and known glycacarbamate or glycaurea compounds as well as mixtures thereof may be readily prepared by reacting urea or substituted ureas with substituted glycamines (sugar-$NHR_3$ wherein $R_3$ is usually not hydrogen) in the presence or absence of a base catalyst at elevated temperatures (Δ) optionally followed by color improvement with an oxidizing or reducing agent.

It has been further found, in accordance with the present invention, that (II) new and known glycaurea compounds may also be readily prepared by reacting alkali metal cyanates with substituted glycamines (sugar-NHR$_3$ wherein R$_3$ is hydrogen) in the presence of water or an aqueous solvent system and a strong non-oxidizing mineral acid at elevated temperatures (Δ) optionally followed by color improvement with an oxidizing or reducing agent.

The glycacarbamate and glycaurea compounds of the invention are prepared without hydroxyl group protection, oligomerization or polymerization and are isolated in good yield, high purity and desirable color.

Examples of glycamines (1-alkylamino-1-deoxyalditols, 2-alkylamino-2-deoxyketitols etc.) suitable for this method include those of the formula:

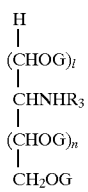

wherein G is hydrogen, $(CH_2CH_2O)_qH$ or $(CH_2CHCH_3O)_rH$ group, a mono-, di-, oligo- or polysaccharide or mixtures thereof; q and r are each from about 0 to about 50 and the sum of q and r are from about 0 to about 50; n is from about 1 to about 6, I is from about 0 to about 8 and the sum of n and I are from about 0 to about 10; and R$_3$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 35 carbon atoms.

Specific examples of glycamines most useful in the present invention which have more commonly names include, but are not limited to glucamine (1-deoxysorbitol), methylglucamine (1-methylamine-1-deoxyglucitol or 1-methylamine-1-deoxysorbitol), ethylglucamine, propylglucamine, butylglucamine, octylglucamine, decylglucamine, dodecylglucamine, isotridecylglucamine, tetradecylglucamine, hexadecylglucamine, octadecylglucamine, coconutglucamine, soyaglucamine, tallowglucamine, palmglucamine, octadecenylglucamine (oleylglucamine), linolenylglucamine, hydroxyethylglucamine, disorbitylamine, methyloxypropylglucamine, octyl/decyloxypropylglucamine, dodecyloxypropylglucamine, dodecyl to pentadecyloxypropylglucamine, $C_1-C_{35}$ oxypropylpoly(oxyethyl)glucamine, coconut-aminopropylglucamine, methyllactamine [galactopyranosyl-β-(1–4)-1-methylamino-1-deoxyglucitol], hydroxyethyllactamine, dodecyllactamine, tetradecyllactamine, coconut-lactamine, tallowlactamine, tetradecyloxypropyllactamine, methylmaltamine [glucopyranosyl-α- (1–4)-1-methylamino-1-deoxyglucitol], octylmaltamine, decylmaltamine, dodecylmaltamine, isotridecylmaltamine, tetradecylmaltamine, hexadecylmaltamine, octadecylmaltamine, coconut-maltamine, soyamaltamine, tallowmaltamine, octadecenylmaltamine (oleylmaltamine), linolenylmaltamine, hydroxyethylglucamine, dimaltamine, octyl/decyloxypropylmaltamine, dodecyloxypropylmaltamine, dodecyl to pentadecyloxypropylmaltamine, $C_1-C_{35}$ oxypropylpoly-(oxyethyl)maltamine, coconutaminopropylmaltamine, dimethylaminopropylglucamine, dimethylaminoethylglucamine and the like.

Examples of other glycamines (1-alkylamino-1,6-dideoxyalditols) suitable for this method include those of the formula:

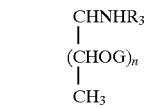

wherein G is hydrogen (H), a $(CH_2CH_2O)_qH$ or $(CH_2CHCH_3O)_rH$ group, a mono-, di-, oligo- or polysaccharide or mixtures thereof; q and r are each from about 0 to about 50 and the sum of q and r are from about 0 to about 50; n is from about 1 to about 6; and R$_3$ is hydrogen (H), a straight or branched chain saturated or unsaturated hydrocarbon which may be unsubstituted or substituted with a hydroxyl, polyhydroxyl, aromatic, cycloaliphatic or mixed aromatic radical having about 1 to about 31 carbon atoms.

Specific examples of other glycamines useful in the present invention include, but are not limited tolmethylamino-1,6-dideoxyrhamnitol, 1-dodecylamino-1,6-dideoxyrhamnitol, 1-coconutamino-1,6-dideoxyrhamnitol, 1-methyloxypropylamino-1,6-dideoxyrhamnitol, 1-amino-1-deoxyketoses and 1-alkylamino-1-deoxyketoses, 6-methylaminosorbitan, 1-amino-1-deoxyaldoses, 1-alkylamino-1-deoxyaldoses, 2-amino-2-deoxyaldoses, 2-alkylamino-2-deoxyaldoses, 6-amino-6-deoxyketoses, 6-alkylamino-6-deoxyketoses, 6-amino-6-deoxyaldoses, 6-alkyl-amino-6-deoxyaldoses, 6-amino-6-deoxyglycosides, 6-alkylamino-6-deoxyglycosides and the like.

Examples of ureas suitable for this method include, but are not limited to urea, methylurea, octylurea, nonylurea, decylurea, undecylurea, dodecylurea, tridecylurea, isotridecylurea, tetradecylurea, pentadecylurea, hexadecylurea, heptadecylurea, octadecylurea, coconuturea, soyaurea, tallowurea, dodecenylurea, octadecenylurea (oleylurea), linoleylurea, linolenylurea and the like.

Examples of cyanates suitable for this method include, but are not limited to hydrogen cyanide, sodium cyanate, potassium cyanate, lithium cyanate, magnesium cyanate and the like.

Description of the Essential Process Parameters of (I) and (II)

Within the process of the invention (I), it is desirable to use nearly water-free reaction components, however this is not an essential condition. Also, within the process of the invention, the glycamine can be added progressively to the urea, or the urea can be added progressively to the glycamine, or all reagents can be added at the beginning of the reaction, preferably however, the urea is added in full amount to the glycamine. The glycamine can be used in molar excess relative to the urea or the urea can be used in molar excess relative to the glycamine, preferably however, as seen in Examples 1 through 11, the reagents are used in stoichiometric molar amounts. When the molar ratio of urea to glycamine is in excess, it may be in slight excess. The molar ratio of urea to glycamine may be from about 1.3:1 to about 1.01:1, preferably from about 1.2:1 to about 1.02:1, more preferably from about 1.1:1 to about 1.03:1.

Within the process of the invention (II), it is not neccessary to use nearly water-free reaction components. Also, within the process of the invention, the glycamine can be added progressively to the cyanate, or the cyanate can be added progressively to the glycamine, or all reagents can be added at the beginning of the reaction, preferably however, the cyanate is added in full amount to the glycamine. The glycamine can be used in molar excess relative to the cyanate or the cyanate can be used in molar excess relative to the glycamine, preferably however, as seen in Examples 12 through 16, the reagents are used in stoichiometric molar amounts. When the molar ratio of glycamine to cyanate is in excess, it may be in slight excess. The molar ratio of glycamine to cyanate may be from about 1.3:1 to about 1.01:1, preferably from about 1.2:1 to about 1.02:1, more preferably from about 1.1:1 to about 1.03:1.

The glycamine, urea or cyanate is preferably in crystalline to granular form, however solid, flake, paste, gel or liquid forms can be used as well.

Within the process of the invention (I), the reaction is performed at elevated temperatures and is usually preferred. Favorable reaction temperatures are from about 65° C. to about 220° C., preferably from about 90° C. to about 195° C., more preferably from about 100° C. to about 185° C., most preferably at least 10° C. above the melting point of the alkylglycamine. At temperatures below 110° C. the reaction is quite slow and at temperatures appreciably greater than 175° C. most reactants and products decompose, particularly at long reaction times. Temperatures in the range of 110° C. to 160° C. tend to favor the formation of glycaurea compounds, whereas temperatures in the range of 140° C. to 175° C. tend to favor the formation of glycacarbamate compounds. A mixture of glycarbamate and glycaurea compounds is also possible, however very long reaction times tend to favor the formation of glycacarbamate compounds.

Within the process of the invention (II), the reaction is performed at elevated temperatures and is usually preferred. Favorable reaction temperatures are from about 5° C. to about 150° C., preferably from about 7° C. to about 120° C., more preferably from about 10° C. to about 100° C. At temperatures below 10° C. the reaction is quite slow.

The reaction (I) may be carried out under reduced pressure to assist in the removal of ammonia which is captured in an ammonia absorption tower, however it is preferably carried out at atmospheric pressure and under an inert gas blanket such as nitrogen, argon or helium whereas, the reaction (II), is preferably carried out at atmospheric pressure.

Optionally a catalyst can be used to accelerate the rate of the reaction (I) and is generally classified as an organic or inorganic base. Preferred base catalysts include sodium hydroxide, sodium methoxide, sodium carbonate, potassium carbonate, sodium bicarbonate, trisodium citrate, sodium laurate, disodium oxalate, triethylamine, tripropyl-amine, monoethanolamine, diethanolamine and triethanolamine.

The base catalyst can be added at any time during the reaction, however, it is preferably added at the beginning of the reaction and in full amount. The molar ratio of glycamine to base catalyst is from about 700:1 to about 1:1, preferably from about 500:1 to about 100:1, most preferably from about 250:1 to about 150:1.

The substrates are reacted with intensive stirring for several hours, preferably from about 0.5 hour to about 48 hours, more preferably from about 1 hour to about 24 hours, most preferably when the reaction is deemed complete by full evolution of ammonia and is verified by an analytical technique such as thin layer chromatography (TLC), infrared spectroscopy (IR), proton nuclear magnet resonance (H1 NMR), carbon 13 nuclear magnet resonance (C13 NMR), direct chemical ionization mass spectrometry (DCI MS), fast atom bombardment mass spectrometry (FAB MS) or high pressure liquid chromatography (HPLC).

In general, an organic solvent can be optionally used to perform reaction (I) and water or an aqueous organic solvent is perferably used to perform reaction (II). The quantity of water or solvent should be sufficient to dissolve the carbohydrate, urea and cyanate, but otherwise this is not an essential condition. Typical levels of solvent used are from about 5% to about 99%, preferably from about 15% to about 80%, most preferably from about 20% to about 60% by weight of the total reaction mixture. Preferably the solvent is removed (after the reaction is complete) by known procedures such as simple distillation, vacuum distillation or rotaevaporation. However, this may not be feasible when high boiling materials, such as propylene glycol, ethylene glycol, diethylene glycol, polyethylene glycol and the like are used as solvents, or when other useful composition ingredients such nonionic surfactants, sorbitol and the like, are used as pseudosolvents or phase transfer agents. These materials are preferably left in the finished product and generally do not present a problem. In fact, in some cases, it may be more beneficial.

When water is used, it may be removed by freeze drying, spray drying or vacuum distillation, however, it may be more economical to leave the water in and use it as a diluent making the product a pureable liquid. This can be applied to aqueous organic solvent systems as well. Typical levels of water or aqueous organic solvent used as a reaction medium or diluent are from about 5% to about 99%, preferably from about 15% to about 75%, most preferably from about 25% to about 60% by weight of the total reaction mixture.

In general, the glycacarbamate and glycaurea compounds of the present invention are usually isolated as solids or semisolids, however, when syrups are obtained, crystallization may be enhanced by the addition of an organic solvent. The resulting product is subsequently filtered, washed with an organic solvent and air or vacuum dried.

Optionally, further purification of (solid) glycacarbamate and glycaurea compounds can be performed by recrystallization in an organic solvent. The amount of solvent used is sufficient to dissolve the product, preferably with heating. The solution is then slowly cooled until recrystallization is complete, subsequently filtered, washed with an organic solvent and air or vacuum dried.

Still further purification of the glycacarbamate and glycaurea compounds of the present invention can be optionally performed by column chromatography. Such methods of purification are described in U.S. Pat. Nos. 5,296,588 and 5,336,765 to Au et al. which are both incorporated herein by reference.

Still further purification of glycacarbamate and glycaurea compounds of the invention can also be optionally performed by extraction from a mixture of water and organic solvent. A necessary criteria for extraction is that the organic solvent be immiscible with water. Preferably the glycacarbamate and glycaurea compounds should be soluble in water and the urea or alkylurea derivative should be soluble in the solvent, however this is not a necessary condition. The urea or alkylurea derivative are then extracted into the solvent layer and removed from the aqueous layer containing the glycacarbamate and glycaurea compound. The water and organic layers are separated from each other, the solvent is removed, and the components in that solvent layer can be purified or recycled. A mild vacuum is optionally applied to the aqueous layer, removing any trace solvents, and the water is left with the final product free of unreacted urea or alkylurea.

Typical reaction solvents, crystallization solvents and recrystallization solvents that may be used include, but are not limited to, acetone, acetonitrile, butanol, sec-butanol, tertbutanol, chloroform, dimethylformaide (DMF), dimethylacetamide, dimethylsulfoxide (DMSO), 2-ethoxyethanol, ethylacetate, ethyl ether, ethylene glycol dimethyl ether (glyme), propanol, isopropanol and the like, however. high boiling alcohols are the preferred reaction solvents for reaction (I), water or aqueous alcohol solvent sytems are the preferred reaction solvents for reaction (II). Furthermore, alcohols are also the preferred recrystallization solvents. Mixtures of solvents can be used as well and may be preferred in certain cases. Examples of most highly preferred alcohols includes, but are not limited methanol, ethanol, propanol, isopropanol, butanol, sec-butanol, tert-butanol, hexanol, dodecanol, coconut alcohol ($C_8$–$C_{18}$ alcohol), 2-ethoxyethanol, glycerol, ethylene glycol, propylene glycol, diethylene glycol, triethylene glycol, tetraethylene glycol, hexylene glycol, polyethylene glycol, ethylene glycol monobutyl ether (2-butoxyethanol), ethylene glycol monomethyl ether (2-methoxyethanol), cyclohexanol and the like.

Optionally, the reaction may also be carried out in the presence of phase transfer agent, such as a typical ethoxylated/propoxylated surfactant (e.g. ethoxylated alcohol, ethoxylated/propoxylated alcohol, propoxylated alcohol, alkylpolyglycoside etc.) which provides a homogeneous reaction phase.

When the reaction is complete (I), the base catalyst may be optionally neutralized with an organic or inorganic acid. However, in reaction (II), a strong non-oxidizing mineral acid is neccessary to generate the more reactive cyanic acid.

Preferred strong non-oxidizing mineral acids include, hydrochloric acid, sulfuric acid, phosporic acid and hydrobromic acid. The amount of non-oxidizing mineral acid used is usually in equal to a slight molar excess of acid to cyanate. The molar ratio of acid to cyanate may be from about 1.5:1 to about 1.01:1, preferably from about 1.3:1 to about 1.02:1, more preferably from about 1.2:1 to about 1.03:1.

Bleaching is sometimes required in either reactions (I) or (II) of the invention, but not always necessary, since compounds of the invention are usually of good color. Hydrogen peroxide and hydrogen peroxide liberating or generating compounds are preferred. Bleaching may be optionally done in water or in an inert organic solvent before or during the reaction or after the reaction is complete, preferably however, bleaching is done after the reaction is complete at about 0° C. to about 50° C. and in water or an organic solvent. Typical levels of bleaching agent are from about 0.01% to about 10%, preferably from about 0.02% to about 7%, even more preferably from about 0.03% to about 5% by weight of the total reaction mixture.

Color improvement may also be carried out in either reactions (I) or (II) of the invention by using reducing agents belonging to two classes.

The first class of agents comprises compounds which include sulfur in the +4 oxidation state and show a negative oxidation relative to hydrogen. Illustrative of this class are salts of sulfite, bisulfite, hydrosulfite (dithionite), metabisulfate (pyrosulfite) and mixtures thereof.

The second class of reducing agents includes those compounds having hydrogen in the −1 oxidation state and show a negative oxidation potential relative to hydrogen. Illustrative of this class are hydrides and borohydrides. Particularly preferred among the foregoing are the bisulfites and borohydrides, most especially preferred are sodium bisulfite and sodium borohydride and mixtures thereof Reduction may be optionally done in water or in an inert organic solvent before or during the reaction or after the reaction is complete, preferably however, reduction is done without water or an organic solvent and during or after the reaction is complete at about 0° C. to about 200° C. Typical levels of reducing agent are from about 0.01% to about 12%, preferably from about 0.02% to about 9%, even more preferably from about 0.03% to about 7% by weight of the total reaction mixture.

The glycacarbamate and glycaurea compounds prepared by the methods of the invention are generally isolated in good yield, high purity and desirable color.

Home Application and Use

The glycacarbamate and glycaurea compounds of the present invention are useful in detergent, personal product, food and pharmacological compositions which are available in a variety of types and forms. Preferred applications are personal product and detergent compositions.

A classification according to detergent type would consist of heavy-duty detergent powders, heavy-duty detergent liquids, light-duty liquids (dishwashing liquids), machine dishwashing detergents, institutional detergents, specialty detergent powders, specialty detergent liquids, laundry aids, pretreatment aids, after treatment aids, presoaking products, hard surface cleansers, carpet cleansers, carwash products, toilet boil cleaners, fabric softening products, fabric softening rinse conditioners, fabric softening sheets, metal cleaning detergents and the like.

A classification according to personal product type would consist of hair care products, bath products, cleansing products, skin care products, shaving products, deodorant/antiperspirant products and oral hygiene products.

Examples of hair care products include, but are not limited to rinses, conditioners shampoos, conditioning shampoos, antidandruff shampoos, antilice shampoos, coloring shampoos, curl maintenance shampoos, baby shampoos, herbal shampoos, hair loss prevention shampoos, hair growth/promoting/stimulating shampoos, hairwave neutralizing shampoos, hair setting products, hair sprays, hair styling products, permanent wave products, hair straightening/relaxing products, mousses, hair lotions, hair tonics, hair promade products, brilliantines and the like.

Examples of bath products include, but are not limited to bath oils, foam or bubble bathes, therapeutic bathes, after bath products, after bath splash products and the like.

Examples cleansing products include, but are not limited to shower cleansers, shower gels, body shampoos, hand/body/facial cleansers, abrasive scrub cleansing products, astringent cleansers, makeup cleansers, liquid soaps, toilet soap bars, syndet bars and the like.

Examples of skin care products include, but are not limited to hand/body/facial moisturizers, hand/body/facial creams, massage creams, hand/body/facial lotions, sunscreen products, tanning products, selftanning products, aftersun products, masking products, lipsticks, lip gloss products, rejuvenating products, antiaging products, antiwrinkle products, anticellulite products, antiacne products and the like.

Examples of shaving products include, but are not limited to shaving creams, aftershave products, preshave products and the like.

Examples of deodorant/antiperspirant products include, but are not limited to deodorant products, antiperspirant products and the like.

Examples of oral hygiene products include, but is not limited to mouthwashes, prebrushing dental rinses, post-bushing rinses, dental sprays, dental creams, toothpastes, toothpaste gels, toothpowders, dental cleansers, dental flosses, chewing gums, lozenges and the like.

A classification according to personal product and detergent form would consist of aerosols, liquids, gels, creams, lotions, sprays, pastes, roll-on, stick, tablet, powdered, granualar and bar form.

A comprehensive list of essential and optional ingredients that are useful in personal product and detergent compositions are described in McCutcheon's, Detergents and Emulsifiers (Vol 1) and McCutcheon's, Functional Materials (Vol 2), 1996 Annual Edition, published by McCutcheon's MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

COMPOSITIONS

There are a wide variety of essential and optional ingredients that can be used in personal product and detergent compositions depending on the characteristics and end purpose sought. Such ingredients are well known to those skilled in the art.

For example, ingredients useful in hare care products include, but are not limited to surfactants, antidandruff agents hair conditioning agents, suspending agents, auxiliary thickening agents, hair styling agents, viscosity control agents, emulsifiers/emollients, dispersants, conditioning emollient oils, conditioning extracts, humectants, solubilizing/clarifying agents, stabilizers, sunscreens/UV absorbers, opacifiers/pearlescent agents, vitamins, amino acids, proteins, curl enhancing agents, hair coloring agents, chelating/sequestering agents, hydrotropes, antilice agents, hair straightening agents, preservatives/antimicrobial agents, bactericides/fungicides, antioxidants, brightening agents (bleaches), pH control agents, buffering agents, colorants and perfumes/fragrances, water, other optional ingredients (auxilary agents) and the like.

Ingredients useful in bath, skin care, shaving, deodorant/antiperspirant products include, but are not limited to surfactants, skin conditioning agents, skin feel mildness agents, suspending agents, hydroxy acids, auxiliary thickening agents, viscosity control agents, dispersants, solubilizing/clarifying agents, stabilizers, sunscreens/UV absorbers, opacifiers/pearlescent agents, vitamins, amino acids, proteins, chelating/sequestering agents, hydrotropes, preservatives/antimicrobial agents, bactericides/fungicides, antioxidants, pH control agents, buffering agents, antiperspirant/deodorant agents, heeling agents, colorants and perfumes/fragrances, water, other optional ingredients (auxilary agents) and the like.

Ingredients useful in oral hygiene products include, but are not limited to abrasive polishing agents, humectants, alcohols, binding/thickening agents, cosurfactants, astringents, antiplaque agents, anticalculus agents, antibacterial agents, pH-buffering salts, alkali metal halides (salts), flavorants, sweeteners, fluorides, colorants, desensitizing agents, heeling agents, other preventive caries agents, chelating/sequestering agents, vitamins, amino acids, proteins, other antiplaque/anticalculus agents, opacifiers, antibiotics, antienzymes, enzymes, pH control agents, oxidizing agents, antioxidants, whitening agents and preservatives/antimicrobial agents, water, optional ingredients (auxiliary agents) and the like.

Ingredients useful in detergent products include, but are not limited to surfactants, bleaching agents, builders, enzymes, enzyme costabilization systems, optical brightening agents, chelating agents, dispersing agents, antiredeposition agents, soil release agents, suds suppressors, cothickening agents, abrasive agents, viscosity control agents, solubilizing/clarifying agents, sunscreens/UV absorbers, opacifiers/pearlescent agents, hydrotropes/phase regulants, foam boosters/stabilizers, preservatives/antimicrobial agents, bactericides/fungicides, antioxidants, certain metal ions, pH control agents, buffering agents, color speckles, encapsulation agents, antitarnish agents, deflocculating agents, fillers, skin protective agents, dye transfer inhibiting agents (colorcare agents), dyes/colorants, fragrances/perfumes, optional ingredients (auxilary agents), water and the like.

The individual ingredients have to fulfill, in part, wholly different functions while at the same time each ingredient must complement and increase the effect of other substances. This has always been a difficult challenge to meet and finding the right combination of ingredients for improved cleansing, pearlescence, suspension, viscosity, flow and detergency is a significant achievement.

Detailed Description of Essential and Optional Ingredients

A detailed description of some of the essential and optional ingredients of the present invention are given in the following paragraphs.

Examples of an essential component useful in the detergent and personal product compositions of the present invention include, but are not limited to a surfactant or cosurfactant. The terms "surfactant and cosurfactant" are used to denote both soap and nonsoap surface-active agents. The nonsoap surface-active agents include anionic, nonionic, amphoteric, zwitterionic and cationic surfactants.

Soaps

Suitable soaps are exemplified as alkali metal, ammonium or alkanolammonium salts of aliphatic alkane or alkene monocarboxylic acids having about 6 to about 22 carbon atoms. Sodium, potassium, ammonium, mono-, di-, and triethanolammonium cations or combinations thereof, are preferred. Soaps may be prepared by either direct saponification of fats and oils or by neutralization of free fatty acids. Particularly useful are the sodium, potassium, ammonium and alkanolammonium salts of lauric acid, myristic acid, palmitic acid, stearic acid, oleic acid, linoleic acid, ricinoleic acid, coconut fatty acid, palm kernel fatty acid and tallow fatty acid.

Anionic Surfactants

Suitable anionic surfactants are broadly exemplified as alkali metal, ammonium or alkanolammonium salts of organic reaction products having an aliphatic alkyl, alkene or alkyl aromatic group with about 6 to about 28 carbon atoms and at least one water solubilizing radical selected from the group consisting of phosphate, phosphonate, sulfonate, sulfate or carboxylate.

An example of a suitable class of anionic surfactant useful in the present invention are the sodium, potassium and ammonium salts of alkyl benzene sulfonates in which the alkyl group contains from about 8 to about 18 carbon atoms in branched or preferably in straight chain configuration. Alkyl benzene sulfonates are prepared by sulfonation of linear $C_8$–$C_{18}$ alkyl benzenes with sulfur trioxide in a falling film or tube bundle reactor followed by neutralization with base. Other suitable sulfonating agents used to prepare $C_8$–$C_{18}$ alkyl benzene sulfonates include oleum, chlorosulfonic acid, sulfuric acid or sulfur trioxide complexes. Examples of suitable alkali metal, ammonium and alkanolammonium salts of alkyl benzene sulfonates are disclosed in U.S. Pat. Nos. 2,220,099 and 2,477,383 both of which are incorporated herein by reference. Specific examples of alkyl benzene sulfonates useful in the present invention include sodium dodecyl benzene sulfonate, potassium dodecyl benzene sulfonate, ammonium dodecyl benzene sulfonate, sodium $C_{11}$–$C_{13}$ alkyl benzene sulfonate, sodium tetra-decyl benzene sulfonate, ammonium tetradecyl benzene sulfonate and mixtures thereof.

A preferred class of anionic surfactant found to be useful in the present invention are the sodium, potassium and ammonium salts of alkyl sulfates, especially those obtained by sulfating higher $C_8$–$C_{18}$ alkyl alcohols produced naturally from coconut oil or those prepared synthetically from petroleum sources. Specific examples of alkyl sulfates useful in the present invention include sodium dodecyl sulfate, potassium dodecyl sulfate, ammonium dodecyl sulfate, monoethanolammonium dodecyl sulfate, diethanolammonium dodecyl sulfate, triethanolammonium dodecyl sulfate, sodium tetradecyl sulfate, potassium tetradecyl sulfate, ammonium tetradecyl sulfate, monoethanolammonium tetradecyl sulfate, triethanolammonium tetradecyl sulfate, sodium hexadecyl sulfate, ammonium hexadecyl sulfate, sodium coconut sulfate, sodium $C_{12}$–$C_{15}$ alkyl sulfate and mixtures thereof. Alkyl sulfates are sold commercially under several trade names which includes Carsonol ALS and Carsonol DLS, Carsonol SLS and Carsonol sold by Lonza Inc.; Duponol QC, Duponol D Paste, Duponol EP, Duponol G, Duponol LS Paste and Duponol WA Paste sold by Witco Corporation; Rhodapon CAV, Rhodapon L22, Rhodapon LSB, Rhodapon LT-6 and Rhodapon TDS sold by Rhone-Poulenc; Standpol A and Standpol DEA sold by Henkel Corporation; Sulfochem ALS, Sulfochem DLS, Sulfochem TLS and Sulfochem SLS sold by Chemron.

Another preferred class of anionic surfactant found to be most useful in the present invention are the sodium, potassium and ammonium salts of alkyl ether sulfates which are obtained by sulfating the higher $C_8$–$C_{18}$ alcohol ethoxylates. Such alcohols are reacted with about 1 to about 25 moles of alkylene oxide followed by sulfation and neutralization with base. Most highly preferred alkyl ether sulfates useful in the present invention include those comprising a mixture of individual compounds having an average chain length of about 10 to about 18 carbon atoms and an average degree of alkoxylation of about 1 to about 4 moles of ethylene oxide. Such a mixture can comprise from about 0% to about 50% by weight $C_{10}$–$C_{11}$ alkyl ether sulfate, from about 20% to about 100% by weight $C_{12}$ alkyl ether sulfate, from about 0% to about 80% by weight $C_{13}$–$C_{14}$–$C_{15}$–$C_{16}$ alkyl ether sulfates and from about 0% to about 30% by weight $C_{17}$–$C_{18}$ alkyl ether sulfates; and from about 5% to about 90% by weight of compounds having a degree of alkoxylation of 0; from about 7% to about 95% by weight of compounds having a degree of alkoxylation of 1 to 4; and from about 0% to about 35% by weight of compounds having a degree of alkoxylation greater than 5. Specific examples of alkyl ether sulfates useful in the present invention include sodium laureth-1 sulfate, sodium laureth-2 sulfate, sodium laureth-3 sulfate, potassium laureth-1 sulfate, potassium laureth-2 sulfate, potassium laureth-3 sulfate, ammonium laureth-1 sulfate, ammonium laureth-2 sulfate, ammonium laureth-3 sulfate, monoethanolammonium laureth-1 sulfate, monoethanolammonium laureth-2 sulfate, monoethanolammonium laureth-3 sulfate, diethanolammonium laureth-1 sulfate, diethanolammonium laureth-2 sulfate, diethanolammonium laureth-3 sulfate, triethanolammonium laureth-1 sulfate, triethanolammonium laureth-2 sulfate, triethanolammonium laureth-3 sulfate, sodium myreth-1 sulfate, sodium myreth-2 sulfate, sodium myreth-3- sulfate, ammonium myreth-1 sulfate, ammonium myreth-2 sulfate, ammonium myreth-3 sulfate, sodium $C_{10}$–$C_{16}$ alkyl (1) ether sulfate, sodium $C_{10}$–$C_{16}$ alkyl (2) ether sulfate, sodium $C_{10}$–$C_{16}$ alkyl (3) ether sulfate and mixtures thereof. Alkyl ether sulfates are sold commercially under several trade names which includes Carson SLES-2 and Carson SES-A sold by Lonza Inc.; Duponol FAS sold by Witco Corporation; Norfox SLES-03 and Norfox SLES-60 sold by Norman, Fox & Co.; Standpol EA-1, Standpol EA-2, Standpol EA-3, Standpol EA-40, Standpol ES-1, Standpol ES-2, Standpol ES-3, Standpol ES-40, Standpol ES-50, Standpol ES-250 and Standpol 350 sold by Henkel Corporation; Sulfochem EA-1, Sulfochem EA-2, Sulfochem EA-3, Sulfochem EA-60, Sulfochem EA-70, Sulfochem ES-1, Sulfochem ES-2, Sulfochem ES-3, Sulfochem ES-60, Sulfochem ES-70 and Sulfochem K sold by Chemron.

Nonionic Surfactants

Suitable commercial nonionic surfactants are broadly exemplified as the polyoxyalkylene oxide condensation products of hydrophobic alkyl, alkene, or alkyl aromatic functional groups having a free reactive hydrogen available for condensation with hydrophilic alkylene oxide, such as ethylene oxide, propylene oxide, butylene oxide, polyethylene oxide or polyethylene glycol to form nonionic surfactants. Examples of such hydrophobic functional groups include hydroxy, carboxy, mercapto, amino or amido groups.

The overall reaction may be expressed as:

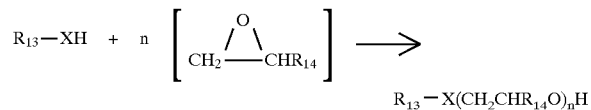

wherein $R_{13}$ is a hydrophobic alkene or alkane group having about 8 to about 18 carbon atoms; $R_{14}$ is hydrogen or an alkyl group with about 1 to about 2 carbon atoms; n is from about 1 to about 100; X is selected from the group consisting of O, $C_6H_4O$, $C_6H_3R_{13}O$, COO, S, NH, $NR_{15}$, CONH, $CONR_{15}$, $CONR_{15}(CH_2)_a(NR_{15})_2$ and $CONR_{15}(CH_2)_b NR_{15}(CH_2)_c N(R_{15})_2$; where $R_{15}$ is selected from the group consisting of H, $(CH_2CH_2O)_d$, $(CH_2CHCH_3O)_e$ and mixtures thereof; a+b +c is from about 1 to about 10; and d+e is from about 1 to about 200.

Examples of nonionic surfactants as well as other surfactants which may be useful in the present invention are described in U.S. Pat. No. 5,624,906 to Vermeer which is incorporated herein by reference.

A preferred class of nonionic surfactant found to be useful in the present invention are the polyoxyalkylene alkyl alcohols having about 8 to about 18 carbon atoms in either branched or preferably straight chain configuration and about 1 to about 100 moles of ethylene oxide. Particularly preferred are the condensation products of alcohols having an alkyl group containing about 10 to about 16 carbon atoms with from about 3 to about 40 moles of ethylene oxide per mole of alcohol. Specific examples of commercially available nonionic surfactants of this type include Tergitol 15-S-9 (the condensation product of $C_{11}$–$C_{15}$ linear secondary alcohol with 9 moles of ethylene oxide and a narrow molecular weight distribution) and Tergitol 24-L-6 NMW (the condensation product of $C_{12}$–$C_{14}$ primary alcohol with 6 moles of ethylene oxide) both sold by Union Carbide Corporation; Neodol 45-7 (the condensation product of $C_{14}$–$C_{15}$ linear alcohol with 7 moles of ethylene oxide), Neodol 45-9 (the condensation product of $C_{14}$–$C_{15}$ linear alcohol with 9 moles of ethylene oxide), Neodol 23-6.5 (the condensation product of $C_{12}$–$C_{13}$ linear alcohol with 6.5 moles of ethylene oxide), Neodol 45-4 (the condensation product of $C_{14}$–$C_{15}$ linear alcohol with 4 moles of ethylene oxide), Neodol 25-7 (the condensation product of $C_{12}$–$C_{15}$ linear alcohol with 7 moles of ethylene oxide and Neodol 25-9 (the condensation product of $C_{12}$–$C_{15}$ linear alcohol with 9 moles of ethylene oxide) all sold by Shell Chemical Company. The CTFA adopted name for this class of nonionic surfactant is laureth-x (PEG-x lauryl ether), isolaureth-x (PEG-x isolauryl ether), myreth-x (PEG-x myristyl ether), ceteth-x (PEG-x cetyl ether), steareth-x (PEG-x stearyl ether), oleth-x (PEG-x oleyl ether), cetoleth-x (PEG-x cetyl/oleyl ether) and ceteareth-x (PEG-x cethyl/stearyl ether) wherein x is about 1 to about 100 and represents the degree of ethoxylation. Preferred are laureth-4 through 25, myreth-4 through 10, ceteth-5 through 30 and stearth-3 through 40. The polyoxyalkylene alkyl alcohols having about 4 to about 18 carbon atoms in either branched or preferably straight chain configuration and about 1 to about 100 moles of propylene oxide are useful as well. Particularly preferred are the condensation products of alcohols having an alkyl group containing about 10 to about 16 carbon atoms with from about 3 to about 40 moles of propylene oxide per mole of alcohol. Specific examples of commercially available nonionic surfactants of this type include PPG-y butyl ether, PPG-y decyl ether, PPG-y lauryl ether, PPG-y isolauryl ether, PPG-y myristyl ether, PPG-y cetyl ether, PPG-y stearyl ether, PPG-y oleyl ether, PPG-y cetyl/oleyl ether and PPG-y cethyl/stearyl ether wherein y is about 1 to about 100 and represents the degree of propoxylation.

Amphoteric Surfactants

There are two classes of amphoteric surfactant; those that are pH sensitive (amphoteric) and those that are pH insensitive (zwitterionic).

Suitable amphoteric surfactants are exemplified as those which can be broadly classified as derivatives of aliphatic secondary and tertiary amines which contain a quaternary ammonium or non-quaternary ammonium group and one long chained alkyl or alkene group having about 8 to about 18 carbon atoms and at least water solubilizing radical selected from the group consisting of sulfates, sulfonates, carboxylates, phosphates or phosphonates.

Examples of such amphoteric surfactants include the N-alkyl β-amino propionates, such as sodium(dodecyl β-amino)propionate (sodium lauraminopropionate), diethanolamine lauraminopropionate and sodium cocoaminopropionate; the N-alkyl β-imino dipropionates, such as disodium(dodecyl β-imino)dipropionate (sodium lauriminodipropionate) and cocoiminodipropionate; the alkyl taurinates, such as monoethanolammonium coconut taurinate as taught in U.S. Pat. No. 2,658,072 which is incorporated herein by reference and the derivatives derived from 2-alkyl-2-imidazoline, such as those sold under the trade name Miranol as taught in U.S. Pat. Nos. 2,528,378, 2,773,068, 2,781,354 and 2,781,357 all of which are incorporated herein by reference. The amphoteric imidazoline derived surfactants are a preferred class of amphoteric surfactant and are prepared by condensing aminoethylethanolamine, diethylenetriamine or ethylenediamine with a fatty acid having about 8 to about 18 carbon atoms to form a five-membered imidazoline ring which may be ionized by an anionizable alkylating agent such as sodium chloroacetate, methyl or ethyl acrylate, acrylic acid, 2-hydroxy-1,3-propane sultone, 3-chloro-2-hydroxypropane sulfonic acid and 1,3-propane sultone on or near the cyclic portion or cationic portion of the molecule. Alkylations may be done with or without solvent or in aqueous solution. In aqueous solution, the imidazoline ring may be hydrolytically opened to form a mixture of imidazoline and linear amide. Specific examples of amphoteric imidazoline-derived surfactants useful in the present invention include lauroamphocarboxypropionate, lauroamphopropionate, lauroamphoglycinate, lauroamphocarboxyglycinate, lauroamphopropylsulfonate, lauroamphocarboxypropionic acid, myristoamphocarboxypropionate, myristoamphopropionate, myristoamphoglycinate, myristoamphocarboxyglycinate, myristoamphopropylsulfonate, myristoamphocarboxypropionic acid, cocoamphocarboxypropionate, cocoamphopropionate, cocoamphoglycinate, cocoamphocarboxyglycinate, cocoamphopropylsulfonate, cocoamphocarboxypropionic acid and mixtures thereof. The CTFA adopted name for this class of amphoteric surfactant is amphoteric-1 through 20. Preferred are amphoteric-1, 2, 6, 10, 12, 17, 18, 19, 20 and mixtures thereof.

Zwitterionic Surfactants

Suitable zwitterionic surfactants are exemplified as those which can be broadly described as derivatives of aliphatic quaternary ammonium, sulfonium and phosphonium compounds with one long chain group having about 8 to about 18 carbon atoms and at least one water solubilizing radical selected from the group consisting of sulfate, sulfonate, carboxylate, phosphate or phosphonate. A general formula for these compounds is:

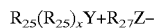

wherein $R_{25}$ contains an alkyl, alkene or hydroxyalkyl group with about 8 to about 18 carbon atoms, from about 0 to about 10 moles of ethylene oxide and from about 0 to about 2 glyceryl units; Y is a nitrogen, sulfur or phosphorous atom; $R_{26}$ is an alkyl or hydroxyalkyl group with about 1 to about 3 carbon atoms; x is 1 when Y is a sulfur atom and 2 when Y is a nitrogen or phosphorous atom; $R_{27}$ is an alkyl or hydroxyalkyl group with about 1 to about 5 carbon atoms and Z is radical selected from the group consisting of sulfate, sulfonate, carboxylate, phosphate or phosphonate. Examples of such zwitterionic surfactants include the sulfatobetaines, such as 3-(dodecyidimethylammonio)-1-propane sulfate and 2-(cocodimethylammonio)-1-ethane sulfate, soyaamidopropylethyldimonium ethosulfate; the sulfobetaines, such as 3-(dodecyldimethylammonio)-2-hydroxy-1-propane sulfonate, 3-(tetradecyldimethylammonio)-1-propane sulfonate, 3-($C_{12}$–$C_{14}$ alkylamidopropyldimethylammonio) -2-hydroxy-1-propane sulfonate, 3-(cocodimethylammonio) -1-propane sulfonate; the carboxybetaines such as (dodecyidimethylammonio)acetate (lauryl betaine), (tetradecyldimethylammonio)acetate (myristyl betaine), (cocodimethylammonio)acetate (coconut betaine), (oleyldimethylammonio)acetate (oleyl betaine), (dodecyloxymethyldimethylammonio)acetate, (tetradecyloxyhydroxylpropyidimethylammonio)acetate, [cocodi(polyethoxyethanol)ammonio]acetate, (dodecyidimethylammonio)propionate, (dodecylamidopropyidimethylammonio)acetate, (cocoamidopropyldimethylammonio)acetate (also known as cocoamidopropyl betaine); the sulfoniobetaines such as (dodecyldimethylsulfonio)acetate and 3-(cocodimethylsulfonio)-1-propane sulfonate and the phosphoniobetaines such as 4-(trimethylphosphonio)-1-hexadecane sulfonate, 3-(dodecyldimethylphosphonio)-1-propane sulfonate, 2-dodecyldimethylphosphonio)-1-ethane sulfite, myristamidopropyidimethylamine phosphate and mixtures thereof.

Means for preparing many of the surfactant compounds of this class are described in U.S. Pat. Nos. 2,129,264, 2,697,656, 2,774,786, 2,813,898, 2,828,332, 3,265,719, 3,529,521 and German Pat. No. 1,018,421 all of which are incorporated herein by reference.

Of all the above described types of zwitterionic surfactants, preferred compounds include the sulfobetaines such as 3-(cocodimethylammonio)-1-propanesulfonate, 3-(cocodimethylammonio)-2-hydroxy-1-propanesulfonate and the carboxybetaines such as (cocodimethylammonio) acetate, (dodecylamidopropylammonio)acetate and (cocoamidopropylammonio)acetate, (cocoamidopropyl betaine).

Cationic Surfactants

Cationic surfactants have been taught in the art as conditioning agents for the skin. Suitable cationic surfactants are broadly exemplified as those of the general formula:

$[R_{28}R_{29}N+R_{30}R_{31}]A-$ wherein $R_{28}$ contains an alkyl, alkene or alkylphenyl group with about 10 to about 24 carbon atoms; $R_{29}$, $R_{30}$ and $R_{31}$ contains an alkyl, alkene or alkylphenyl group with about 10 to about 24 carbon atoms, or an alkyl or alkylhydroxy group with about 1 to about 5 carbon atoms; and A– can be any salt forming anion such as halide, hydroxide, sulfate, carbonate and phosphate.

Examples of such cationic surfactants include myristyltrimethyl ammonium chloride, cetyltrimethylammonium chloride, stearyltrimethylammonium chloride and the like.

Many additional non-soap surfactants are described in McCutcheon's Detergents and Emulsifiers (Vol. 1) and McCutcheon's Functional Materials (Vol. 2), 1992 Annual, published by MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

The above mentioned surfactants (anionic, nonionic, amphoteric, zwitterionic, cationic surfactant and mixtures thereof) are used in combination with the alkyl glycacarbamate and alkyl glycaurea compounds of the present invention.

Typical levels of cosurfactant are from about 0% to about 70%, preferably from about 0.1% to about 55%, even more preferably from about 0.2% to about 40% by weight of the composition.

Other Ingredients

Examples of antidandruff agents useful in the personal product compositions of the present invention include, but are not limited to menthol, sulfur, salicylic acid, coal tar and the like. Currently however, most authorities in this area recognize that antidandruff agents based on pyridinethione salts or selenium sulfide are most effective against dandruff, and such materials are preferred. It should be understood that any such antidandruff agent can be employed herein, depending on the formulators desires, however, the pyridinethione salts are most especially preferred. The pyridinethione salts are based on suitable heavy metals such as zinc, cadmium, magnesium, tin, aluminum and zirconium, however, zinc as in zinc pyridinethione (zinc pyrithione) is highly preferred. Mixtures of antidandruff agents can also be used. The use of pyridinethione salts as antidandruff agents in shampoos and hair rinses are disclosed in the U.S. Pat. Nos. 2,809,971, 3,236,733, 3,723,325, 3,753,916, 3,761,417 and 3,761,418 all of which are incorporated herein by reference. Typical levels of antidandruff agent are from about 0% to about 8%, preferably from about 0% to about 6%, even more preferably from about 0% to about 4% by weight of the composition.

Examples of hair conditioning agents useful in the personal product compositions of the present invention include, but are not limited to lanolin and its derivatives, long chain esters such as isopropyl myristate, butyl palmitate, stearyl stearate, carylic/capric triglycerides, polyols such as glycerol (glycerin), propylene glycol and the like, oils, amine oxides, fatty alcohols, carbohydrates, fatty acids, alkyl pyrrolidones, polyvinylpyrrolidone (PVP), sodium PCA, vitamins, amino acids, silicones and certain cationic surfactants. Silicones and cationics are particularly preferred. Suitable non-volatile silicone fluids are exemplified as polyalkylsiloxane, polyarylsiloxane, polyalkylarylsiloxane and polyethersiloxane copolymers which are present at about 0% to about 10%, preferably from about 0% to about 8%, even more preferably from about 0% to about 6% by weight of the composition. Mixtures of these fluids may also be used and are preferred in certain executions. References that describe suitable silicone fluids include U.S. Pat. Nos. 2,826,551, 3,964,500, 4,364,837, British Pat. No. 849,433 and Silicon Compounds distributed by Petrarch Systems, Inc. all of which are incorporated herein by reference. The silicone fluids are present from about 0% to about 10%, preferably from about 0% to about 8%, even more preferably from about 0% to about 6% by weight of the composition.

Examples of suspending agents useful in the personal product and detergent compositions of the present invention include, but are not limited to any of several long chain acyl derivatives or mixtures thereof. Included are the glycol mono-, di- and triesters having about 14 to about 22 carbon atoms. Preferred glycol esters include the ethylene glycol mono- and distearates, glyceryl stearates, palm oil glyceride, tripalmitin, tristearin and mixtures thereof. Another example of a suspending agent useful in the present invention include the alkanolamides having from about 14 to about 22 carbon atoms. Preferred alkanolamides are stearic monoethanolamide, steric diethanolamide, stearic monoisopropanolamide, stearic monoethanolamide stearate and mixtures thereof. Still another example of a suspending agent useful in the present invention include the long chain fatty acid esters such as stearyl stearate, stearyl palmitate and palmityl palmitate. Still another example of a suitable suspending agent useful in the present invention include the long chain amine oxides having from about 14 to about 22 carbon atoms. Preferred amine oxides are hexadecyldimethylamine oxide and octadecyldimethylamide oxide. Yet another example of a suitable suspending agent (or thickening agent) useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum. Of all the above described types of suspending agents, preferred compounds include the long chain glycol esters and the carbohydrate gums. The suspending agent or mixtures of agent may be present from about 0% to about 7%, preferably from about 0% to about 5%, even more preferably from about 0% to about 4% by weight of the composition.

Examples of thickening agents useful in the personal product and detergent compositions of the present invention include, but are not limited to fumed silica, bentonite (hydrated aluminum silicone dioxide), PEG 55 propylene glycol oleate, PEG 6000 distearate, cellulose gum, hydroxypropyl cellulose, hydroxyethyl cellulose, hydroxypropyl methyl cellulose, sodium carboxymethyl cellulose, carrageenan, veegum (magnesium aluminum silicate), xanthan gum, gaur hydroxypropyltrimonium chloride, gaur gum, pectin, amine oxides, glucose glutamate, stearamidopropyldimethylamine lactate and the alkanolamides. Examples of another type of thickening agent (gelling agent/viscosity control agent) found to be useful in the present invention include the poly(oxyethylene)poly(oxypropylene) block copolymers such as poloxamer 101 through 941 sold by BASF, ICI Americas and Hodag. Preferred thickeners are the alkanolamides which are prepared by the reaction of a $C_8$–$C_{18}$ alkyl fatty acid, $C_8$–$C_{18}$ alkyl fatty acid ester or $C_8$–$C_{18}$ alkyl fatty acid halide with a hydroxyl alkylamine such as monoethanolamine or diethanolamine. Suitable examples of alkanolamides useful as auxiliary thickening agents include lauric monoethanolamide, lauric diethanolamide, myristic monoethanolamide, myristic diethanolamide, coco monoethanolamide, coco diethanol-amide, palmitic monoethanolamide, linoleic monoethanolamide, linoleic diethanolamide, hydroxystearyl monoethanolamide, almond diethanolamide, palm kernel diethanolamide, oleic monoethanoamide and mixtures thereof. Most highly preferred auxiliary thickening agent useful in the present invention include are lauric monoethanolamide (lauramide MEA), lauric diethanolamide (lauramide DEA), coco monoethanolamide (cocoamide MEA) and coco diethanol-amide (cocoamide DEA) which may be present from about 0% to about 10%, preferably at about 0% to about 8%, even more preferably from about 0% to about 6% by weight of the composition.

Examples of hair styling agents useful in the personal product compositions of the present invention include, but are not limited to styling polymers such as vinyl pyrrolidone/vinyl acetate copolymers (30/70 by weight), vinyl acetate homopolymer, t-butyl acrylate homopolymer, t-butyl sterene/ethyl hexyl methacrylate copolymer (50/50 by weight), dimethylacrylamide/t-butylacrylate/ethylhexyl methacrylate copolymer (10/45/45 by weight), ethylene/vinyl acetate copolymer (12.5/87.5 by weight), allyl alcohol/styrene copolymer (19/81 by weight), vinyl chloride/vinyl acetate copolymer (83/17 by weight and lower), vinyl pyrrolidone/vinyl acetate/butyl acrylate copolymer (10/78/12 and 10/70/20 by weight), vinyl pyrrolidone/vinyl acetate/butyl acrylate/styrene sulfonate copolymer (10/70/15/5 by weight), vinyl pyrrolidone/vinyl propionate copolymer (5/95 by weight), vinyl caprolactam/vinyl acetate copolymer (5/95 by weight), ethyl acrylate/acrylic acid/t-butyl acrylamide copolymer, vinyl acetate/crotonic acid copolymer (90/10 by weight), vinyl acetate/vinyl propionate/crotonic acid (50/40/10 by weight) and vinyl acetate/vinyl neodecanoate/crotonic acid copolymer. Typical levels of hair styling agent which are designed to assist the user in having the shampooed hair retain a particular shape are from about 0% to about 10% by weight of the composition.

Examples of organic viscosity control agents useful in the personal product and detergent compositions of the present invention include, but are not limited to $C_8$–$C_{18}$ alkyl fatty alcohols, $C_8$–$C_{18}$ alkyl fatty acids, $C_8$–$C_{18}$ alkyl fatty esters, ethanol, isopropanol and benzyl alcohol. Examples of inorganic viscosity modifying agents include ionizable salts such as sodium chloride, potassium chloride, calcium chloride, magnesium chloride and the like. The ionizable salts are particularly useful for obtaining or modifying a desired viscosity. The amount of ionizable salt used depends on the amount of active ingredient present and can be adjusted according to the formulators desires. Typical levels of salt used to control composition viscosity are from about 0.1% to about 10% by weight of the composition.

Examples of emulsifiers/emollients (refattying agents) or dispersants useful in the personal product and detergent compositions of the present invention include, but are not limited to dimethicone, cyclomethicone, lanolin oil, lanolin fatty acid, lanolin alcohol, acetylated lanolin alcohol, acetylated alkoxylated lanolin such as laneth-9 acetate and laneth-10 acetate, alkoxylated lanolin having about 30 to about 75 moles of ethylene oxide or propylene oxide such as PEG-16 lanolin, PEG-27 lanolin, PEG-40 lanolin, PEG-75 lanolin and PPG-12-PEG-50 lanolin, long chain esters such as cetyl acetate, stearyl acetate, oleyl acetate, lauryl lactate, myristyl lactate, cetyl lactate, stearyl lactate, decyl neopentanoate, decyl oleate, isopropyl myristate, lauryl myristate, myristyl myristate, myreth-3-myristate, palmityl myristate, stearyl myristate, isopropyl palmitate, octyl palmitate, 2-ethylhexyl palmitate, lauryl palmitate, myristyl palmitate, palmityl palmitate, stearyl palmitate, butyl stearate, myristyl stearate, palmityl stearate, isocetyl stearate, isostearyl isostearate, myristyl alcohol, cetyl alcohol, isocetyl alcohol, stearyl alcohol, oleyl alcohol, dioctyl succinate, didecyl succinate, caprylic/capric triglycerides, ethoxylated cholesterol, PEG-16 soya sterol, and mixtures thereof. Typical levels of emulsifier or emollient are from about 0% to about 10% by weight of the composition.

Examples of conditioning emollient oils useful in the personal product compositions of the present invention include, but are not limited to arnica blossom oil, apricot kernel oil, avocado oil, babassa oil, balm mint oil, basil oil, bergamot oil, bitter almond oil, bitter orange oil, castor oil, calendula oil, coconut oil, collagen/lanolin oil, cod liver oil, cucumber oil, corn oil, carrot oil, egg oil, eucalyptus oil, evening primrose oil, geranium oil, gardenia oil, grapefruit oil, grape seed oil, hybrid safflower oil, jasmine oil, jojoba oil, kiwi oil, light mineral oil, lemon oil, mandarin orange oil, orange flower oil, orange oil, mink oil, olive oil, palm oil, peach kernel oil, passionflower oil, rapeseed oil, sesame oil, soybean oil, safflower oil, sunflower oil, sweet almond oil, wheat germ oil and mixtures thereof. Typical levels of conditioning emollient oil are from about 0% to about 10% by weight of the composition.

Examples of conditioning extracts useful in the personal product compositions of the present invention include, but are not limited to aloe extract, aloe flower extract, aloe vera gel extract, balsam canada extract, balsam oregon extract, balsam peru extract, balsam tolu extract, honey extract and the like. Typical levels of conditioning extract are from about 0% to about 10% by weight of the composition.

Examples of humectants useful in the personal product compositions of the present invention include, but are not limited to propylene glycol (PG), butylene glycol, hexylene glycol, PEG (polyethylene glycol), PEG-5M, PEG-6, PEG-9, PEG-10, PEG-14M, PPG-12-buteth-16, PPG-12-buteth-16, PPG-28-buteth-35, glycerol (glycerin), erythritol, xylitol, sorbitol, mannitol, lactitol, hydrogenated starch hydrolyzates, sodium pyrrolidone carboxylic acid (sodium PCA), ethoxylated/propoxylated methyl glucose, lactic acid, acetamide MEA, lactamide MEA, wheat germamidopropyldimethyl lactate, $C_{12}$–$C_{15}$ lactate, stearamidopropyldimethyl lactate and mixtures thereof. Preferred humectants are propylene glycol, glycerol, hydrogenated starch hydrolyzates acetamide MEA, lactamide MEA and sodium pyrrolidone carboxylic acid. Typical levels of humectant are from about 0% to about 10% by weight of the composition.

Examples of solubilizing or clarifying agents useful in the personal product and detergent compositions of the present invention include, but are not limited to methanol, ethanol, propanol, isopropanol, butanol and the like. Typical levels of solubilizing or clarifying agent are from about 0% to about 10% by weight of the composition.

Examples of sunscreens or UV absorbers useful in the personal product and detergent compositions of the present invention include, but are not limited to dipropyleneglycol salicylate, octyl salicylate, 2-ethylhexyl p-dimethylaminobenzoate (octyidimethyl PABA), polyoxyethylene p-dimethylaminobenzoate (PEG-25 PABA), Tri-PABA-panthenol, dromtrizole, 2-ethylhexyl p-methoxycinnamate, DEA p-methoxycinnamate, butyl methoxybenzoylmethane, benzophenones 1 through 12 and the like. Preferred sunscreens are the benzophenones 1 through 6, 8, 9 and 11. Typical levels of sunscreen or UV absorber are from about 0% to about 8% by weight of the composition.

Examples of opacifiers and pearlescent agents useful in the personal product and detergent compositions of the present invention include, but are not limited to hexadecanol, octadecanol, tallow alcohol, oleyl alcohol, ethylene glycol monostearate, ethylene glycol distearate, diethylene glycol distearate, triethylene glycol distearate, glycerol mono/distearate, PEG 400 stearate, PEG 600 oleate, PEG-4 to PEG 150 laurate/dilaurate, PEG 4 to PEG 150 stearate/distearate, PEG-4 to PEG 150 oleate/dioleate, coco gluconamide, tallow gluconamide, dodecyl gluconamide hexadecyl gluconamide, octadecyl gluconamide, coco glucoheptonamide, tallow lactobionamide, octadecyl lactobionamide, tallow maltobionamide, bismuthoxychloride, spermaceti, magnesium silicate, calcium silicate, guanine, zinc oxide, titanium dioxide (anatose form or rutile form), titanium dioxide coated mica and coloured pigments coated mica and as well as the zinc, calcium and magnesium salts of fatty acids such as myristic acid, palmitic acid, stearic acid, behenic acid, coconut fatty acid. Preferred are the nonheteroatom containing alkyl aldonamides/aldobionamides and the ethylene glycol esters such as ethylene glycol monostearate and distearate. Typical levels of opacifiers or pearlescent agent are from about 0% to about 7% by weight of the composition.

Examples of vitamins useful in the personal product compositions of the present invention include, but are not limited to vitamin A, provitamin A, vitamin $B_1$, vitamin $B_2$, provitamin $B_5$, vitamin $B_6$, vitamin $B_{12}$, vitamin E and the like. Typical levels of vitamin are from about 0% to about 7% by weight of the composition.

Examples of amino acids useful in the personal product compositions of the present invention include, but are not limited to alanine, β-alanine, N-methylalanine, N-phenylalanine, α-aminoisobutyric acid, α-aminobutyric acid, α-aminocaproic acid, ε-aminocaproic acid, glycine, N-ethylglycine, N-propylglycine, N-butylglycine, leucine, methionine, derivatives of methionine, sarcosine, serine, norvaline, tryptophan, lysine, aspartic acid, glutamic acid, iminodiacetic acid, keratin amino acids (keratin polypeptides), silk amino acids, allantoin acetyl methionine, allantoin, deoxyribonucleic acid, protamine/nucleic acid complex, nucleic acid and mixtures thereof. Preferred amino acids are glycine, methionine, sarcosine, keratin amino acids and silk amino acids. Typical levels of amino acid are from about 0% to about 7% by weight of the composition.

Examples of proteins useful in the personal product and detergent compositions of the present invention include, but are not limited to hydrolyzed casein, hydrolyzed collagen (hydrolyzed animal protein), myristoyl hydrolyzed animal protein, hydrolyzed corn protein, hydrolyzed glycosaminoglycans, hydrolyzed keratin (keratin protein), hydrolyzed milk protein, hydrolyzed pea protein, hydrolyzed potato protein, hydrolyzed rice protein, hydrolyzed silk (silk protein), hydrolyzed soy protein, hydrolyzed vegetable protein, hydrolyzed wheat gluten, hydrolyzed wheat protein, hydrolyzed yeast protein and mixtures thereof. Preferred proteins are hydrolyzed collagen, hydrolyzed keratin protein, hydrolyzed silk protein and hydrolyzed soy protein. Typical levels of protein are from about 0% to about 7% by weight of the composition.

Examples of curl enhancing agents useful in the personal product compositions of the present invention include, but are not limited to sodium, potassium, ammonium and alkanolammonium salts of thioglycolic acid, dithiodiglycolic acid, mercaptobutane sulfonic acid, thiolactic acid, thioparaconic acid, α,α'-dimercaptoadipic acid, formamidine sulfonic acid, β-mercaptoethane sulfonic acid as well as mercaptans such as α-thiolglycerol, β-aminoethylmercaptan, mercaptoethyl alcohol, β-mercaptopionamide, mercaptoethylacetamide, thioglycolamide, methyl mercaptoethyl sulfone, mercaptoethyl nitrile, mercaptoethyl trifluoroacetamide-1,4-dimercapto-2,3-butanediol, cysteine, sulfite, bisulfite and the like. Further examples of curling agents are described in British Patent Nos. 0,771,627, 0,804,077, and 0,824,426; German Patent Nos. 0,971,899, 1,067,566 and 1,096,551; French Patent No. 1,174,561; Austrian Patent No. 0,210,071 and U.S. Pat. No. 3,148,126 all of which are incorporated herein by reference. Preferred curl enhancing agents are the sodium, potassium, ammonium salts of thioglycolic acid, sulfite, bisulfite and mixtures thereof. Typical levels of curl enhancing agent are from about 0% to about 7% by weight of the composition.

Examples of hair coloring agents useful in the personal product compositions of the present invention include, but are not limited to the temporary, semi-permanent or permanent organic, plant and metallic hair dyes. Examples of organic hair dyes include brilliant blue FCF, indigotine IA and the like. Typical levels hair coloring agent used in coloring shampoo preparations of the invention are from about 0% to about 7% by weight of the composition.

Examples of chelating or sequestering agents useful in the personal product and detergent compositions of the present invention include, but are not limited to the sodium, potassium and ammonium salts of diphosphoric acid, triphosphoric acid, pyrophosphoric acid, orthophosphoric acid, hexametaphosphoric acid, 1-hydroxyethane-1,1-phosphonic acid, diethylenetriamine penta(methylenediphosphonic acid), ethylenediaminetetraacetic acid (EDTA), diethylenetriaminepentaacetic acid (DTPA), N-(hydroxyethyl) ethylenediamine triacetic acid (HEDTA), propylenediamine tetraacetic acid (PDTA), nitrilotriacetic acid (NTA), mellitic acid, 1,2,3,4-cyclopentane tetracarboxylic acid, succinic acid, lauryl succinic acid, oxydisuccinic acid (ODS), carboxymethyloxysuccinic acid, citric acid, lactic acid, tartaric acid, O-carboxymethyltartronic acid, polyacrylic acid, poly (α-hydroxyacrylic acid), poly(tetramethylene-1,2-dicarboxylic acid), poly(4-methoxytetramethylene-1,2-dicarboxylic acid), acrylic acid/maleic acid copolymer (polycarboxylate), acrylic acid/allyl alcohol copolymer (polycarboxylate), sodium PCA, gluconic acid, glucoheptonic acid, lactobionic acid, maltobionic acid, ethylenediaminedisuccinic acid (EDDS) and mixtures thereof. Preferred are the sodium, potassium and ammonium salts of ethylenediaminetetraacetic acid, diethylenetriamine pentaacetic acid and ethylenediaminedisuccinic acid. Typical levels of chelating or sequestering agent useful for complexing hard ions such as calcium and magnesium are from about 0% to about 6% by weight of the composition.

Examples of hydrotropes useful in the personal product and detergent compositions of the present invention include, but are not limited to the sodium, potassium and ammonium salts of toluenesulfonic acid, ethyl-benzenesulfonic acid, xylenesulfonic acid, cumenesulfonic acid, urea, and mixtures thereof. Preferred are the sodium, potassium and ammonium salts of toluenesulfonic acid and xylenesulfonic acid. Typical levels of hydrotrope useful in maintaining hair care composition clarity are from about 0% to about 6% by weight of the composition.

Examples of anti-lice agents useful in the personal product compositions of the present invention include, but are not limited to lindane (gamma-benzene hexachloride), piperonyl butoxide, natural pyrethrins and synthetic pyrethroids. Typical levels of anti-lice agent are from about 0% to about 5% by weight of the composition.

Examples of hair straighteners useful in the personal product compositions of the present invention include, but are not limited to fats, oils, waxes, arachidyl alcohol, behenyl alcohol, polyvinylpyrrolidones, thioglycolates, mercaptans, sulfites and silicones. Preferred are waxes such as polyethylene homopolymer waxes, microcrystalline wax, oxidized microcrystalline wax, low and high density oxidized waxes, castorwax, chemically modified waxes, spermaceti wax, beeswax, paraffin wax, petroleum wax, carnauba wax, candelilla wax, ozokerite wax, ceresine wax, glyceride wax and mixtures thereof. Typical levels of hair straighteners are from about 0% to about 5% by weight of the composition.

Examples of preservatives or antimicrobial agents useful in the personal product and detergent compositions of the present invention include, but are not limited to glutaraldehyde, glyoxal, benzoic acid, salicylic acid, sorbic acid, dehydroacetic acid, benzyl alcohol, ethanol, methyl paraben, propyl paraben, butyl paraben, benzyl paraben, imidazolidinyl urea, diazolidinyl urea, monomethylol dimethyl hydantoin (MDM hydantoin), dimethylol dimethyl hydantoin (DMDM hydantoin), iodopropylnyl butylcarbamate, 2-octyl-4-isothiazolin-3-one, 5-chloro-2-methyl-4-isothia-zolin-3-one (methylchloroisothiazoline), 2-methyl-4-isothiazolin-3-one (methylisothaizoline) and the like. Preferred is a combination of methyl isothiazoline and chloromethyl isothiazoline as described in U.S. Pat. No. 4,265,899 sold under the trade name Kathon CG by Rohm and Haas Company which is incorporated herein by reference. Typical levels of preservative used to control bacterial or fungal action are from about 0.001% to about 4% by weight of the composition.

Examples of antioxidants useful in the personal product and detergent compositions of the present invention include, but are not limited to vitamin E (tocopherol), lecithin, wheat germ oil, sodium sulfite, sodium bisulfite, uric acid, propyl gallate, butylated hydroxyanisole (BHA), toluhydroquinone (THQ) sold as Tenox PG, Tenox BHA and Tenox THQ by Eastman Chemical Products Inc., and butylated hydroxytoluene (BHT) sold as Sustane BHT by UOP Process Division. Typical levels of antioxidant used to prevent oxidation, are from about 0% to about 4% by weight of the composition.

Examples of pH-control agents useful in the personal product and detergent compositions of the present invention include, but are not limited to citric acid, tartaric acid, lactic acid, gluconic acid, lactobionic acid, glycolic acid, propionic acid, succinic acid, maleic acid, hydrochloric acid, phosphoric acid, nitric acid, sulfuric acid, formic acid, boric acid, acetic acid, benzoic acid, methylsulfonic acid, ethylsulfonic acid, palmitic acid, stearic acid, hexadecylamine, octadecylamine, dimethylstearylamine, stearylamidopropyidimethyl amine, sodium hydroxide, sodium carbonate, potassium hydroxide and mixtures thereof. The amount of pH-control agent used will be that which is sufficient to provide the desired pH.

Examples of buffering agents useful in the personal product and detergent compositions of the present invention include, but are not limited to mixtures of weak acids (or their salts) and weak bases (or their salts) such as citric acid/disodium phosphate, citric acid/sodium citrate, acetic acid/sodium acetate and citric acid/borax (sodium tetraborate). The composition of the salt pair is highly variable and one skilled in the art can with simple experimentation arrive at various salt pairs that will be functional and that will not detract from the overall compositions. The pH of the present compositions may be in the range of about 5 to about 9, preferably from about 5.5 to about 8.5, even more preferably from about 6 to about 8. In practice however, a shampoo composition or conditioning shampoo composition is adjusted to a pH of about less than 7 to provide a composition that is non-irritating and non-damaging to the hair, skin and eyes of the consumer. The amount of buffering agent used will be that which is sufficient to provide the desired buffered pH.

Examples of colorants useful in the personal product and detergent compositions of the present invention include, but are not limited to D&C blue #1, D&C blue #4, D&C brown #1, D&C green #5 through #8, D&C orange #4 through #11 and the like. Typical levels of colorant are from about 0% to about 2% by weight of the composition.

Various materials have been taught in the art for use as agents that condition the skin. In general, such conditioning agents are designed to make the skin feel soft, smooth, silky and moisturized.

The term moisturizer is often used synonymously with the term emollient, and is meant to describe a material which imparts a soft, smooth, silky and moisturized feeling to the skin surface.

One way of moisturizing is to reduce the rate of water loss from the stratum corneum (skin surface) by depositing an occlusive material (emollient or emulsifier) on the skin surface which prevents water evaporation. Another technique is to add hygroscopic nonocclusive substances (humectants), which will retain water to the stratum corneum, making water available to the skin surface thereby producing the desired cosmetic effect. Nonocclusive moisturizers also function by improving the lubricity of the skin. Both occlusive and nonocclusive moisterizers as well as mixtures thereof are operative in the present invention. Examples of occulusive moisturizers (emollients or emulsifiers) include, lanolin and its derivatives, long chain esters, waxes, saturated and unsaturated fatty alcohols, conditioning oils and extracts, phospholipids, sterols, ceramides and silicones. Examples nonocculusive moisturizers (humectants) include polyols, fatty acids, certain alkanolamides, pyrrolidone carboxylic acid and their derivatives. It is to be understood that any such skin conditioning agent or mixtures thereof can be employed herein, depending on the formulations desires.

Examples of lanolin derivatives useful in the personal product useful in the personal product and detergent compositions of the present invention include, but are not limited to compositions of the present invention include, but are not limited to lanolin, lanolin oil, lanolin fatty acid, sodium lanolate and the like.

Examples of long chain esters useful in the personal product and detergent compositions of the present invention include, but are not limited to cetyl acetate, stearyl acetate, oleyl acetate and the like.

Examples of waxes useful in the personal product and detergent compositions of the present invention include, but are not limited to beeswax, white beeswax, polyoxyethylene sorbitol beeswax, paraffin wax, ceresin wax and the like.

Examples of saturated and unsaturated fatty alcohols useful in the personal product and detergent compositions of the present invention include, but are not limited to carbitol, lauryl alcohol, myristyl alcohol, cetyl alcohol, isocetyl alcohol, stearyl alcohol and the like.

Suitable phospholipids are exemplified as complex fat soluble substances that contain in their molecule, in addition to fatty acids and glycerol, a nitrgenous base such as choline or ethanolamine, two long alkyl chains having about 10 to about 18 carbon atoms and phosphoric acid. These compounds are found universally in living cells and are either completely absent or present in low concentrations in surface lipids. Specific examples of phospholipids useful in the present invention include, but are not limited to lecithin, cephalin (phosphatidylethanolamine), phosphatidylinositol and the like.

Examples of sterols useful in the personal product and detergent compositions of the present invention include, but are not limited to cholesterol, ethoxylated cholesterol, propoxylated cholesterol, cholesteryl acetate, cholesteryl benzoate, cholesteryl heptanoate, cholesteryl octanoate, cholesteryl nonanoate, cholesteryl palmitate, cholesteryl stearate, cholesteryl oleate, cholesteryl linoleate, cholesteryl oleyl carbonate, cholesteryl hydrocinnamate, cholesteryl chloride, 7-dehydrocholesterol, lumisterol, tachysterol, pyrocalciferol, lanosterol, lathosterol, ergosterol, stigmasterol, sitosterol, asterosterol, PEG-25 soya sterol and the like.

Examples of ceramides (sphingolipides) useful in the personal product and detergent compositions of the present invention include, but are not limited to those disclosed in EP Application Nos. 0,556,957, 0,227,994, 0,282,816 and 0,097,059, JP-A-63-192,703, U.S. Pat. Nos. 4,778,823, 4,985,546, 5,175,321, 5,198,210 and 5,206,020 and J. Soc. Cosmet. Chem. 40, 273–285 (1989) all of which are incorporated herein by reference.

Suitable non-volatile silicone fluids are exemplified as polyalkylsiloxane, polyarylsiloxane, polyalkylarylsiloxane and polyethersiloxane copolymers. Mixtures of these fluids may also be used and are preferred in certain executions. The silicone fluid should be insoluble in the personal product matrix and present as a dispersion.

Examples of polyols useful in the personal product and detergent compositions of the present invention include, but are not limited to propylene glycol, propylene glycol stearate, propylene glycol dipelargonate, PEG-55 propylene glycol oleate, PEG-75, PEG-150, PEG-400, PPG-5 ceteth-20, ethylene glycol monostearate, ethylene glycol distearate, PEG-6 stearate, PEG-8 distearate, PEG-25 stearate, PEG-100 stearate, PEG-150 distearate, PEG-400 stearate, glycerin, diglycerin, decaglyceryl diisostearate, glyceryl laurate, glyceryl myristate, PEG-26 glycerate, caprylic/capric triglyceride, pentaerythrityl tetralaurate, sorbitan stearate, glycereth-7 and the like.

Examples of fatty acids useful in the personal product and detergent compositions of the present invention include, but are not limited to pelargonic acid, lauric acid, myristic acid, palmitic acid, stearic acid, stearic acid (xxx), isostearic acid, hydroxystearic acid, oleic acid, linoleic acid, ricinoleic acid, arachidic acid, behenic acid, erucic acid, coconut fatty acid, soya fatty acid, tallow fatty acid, tall oil fatty acid, castor fatty acid, corn fatty acid, cottonseed fatty acid, palm fatty acid, rapeseed fatty acid, safflower fatty acid, sesame fatty acid, sunflower fatty acid and the like.

Examples of hygroscopic alkanolamides useful in the personal product and detergent compositions of the present invention include, but are not limited to acetamide MEA, acetamide DEA, lactamide MEA, lactamide DEA, lactaglucamide, lactamethylglucamide and the like. Example of pyrrolidone carboxylic acids useful in the present invention include but are not limited to sodium, potassium, ammonium and alkanol ammonium salts of pyrrolidone carboxylic acid, ethyl pyrrolidone carboxylic acid and the like. Typical levels of skin conditioning agent are from about 1% to about 40%, preferably from about 2% to about 30%, even more preferably from about 3% to about 25% by weight of the composition.

Examples of skin feel mildness agents useful in the personal product and detergent compositions of the present invention include, but are not limited to the cationic, anionic, amphoteric and nonionic polymers used in the cosmetic field.

Examples of cationic and ronionic polymers useful in the personal product and detergent compositions of the present invention include, but are not limited to Polymer JR-400 sold by Union Carbide, Merquat 100 and 550 sold by Merck and Company Inc., Jaguar C14-S and Jaguar HP-60 sold by Stein Hall, Mirapol A15 sold by Miranol Chemical Company Inc., Galactasol 811 sold by Henkel Inc. and Stalok 300 and 400 sold by Staley Inc., as well as hydroxypropyl gaur gum, carboxymethyl cellulose, hydroxyethyl cellulose, sodium isethionate, acrylates/octylpropenamide copolymer, copolymers of dimethylaminoethyl-methacrylate and acrylamide, copolymers of dimethyldiallylammonium chloride and acrylamide and the like. A more complete list of cationic polymers useful in the present invention is discribed in U.S. Pat. No. 4,438,095 which is incorporated herein by reference. Typical levels of skin conditioning agent are from about 0% to about 5%, preferably from about 0% to about 4%, even more preferably from about 0% to about 3% by weight of the composition.

Examples of hydroxy acids useful in the personal product and detergent compositions of the present invention include, but are not limited to the α-hydroxy acids (2-hydroxy acids). Specific examples of α-hydroxy acids include, but are not limited glycolic acid (hydroxyacetic acid), DL-lactic acid (2-hydroxypropionic acid), D-lactic acid, L-lactic acid and the like. Other examples of hydroxy acids useful in the present invention include the β-Hydroxy acids (3-hydroxy acids) such as 3-hydroxypropionic acid, 3-hydroxybutyric acid, 3-hydroxycaproic acid and the like. Still other examples of hydroxy acids useful in the present invention include the γ-hydroxy acids (4-hydroxy acids), δ-hydroxy acids (5-hydroxy acids), aldonic acids, aldoheptonic acids, aldobionic acids, mevalonic acid and thier lactones as well as the hydroxydicarboxylic acids such as maleic acid, malic acid and the like. The natural and synthetic fruit acids such as glycolic acid (from sugar cane or sugar beet or by reaction of formaldehyde with carbon monoxide), malic acid (from apples and grapes or from maleic anhydride and water), lactic acid (from sour milk or by fermentation of corn or sugar substrates) and citric acid (from fruits and vegetables or by fermentation of corn or sugar substrates) and the like are useful as well. Typical levels of skin conditioning agent are from about 0% to about 10%, preferably from about 0% to about 8%, even more preferably from about 0% to about 6% by weight of the composition.

Examples of antiperspirant/deodorant agents useful in the personal product compositions of the present invention include, but are not limited to the well known antiperspirant metal salts of aluminum, zinc, zirconium and zirconium aluminum mixtures of sulfates, chlorides, chlorohydroxides, tetrachlorohydrex glycinates, alums, formates, lactates, benzyl sulfonates, succinates, phenol sulfonates and the like. Typical levels of antiperspirant/deodorant agent are from about 0% to about 35%, preferably from about 0% to about 25% by weight of the composition. The composition may further include a complexing agent such as an organic acid or derivative thereof that are capable of forming complexes with the antiperspirant metallic salt. Examples of such complexing agents include, but are not limited to acetic acid, propionic acid, oxalic acid, malonic acid, succinic acid, tartaric acid, glycine and the like together with their cosmetically acceptable salts. Typical levels of complexing agent are from about 0% to about 15%, preferably from about 0% to about 10%, by weight of the composition.

Examples of a hardening agent useful in the personal product compositions of the present invention include, but are not limited to lower alkanol amines, diamines and amides wherein such materials comprise at least tvo lower alkanol groups, preferably from about two to about four lower alkanol groups having from about 2 to about 4 carbon atoms. Examples of such hardening agents include, but are not limited to tetrahydroxyalkyldiamine compounds such as tetrahydroxypropylethylenediamine, polyoxamine compounds such as polyoxyethylene, polyoxypropylene block copolymers of ethylenediamine and alkanolamide compounds such as coconut diethanolamide and lauryl monoethanolamide. Typical levels of harding agent are from about 0% to about 5% by weight of the composition.

Examples of heeling agents useful in the personal product and detergent compositions of the present invention include, but are not limited to allantion, aluminum dihydroxy allantoinate, urea, uric acid, aloe vera gel, methyl manuronate, uronic acids, sucrose octaacetate, menthol, hydrolyzed elastin, sodium hyaluronate, mucopolysacharides, chitosans, sodium alginate and mixtures thereof. Typical levels of heeling agent are from about 0% to about 6% by weight of the composition.

Examples of astringents which are intended to precipitate salivary proteins and mucous secretions (thereby function as anti-plaque and anti-calculus agents) as well as shrink and protect inflamed mucous secretions useful in the personal product compositions of the present invention include, but are not limited to zinc chloride, zinc phosphate, zinc acetate, zinc aspartate, zinc acetylmethionate, zinc citrate trihydrate, zinc tannate, zinc gluconate, zinc lactobionate, zinc maltobionate, zinc hydrolyzed collagen, zinc pyrrolidone carboxylic acid (zinc PCA), zinc tribromosalicylanilide, zinc caprylate, zinc octoate, zinc laurate, zinc myristate, zinc stearate, zinc oleate, zinc carbonate, zinc borate, zinc silicate, zinc sulfide, zinc sulfate, zinc oxide, zinc phenol sulfonate, zinc stannate, zinc dl-lactate, trihydrate, zinc cocoate, tannic acid, citric acid, acetic acid, lactic acid and mixtures thereof. Additional zinc salts that are useful as anti-plaque and anti-calculus agents are disclosed in U.S. Pat. Nos. 4,100,269, 4,416,867, 4,425,325 and 4,339,432 all of which are incorporated herein by reference. Furthermore, it is well known that dental plaque could also be removed with a variety of other heavy metal salts besides zinc, such as copper and nickel. Preferred astringents that function as anti-plaque and anti-calculus agents are zinc chloride and zinc citrate trihydrate. Typical levels of astringent that also function as anti-plaque and/or anti-calculus agents are from about 0% to about 8% by weight of the composition.

Examples of additional noi-astringent anti-plaque and/or anti-calculus agents include anionic polymers such as carboxylate polymers (PVM/PM copolymer), sulfonate polymers, carboxylate/sulfonate polymers, carboxylate/phosphonate polymers and mixtures thereof as described in U.S. Pat. Nos. 3,429,963, 3,956,180, 3,956,480, 4,138,477, 4,152,420, 4,183,914, 4,254,101, 4,808,400, and 5,011,682 all of which are incorporated herein by reference. Preferred non-astringent anti-plaque and/or anti-calculus agents are the carboxylate polymers particularly the carboxyvinyl polymers (polyacrylic acid copolymers) sold under the trade name carbopol by BF Goodrich Company. Typical levels of anionic polymer are from about 0% to about 8% by weight of the composition. Still, further examples of addition non-astringent anti-plaque and/or anti-calculus agents include the soluble pyrophosphate salts such as sodium trihydrogen pyrophosphate, disodium dihydrogen pyrophosphate, trisodium hydrogen pyrophosphate, trisodium hydrogen pyrophosphate monohydrate and the like. These compounds are more fully disclosed in U.S. Pat. Nos. 4,515,772, 4,515,772 and 4,627,977 all of which are incorporated herein by reference. Preferred soluble pyrophosphate salts are sodium trihydrogen pyrophosphate, disodium dihydrogen pyrophosphate, tetrasodium pyrophosphate, tetrapotassium pyrophosphate and mixtures thereof. Typical levels of soluble pyrophosphate salt are from about 0% to about 8% by weight of the composition.

Examples of antibacterial agents useful in the personal product compositions of the present invention include, but are not limited to thymol, anethole, eucalyptol, menthol, cetylpyridinium chloride, benzoic acid, sodium benzoate, boric acid, domiphen bromide and chlorhexidine gluconate and the like. Most highly preferred antibacterial agents are cetylpyridinium chloride, benzoic acid, sodium benzoate and domiphen bromide. Typical levels of antibacterial agent are from about 0% to about 5% by weight of the composition.

Examples of essential flavorant oils useful in the personal product compositions of the present invention include, but are not limited to peppermint, spearmint, wintergreen (as synthetic methyl salicylate) and the like. Typical levels of flavorant oil are from about 0.01% to about 4% by weight of the composition.

Examples of sweeteners useful in the personal product compositions of the present invention include, but are not limited to saccharin (as sodium, potassium or calcium saccharin), cyclamate (as sodium, potassium or calcium cyclamate), aspartame, acesulfane-K, thaumatin, neohisperidin dihydrochalcone, ammoniated glycyrrhizin, dextrose, levulose, sucrose, D-tryptophan, miraculin, nutrasweet, mannose, glucose, α-D-glucose, β-D-glucose, lactose, galactose and mixtures thereof. Both artificial and natural sweeteners may be used to add further sweetness than that provided by the essential flavoring oils. A preferred sweetener is the potassium or sodium salts of saccharin. Typical levels of sweetener are from about 0.01% to about 4% by weight of the composition.

Examples of fluorides useful in the personal product compositions of the present invention include, but are not limited to sodium fluoride, potassium fluoride, sodium monofluorophosphate, potassium monofluorophosphate, stannous fluoride and the like. Most highly preferred fluorides are sodium fluoride, sodium monofluorophosphate and mixtures thereof. Typical levels of fluoride are from about 0% to about 5% by weight of the composition.

Examples of desensitizing agents (antiinflammatory agents) useful in the personal product compositions of the present invention include, but are not limited to bisabolol, tribasic sodium citrate, dibasic sodium citrate, monobasic sodium citrate, sodium silicofluoride, potassium nitrate, sodium nitrate, silver nitrate, zinc nitrate, calcium nitrate, calcium hydroxide, strontium chloride hexahydrate, papain, formaldehyde, sodium fluoride, sodium monofluorophosphate and mixtures thereof. Preferred desensitizing agents are nitrate salts, strontium chloride, citrate salts, bisabolol and mixtures thereof. Most highly preferred desensitizing agents are sodium nitrate, potassium nitrate, calcium nitrate, strontium chloride hexahydrate and mixtures thereof. Typical levels of desensitizing agent are from about 0% to about 8% by weight of the composition.

Examples of antibiotics useful in the personal product compositions of the present invention include, but are not limited to penicillin, neomycin, erythromycin, tyrothricin, chlorotetraacycline, vancomycin, alexidine, octenidine and mixtures thereof. Preferred antibiotics are neomycin, alexidine and mixtures thereof. Typical levels of antibiotic are from about 0% to about 3% by weight of the composition.

Examples of antienzymes (enzyme inhibitors) useful in the personal product compositions of the present invention include, but are not limited to penicillin, anionic surfactants such as sodium N-lauroyl sarcosinate and sodium dodecylbenzenesulfonate, sodium dehydroacetate and mixtures thereof. Antienzymes prevent dental caries by inhibiting acid producing enzymes that convert sugars into acids which are corrosive to teeth. Typical levels of antienzyme are from about 0% to about 3% by weight of the composition.

Examples of bleaching agents useful in the detergent compositions of the present invention include, but are not limited to oxygen bleaches as well as other types of bleaching agents. For wash conditions below about 50° C., especially below about 40° C., it is sometimes preferred that the compositions herein do not contain borate or material which can form borate in situ under detergent storage or wash conditions. As used herein, when a detergent composition is "substantially free of borate and borate forming material" shall mean that the composition contains not more than about 2% by weight of borate containing and borate forming material of any type, preferably, no more than 1%, more preferably 0%. When a borate forming oxygen containing bleaching material is used, a preferred example is sodium perborate monohydrate and sodium perborate tetrahydrate.

One category of bleaching agent that can be used encompasses percarboxylic acid bleaching agents and salts thereof. Suitable examples of this class of agents include the sodium, potassium, ammonium or the magnesium salts of N,N'-terephthaloyidi(6-aminoperoxy)-caproic acid (TPCAP) and the like. Such bleaching agents are disclosed in U.S. Pat. No. 4,483,781, Hartman, issued Nov. 20, 1984, U.S. patent application Ser. No. 740,446, Burns et al., filed Jun. 3, 1985, European Patent Application 0,133,354, Banks et al., published Feb. 20, 1985, U.S. Pat. No. 4,412,934, Chung et al., issued Nov. 1, 1983 and European Patent Application 0,564,250, Coope et al., published Jun. 10, 1993, all of which are incorporated by reference herein. A sometimes highly preferred bleaching agent includes 6-nonylamino-6-oxoperoxycaproic acid as described in U.S. Pat. No. 4,634,551, issued Jan. 6, 1987 to Burns, et al., incorporated herein by reference.

Another category of bleaching agents that can be used encompasses the halogen bleaching agents. Examples of hypohalite bleaching agents include the sodium, potassium, ammonium, lithium, calcium or magnesium salts of hypochlorite, hypobromite, hypoiodite, trichloroisocyanuric acid, dichloroisocyanuric acid, chlorinated trisalt phosphate as well as chorine oxide solutions and N-chloro- or N-bromoalkane sulfonamides. Such materials are normally added from about 0.1% to about 10% by weight of the finished product, preferably from about 1% to about 5% by weight of the finished product.

Yet another category of bleaching agents that can be used include the peroxygen bleaching agents. Suitable peroxygen bleaching compounds include sodium carbonate peroxyhydrate (sodium percarbonate), sodium pyrophosphate peroxyhydrate, urea peroxyhydrate, sodium peroxide, sodium persulfate, potassium peroxomonosulfate and the like. Peroxygen bleaching agents are preferably combined with bleach activators, which lead to the in situ production in aqueous solution (i.e., during the washing process) of the peroxy acid corresponding to the bleach activator.

Preferred bleach activators (bleach activating agents) incorporated into compositions of the present invention have the general formula:

wherein R is an alkyl group containing from about 1 to about 18 carbon atoms wherein the longest linear alkyl chain extending from and including the carbonyl carbon contains from about 6 to about 10 carbon atoms and L is a leaving group, the conjugate acid of which has a $pK_a$ in the range of from about 4 to about 13. These bleach activators are described in U.S. Pat. No. 4,915,854, issued Apr. 10, 1990 to Mao, et al., incorporated herein by reference. Examples of bleach activators useful in the present invention include but are not limited to tetraacetyl ethylenediamine (TAED), pentaacetyl glucose (PAG), tetraacetyl glycoluril (TAGU), sodium nonanoyloxybenzene sulfonate (SNOBS), sodium isononanoyloxybenzene sulfonate (iso-SNOBS) and the like. In general, bleaching compounds are optional components in non-liquid formulations, such as granular detergents. Typical levels of bleach activator are about 0% to about 60%, preferably from about 0% to about 50%, even more preferably from about 0% to about 45%, most preferably at least 0.1% by weight of the comp-osition.

Another method of bleaching is generally known as catalytic activation which involves enhancing the bleaching activity of hydrogen peroxide. Examples of catalytic bleaching agents include certian heavy metal ions such as iron, molybdenum, tugsten, vanadium and the like.

Another example of a catalytic bleaching agent include the sulfonimines as described in U.S. Pat. No. 5,041,232 issued Aug. 20, 1991 and U.S. Pat. No. 5,047,163 issued on Sep. 10, 1991 to Batel et al. all of which are incorporated herein by reference. Typical levels of sulfonimine catalytic bleaching agent when used are from about 0.01% to about 12% by weight of the composition.

Yet another example of a catalytic bleaching agent include the mangenese catalyst bleaching complexes as described in European Patent Application No. 0,458,398, U.S. Pat. No. 5,244,594, U.S. Pat. No. 5,246,621, Great Britain Application No. 9027415.0, Great Britain Application No. 9115012.8, Great Britain Application No. 9124474.9, Great Britain Application No. 9124581.1, Great Britain Application No. 91203078.0, Great Britain Application No. 9127060.3, Great Britain Application No. 9108136.4, and in Nature Vol 369, pages 609–610 and 637–639, Jun. 23, 1994, to Hage et al. all of which are incorporated herein by reference. The mangenese catalyst bleaching complexes have the general structure:

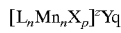

$[L_nMn_nX_p]^zY_q$ wherein L is a macrocyclic organic ligand such as triazacyclononane (TACN), N,N',N"-trimethyltriazacyclononane (Me-TACN), N,N',N"-trimethyltriazacyclododecane (Me-TACD) and the like; X is a small coordinating ion or bridging group; n and m are intergers from about 1 to about 4; p is an interger from about 0 to about 12; Y is a counterion; z is the complex charge; and q is defined as z/charge Y. Processes for the commercial manufacture of such catalysts are described in U.S. Pat. No. 5,153,161 issued on Oct. 6, 1992, U.S. Pat. No. 5,256,779 issued on Oct. 26, 1992 and U.S. Pat. No. 5,274,147 issued on Dec. 28, 1993 to Kerschner et al. all of which are incorporated herein by reference. Typical levels of mangenese catalyst bleaching complex when used are from about 0.001% to about 15% by weight of the composition.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalo-cyanine and a photoactivated bleaching process are described in U.S. Pat. No. 4,033,718, issued Jul. 5, 1977 to Holcombe et al., incorporated herein by reference. Typically detergent compositions can contain about 0% to about 1.3% by weight of sulfonated zinc phthalocyanine.

The detergent compositions hereof may contain a non-borate forming oxygen bleaching agent component. These bleaching agent components can include one or more oxygen bleaching agents and, depending upon the bleaching agent chosen, one or more bleach activators. Typical levels of bleaching agent are from about 0% to about 30%, preferably from about 0% to about 28%, even more preferably from about 0% to about 25%, most preferably at least 0.01% by Examples of builders useful in the detergent compositions of the present invention include, but are not limited to the alkali metal, ammonium, and alkanolammonium salts of polyphosphates, phosphates, phosphonates, silicates, aluminosilicates, carbonates, polycar-boxylates and sulfates. Borate builders, as well as builders containing borate-forming materials that can produce borate under detergent storage or wash conditions, can be used as well. Sometimes non-borate builders may be used in compositions of the invention intended for wash conditions less than about 50° C.

Examples of polyphosphate builders include the sodium, potassium, lithium and ammonium, mono-, di- and trialkanolammonium salts of pyrophosphonic acid, tripolyphosphonic acid, glassy polymeric metaphosphonic acid, phytic acid, orthophosphonic acid, polymetaphosphonic acid in which the degree of polymerization ranges from about 6 to about 21. Particularly preferred are the alkali metal tripoly- and pyrophosphates.

Examples of phosphate builders include sodium phosphate mono- basic, sodium phosphate monobasic monohydrate, sodium phosphate di-basic, sodium phosphate dibasic heptahydrate, sodium phosphate tribasic (STP), sodium phosphate tribasic dodecahydrate, diethylenetriamine pentamethylene phosphate as well as the corresponding potassium and lithium salts.

Examples of phosphonate builder salts include the water soluble salts of 1-hydroxy-ethane-1,1-diphosphonate, particularly the sodium and potassium salts, the water soluble salts of methylene diphosphonic acid, particularly the trisodium and tripotassium salts and the water soluble salts of substituted methylene diphosphonic acids, particularly the trisodium or tripotassium salts of ethylidene, isopyropylidene, benzylmethylidene and halomethylidene phosphonic acid and amino tris(methylene) phosphonic acid. Phosphonate builder salts of the aforementioned types are disclosed in U.S. Pat. Nos. 3,159,581 and 3,213,030 issued Dec. 1, 1964 and Oct. 19, 1965, to Diehl; U.S. Pat. No. 3,422,021 issued Jan. 14, 1969, to Roy; and U.S. Pat. Nos. 3,400,148 and 3,422,137 issued Sep. 3, 1968, and Jan. 14, 1969 to Quimby which are all incorporated herein by reference.

In general, phosphate and phosphonate builders may be added, however it is generally desirable to replace these materials with polycarboxylate builders as well as with other builders. Thus, if present they are preferably included only at low levels. Preferably, the phosphate builder comprises less than about 10% by weight, more preferably less than about 5%, most preferably essentially 0%, of total builder in the composition.

Examples of silicate builders include the alkali metal silicates, particularly those having a $SiO_2:Na_2O$ ratio in the range 1.6:1 to 3.2:1 and layered silicates such as the layered sodium silicates described in U.S. Pat. No. 4,664,839, issued May 12, 1987 to H. P. Rieck, incorporated herein by reference. However, other silicates may also be useful such as magnesium silicate, which can serve as a crispening agent in granular formulations, as a stabilizing agent for oxygen bleaches and as a component of suds control systems.

The aluminosilicate builders are especially useful in the present invention. Aluminosilicate builders are of great importance in most currently marketed heavy duty granular detergent compositions, and can also be a significant builder ingredient in liquid detergent formulations.

Examples of carbonate builders include the alkaline earth and alkali metal carbonates, such as sodium carbonate, sodium bicarbonate and sesquicarbonate and mixtures thereof with ultra-fine calcium carbonate as disclosed in German Patent Application No. 2,321,001 published on Nov. 15, 1973 which is incorporated herein by reference.

Examples of other organic detergent builders suitable for the purposes of the present invention include, but are not restricted to, a wide variety of polycarboxylate compounds. As used herein, "polycarboxylate" refers to compounds having several carboxylate groups, preferably at least three carboxylates.

Polycarboxylate builders can generally be added to the composition in acid form, but can also be added in the form of a neutralized salt. When utilized in salt form, alkali metals, such as sodium, potassium and lithium salts or ammonium and alkanolammonium salts are preferred.

Included among the polycarboxylate builders are a variety of categories of useful materials. One important category of polycarboxylate builders encompasses the ether polycarboxylates. A number of ether polycarboxylates have been disclosed for use as detergent builders. Examples of useful ether polycarboxylates include oxydisuccinate, as disclosed in U.S. Pat. No. 3,128,287, issued Apr. 7, 1964 to Berg, and in U.S. Pat. No. 3,635,830, issued Jan. 18, 1972 to Lamberti et al. both of which are incorporated herein by reference.

Suitable ether polycarboxylates also include cyclic compounds, particularly alicyclic compounds, such as those described in U.S. Pat. Nos. 3,923,679; 3,835,163; 4,158,635, 4,120,874 and 4,102,903, all of which are incorporated herein by reference.

Organic polycarboxylate builders also include the various alkali metal, ammonium and substituted ammonium polyacetates. Examples of polyacetate builders include the sodium, potassium, lithium, ammonium and substituted ammonium salts of ethylenediamine tetraacetic acid (EDTA), nitrilotriacetic acid (NTA) and N-(2-hydroxyethyl) iminodiacetic acid (HIDA).

Also included are polycarboxylates such as mellitic acid, tartaric acid, itaconic acid, succinic acid, maleic acid, polymaleic acid, benzene 1,3,5-tricarboxylic acid, 1,2,3,4-cyclopentane tetracarboxylic acid, cyclohexane hexacarboxylic acid, carboxymethyloxysuccinic acid (CMOS), carboxymethyloxymalonic acid, carboxymethyltartronic acid and as well as the corresponding alkyl metal, ammonium and alkanolammonium salts.

Citrate builders (citric acid and its soluble salts) is a polycarboxylate builder of particular importance for heavy duty liquid detergent formulations, but can also be used in granular compositions. Suitable salts include the metal salts such as the sodium, potassium and lithium salts as well as the organic salts such as ammonium and alkanolammonium salts.

Other carboxylate builders include the carboxylated carbohydrates disclosed in U.S. Pat. No. 3,723,322, to Diehl, issued Mar. 28, 1973, incorporated herein by reference.

Also suitable in the detergent compositions of the present invention are the 3,3-dicarboxy-4-oxa-1,6-hexanedioates (succinic acid builders) and the related compounds disclosed in U.S. Pat. No. 4,566,984, to Bush, issued Jan. 28, 1986, which is incorporated herein by reference. Laurylsuccinates are the preferred builders of this group and are described in European Patent Application 86200690.5/0,200,263, published Nov. 5, 1986.

Examples of useful builders also include the water soluble polyacrylates such as polyacrylic acid, poly(acrylic acid/ coallyl alcohol), poly(acrylic acid/comaleic acid), poly($\alpha$-hydroxy acrylic acid), poly(tetramethylene-1,2-dicarboxylic acid), poly(4-methoxytetramethylene-1,2-dicarboxylic acid) and the like. These polyacrylates generally having molecular weights to above 2,000 and can also be utilized as dispersants.

Other suitable polycarboxylates are the polyacetal carboxylates disclosed in U.S. Pat. No. 4,144,226, to Critchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups, (to stabilize the polyacetal carboxylate against rapid depolymerization in alkaline solution), converted to the corresponding salt and added to a surfactant.

Addition polycarboxylate builders are also disclosed in U.S. Pat. No. 3,308,067, to Diehl, issued Mar. 7, 1967, incorporated herein by reference. Such materials include the water soluble salts of homo- and copolymers of aliphatic carboxylic acids such as maleic acid, itaconic acid, mesaconic acid, fumaric acid, aconitic acid, citraconic acid and methylene-malonic acid.

Examples of sulfate builders include sodium sulfate, granular sodium sulfate, powdered sodium sulfate, sodium sulfate decahydrate as well as the corresponding potassium and lithium salts.

Other organic builders that are known in the art can also be used. For example, monocarboxylic acids (fatty acids), and soluble salts thereof having a long hydrocarbon chain comprising from about 8 to about 18 carbon atoms that may be saturated or unsaturated. These materials are sometimes referred to as soaps.

The level of builder can vary widely depending upon the end use of the composition and its desired physical form. Liquid formulations typically comprise from about 0% to about 50%, preferably about 0% to about 40% even more preferably from about 0% to about 35%, most preferably at least 0.5% by weight of the composition. Granular formulations typically comprise from about 0% to about 80%, preferably from about 0% to about 70%, even more preferably from about 0% to about 65%, most preferably at least 0.5% by weight of the composition. Lower or higher levels of builder, however, are not meant to be excluded.

A preferred builder system for powdered detergent compositions comprises a mixture of from about 5% to about 50% of zeolite (preferably Zeolite A) and/or layered silicate builder, and from about 5% to about 50% citrate (preferably sodium citrate), wherein the percentages are based upon the total builder in the mixture, calculated on a weight basis.

Examples of enzymes useful in the detergent compositions of the present invention include, but are not limited to proteases, amylases, cellulases, lipases and peroxidases as well as mixtures thereof. They may be of any suitable origin, such as vegetable, animal, bacterial, fungal and yeast origin. However, their choice is governed by several factors such as pH-activity and/or stability optima, thermostability, stability versus active detergents, builders and so on. In this respect bacterial or fungal enzymes are preferred, such as bacterial amylases and proteases and fungal cellulases. A wide range of enzyme materials and means for their incorporation into synthetic detergent granules is also disclosed in U.S. Pat. No. 3,553,139, issued Jan. 5, 1971 to McCarty et al. which is incorporated herein by reference. Enzymes are further disclosed in U.S. Pat. No. 4,101,457, Place et al., issued Jul. 18, 1978 and in U.S. Pat. No. 4,507,219, Hughes, issued Mar. 26, 1985, both of which are incorporated herein by reference. Enzyme materials useful for liquid detergent formulations, and their incorporation into such formulations, are disclosed in U.S. Pat. No. 4,261,868, Hora et al., issued Apr. 14, 1981 which is also incorporated herein by reference. Enzymes are normally incorporated at levels sufficient to provide up to about 5 mg by weight, more typically about 0.05 mg to about 3 mg of active enzyme per gram of the composition.

Typical levels of enzyme are about 0% to about 7%, preferably from about 0% to about 6%, even more preferably from about 0% to about 5%, most preferably at least 0.02% by weight of the composition.

Examples of enzyme stabilization systems useful in the detergent compositions of the present invention include, but are not limited to those for granular detergents, such as those enzymes which are preferably coated or prilled with additives inert toward the enzymes to improve storage stability. In liquid formulations, an enzyme stabilization system is preferably utilized. Enzyme stabilization techniques for aqueous detergent compositions are well known in the art. For example, one technique for enzyme stabilization in aqueous solutions involves -the use of free calcium ions from sources such as calcium acetate, calcium formate, calcium propionate and the like. Calcium ions can be used in combination with short chain carboxylic acid salts, preferably formates. See, for example, U.S. Pat. No. 4,318,818, Letton, et al., issued Mar. 9, 1982 which is incorporated herein by reference. If used, typical levels of calcium ion are from about 0.01 to about 50, preferably from about 0.1 to about 20 millimoles per liter.

Polyols such as glycerol, propylene glycol, ethylene glycol, sorbitol, mannitol, glucose and the like are also useful as enzyme stabilizers. If used, typical levels of polyol are from about 0.1% to about 15%, preferably from about 0.2% to about 9% by weight of the composition.

Also, propionic acid, propionic acid salts, boric acid, alkali metal borates, boric oxide, borax and the like are useful as enzyme stabilizers. If used, typical levels of propionic acid or propionic acid salts are from about 0.1% to about 15%, preferably from about 0.2% to about 9% by weight of the composition. If used, typical levels of boric acid are from about 0.2% to about 6%, preferably from about 0.3% to about 3% by weight of the composition.

One especially preferred enzyme stabilization system is a polyol in combination with boric acid. Preferably, the weight ratio of polyol to boric acid is at least about 1:1, more preferably at least about 1.3:1.

Furthermore, alkoxy alcohols, dialkylglycol ethers as well as mixtures of polyvalent alcohols with polyfunctional aliphatic amines such as the di-ethanolamine, triethanolamine, diisopropanolamine and the like are also useful as enzyme stabilizers. Enzyme stabilization techniques are additionally disclosed and exemplified in U.S. Pat. No. 4,261,868, issued Apr. 14, 1981 to Horn, et al., U.S. Pat. No. 3,600,319, issued Aug. 17, 1971 to Gedge, et al., both of which are incorporated herein by reference and European Patent Application No. 0,199,405, (86200586.5), published Oct. 29, 1986, Venegas which is incorporated herein by reference. Enzyme stabilization systems are also described, for example, in U.S. Pat. Nos. 4,261,868, 3,600,319, and 3,519,570 all of which are all incorporated herein by reference. In general, typical levels of an enzyme stabilization system are from about 0% to about 15%, preferably from about 0% to about 13%, even more preferably from about 0% to about 10%, most preferably at least 0.1% by weight of the composition.

Examples of optical brighereners useful in the detergent compositions of the present invention include, but are not limited to the numerous optical brightener/fluorescent whitening agent materials have been taught in the art. Such materials are designed to deposit onto fibers and fabrics and to alter the chromaticity of items to yield a more preferred white. Optical brighteners work by converting invisible ultraviolet radiation (290–400 nm) to a visible blue frequency. Therefore, optical brighteners can shift the chromaticity of the fabric surface away from a yellow cast to a preferred clean bluish cast. In general, such optical brightener molecules have at least one relatively large chromophoric group and one or more substituent groups. For use in laundry detergents, the molecules must not only exhibit the correct optical properties, but also must be capable of being deposited onto fabrics from an aqueous wash liquor containing various surfactants, detergency builders and other detersive adjuncts. The choice of optical brightener for use in detergent compositions will depend upon a number of factors, such as the type of detergent, the nature of other components present in the detergent composition, the temperature of the wash water, the degree of agitation and the ratio of the material washed to the tub size. The brightener selection is also dependent upon the type of material to be cleaned, e.g., cottons, synthetics, etc. Since most laundry detergent products are used to clean a variety of fabrics, the detergent compositions should contain a mixture of brighteners which are effective for a variety of fabrics. It is of course necessary that the individual components of such a brightener mixture be compatible. Commercial optical brighteners which may be useful in the present invention can be classified into subgroups which include, but are not limited to, derivatives of stilbene, pyrazoline, coumarin, cinnamic, carboxylic acid, methinecyanine, dibenzothiophene-5,5-dioxide, azole, 5- and 6-membered ring heterocycles and other optional agents. Examples of these types of brighteners are disclosed in "The Production and Application of Fluorescent Brightening Agents", M. Zahradnik, published by John Wiley & Sons, New York (1982) which is incorporated herein by reference.

Stilbene derivatives which may be useful in the present invention include, but are not limited to, derivatives of bis(triazinyl)aminostilbene; bisacylamino derivatives of stilbene; triazole derivatives of stilbene; oxadiazole derivatives of stilbene; triazole derivatives of stilbene; oxazole derivatives of stilbene; and styryl derivatives of stilbene.

Examples of stilbene derivatives which may be useful as optical brighteners in the present invention can be found under the heading "Brighteners, Optical", in The Kirk-Othmer Encyclopedia of Chemical Technology, Volume 3, pp. 737–750, (John Wiley & Sons Inc., 1962) which is incorporated herein by reference.

Examples of pyrazoline derivatives which may be useful in the present invention include, but are not necessarily limited to, those disclosed on pages 59–62 of the Zahradnik reference.

Coumarin derivatives which may be useful in the present invention include, but are not limited to, derivatives substituted in the 3-position, in the 7-position and in both the 3- and 7-positions. Examples of such coumarin derivatives include, but are not limited to, those disclosed on pages 63–71 of the Zahradnik reference. Other examples of coumarin derivatives which may be useful in the present invention are those disclosed on pages 744–745 of the Zahradnik reference.

Carboxylic acid derivatives which may be useful as optical brighteners in the present invention include, but are not limited to, fumaric acid derivatives; benzoic acid derivatives; p-phenylene bisacrylic acid derivatives; naphthalene dicarboxylic acid derivatives; heterocyclic acid derivatives; and cinnamic acid derivatives. Examples of such carboxylic acid derivatives which may be useful in the present invention include, but are not limited to, those disclosed at pages 72–91 of the Zahradnik reference.

Cinnamic acid derivatives which may be useful as optical brighteners in the present invention can be further subclassified into groups which include, but are not limited to, styrylazoles, styrylbenzofurans, styryloxadiazoles, styryltriazoles and styrylpolyphenyls, as disclosed on pages 77 of the Zahradnik reference. Styrylazoles can be further subclassified into styrylbenzoxazoles, styrylimidazoles, and styrylthiazoles, as disclosed on page 78 of the Zahradnik reference. It will be understood that these three identified subclasses may not necessarily reflect an exhaustive list of the subgroups into which styrylazoles may be subclassified. Examples of styrylbenzoxazole derivatives, 2-styrylbenzimidazole derivatives, styryl-benzofuran derivatives, styryloxadiazole derivatives, and styrylpolyphenyl derivatives which may be useful in the present invention include, but are not limited to those disclosed on pages 78–83 of the Zahradnik reference.

Methinecyanine derivatives which may be useful as optical brighteners in the present invention include, but are not limited to, those disclosed at pages 91–93 of the Zahradnik reference. Examples of these types of brighteners, include oxamethinecyanines and thiamethinecyanines.

Other optical brighteners which may be useful in the present invention include those disclosed in U.S. Pat. No. 3,646,015, issued Feb. 29, 1972 to Hamilton and those disclosed in U.S. Pat. No. 4,483,780, issued Nov. 20, 1984 to Llenado both of which are incorporated herein by reference.

Typical levels of optical brightener(s) are from about 0% to about 5%, preferably from about 0% to about 4%, even more preferably from about 0% to about 3%, most preferably at least 0.01% by weight of the composition.

Examples of dispersing agents useful in the detergent compositions of the present invention include, but are not limited to the polycarboxylate dispersing agents or the polyethylene glycol dispersing agents, which assist in removal of particulate soil from fabrics, textiles, etc. These polymeric dispersing agents are used in combination with detersive surfactants and other optional detergent adjuncts which are known in the art.

Polymeric polycarboxylate dispersing agents can advantageously be utilized in the compositions hereof. These materials can aid in calcium and magnesium hardness control. In addition to acting as a builder adjunct analogously to the polycarboxylate described above in the builder description, it is believed, though it is not intended to be limited by theory, that these higher molecular weight dispersing agents can further enhance overall detergent builder performance by inhibiting crystal growth of inorganics, by particulate soil peptization, and by anti-redepositions, when used in combination with other builders including lower molecular weight polycarboxylates. Particularly suitable polymeric polycarboxylates can be derived from acrylic acid. Such acrylic acid based polymers which are useful herein are the water soluble salts of polymerized acrylic acid. The average molecular weight of such polymers in the acid form ranges from about 2,000 to 10,000, more preferably from about 4,000 to 7,000 and most preferably from about 4,000 to 5,000. Water soluble salts of such acrylic acid polymers include, for example, the alkali metal, ammonium and alkanol-ammonium salts. Soluble polymers of this type are known materials. Use of polyacrylates of this type in detergent compositions has been disclosed, for example, in Diehl, U.S. Pat. No. 3,308,067, issued Mar. 7, 1967 which is incorporated herein by reference.

Acrylic/maleic based copolymers may also be used as a preferred component of the dispersing agent. Such materials include the water soluble salts of copolymers of acrylic acid and maleic acid. The average molecular weight of such copolymers in the acid form ranges from about 5,000 to 100,000, preferably from about 6,000 to 90,000, more preferably from about 7,000 to 80,000. The ratio of acrylate to maleate segments in such copolymers will generally range from about 30:1 lo about 1:1, more preferably from about 10:1 to 2:1. Water soluble salts of such acrylic acid/maleic acid copolymers include, for example, the alkali metal, ammonium, and alkanolammonium salts. Soluble acrylate/maleate copolymers of this type are known materials which are described in European Patent Application No. 66915, published Dec. 15, 1982 which is incorporated herein by reference.

Typical levels of polymeric dispersing agent are about 0% to about 10%, preferably from about 0% to about 7%, even more preferably from about 0% to about 5%, most preferably at least 0.1% by weight of the composition.

Examples of anti-redeposition agents useful in the detergent compositions of the present invention include, but are not limited to the polyethylene glycols and the water soluble ethoxylated amines having clay soil removal and anti-redeposition properties. If used, granular detergent compositions typically contain clay soil removal/anti-redeposition agent from about 0.01% to about 10.0% by weight cf the the composition, liquid detergent compositions typically contain from about 0.01% to about 5% by weight of the composition.

Examples of polymeric soil release agents useful in the present invention include cellulosic derivatives such as hydroxyether cellulosic polymers, copolymeric blocks of ethylene terephthalate or propylene terephthalate with polyethylene oxide or polypropylene oxide terephthalate, and the like.

Cellulosic derivatives that are functional as soil release agents are commercially available and include the hydroxyethers of cellulose such as Methocel® sold by Dow.

Cellulosic soil release agents for use herein also include those selected from the group consisting of $C_1$–$C_4$ alkyl and $C_4$ hydroxyalkyl cellulose such as methylcellulose, ethylcellulose, hydroxypropyl methylcellulose, hydroxybutyl methylcellulose and the like A variety of cellulose derivatives useful as soil release polymers are disclosed in U.S. Pat. No. 4,000,093, to Nicol et al., issued Dec. 28, 1976 which is incorporated herein by reference.

Soil release agents characterized by poly(vinyl ester) hydrophobe segments include graft copolymers of poly (vinyl ester), such as $C_1$–$C_6$ vinyl esters, preferably poly (vinyl acetate) grafted onto polyalkylene oxide backbones, particularly polyethylene oxide backbones. Such materials are known in the art and are described in European Patent Application 0,219,048, published Apr. 22, 1987 by Kud, et al. which is incorporated herein by reference. Suitable commercially available soil release agents of this type include those sold under the name Sokalan™ such as Sokalan™ HP-22, available from BASF (West Germany).

One type of preferred soil release agent is a copolymer having random blocks of ethylene terephthalate and polyethylene oxide (PEO) terephthalate. This copolymer is more fully described in U.S. Pat. No. 3,959,230 to Hays, issued May 25, 1976, and in U.S. Pat. No. 3,893,929 to Basadur issued Jul. 8, 1975 (incorporated by reference) which discloses similar copolymers, both of which are incorporated by reference Another preferred polymeric soil release agent is a polyester with repeat units of ethylene terephthalate units. These polymers and methods of their preparation are more fully described in U.S. Pat. No. 4,702,857, issued Oct. 27, 1987 to Gosselink which is incorporated herein by reference.

Yet another preferred polymeric soil release agent is a sulfonated product of a substantially linear ester oligomer comprised of an oligomeric ester backbone of terephthaloyl and oxyalkyleneoxy repeating units and terminal moieties covalently attached to the backbone. These soil release agents are described fully in U.S. Pat. No. 4,968,451, issued Nov. 6, 1990 to J. J. Scheibel and E. P. Gosselink, U.S. Ser. No. 07/474,709, filed Jan. 29, 1990 both of which are incorporated herein by reference.

Typical levels of soil release agent are from about 0% to about 10%, preferably from about 0% to about 7%, even more preferably from about 0% to about 5%, most preferably at least 0.1% by weight of the composition.

Examples of sud suppressing agents useful in the detergent compositions of the present invention include, but are not limited to those compounds that are known, or which become known, for reducing or suppressing the formation of suds. The incorporation of such materials, hereinafter "suds suppressors," can be desirable because the compounds of the invention can increase suds stability. A wide variety of materials may be used as suds suppressors in the compositions hereof. Suds suppressors are well known to those skilled in the art. They are generally described, for example, in Kirk Othmer Encyclopedia of Chemical Technology, Third Edition, Volume 7, pages 430–447 (John Wiley & Sons, Inc., 1979) which is incorporated herein by reference. Preferably from about 0.01% to about 1% of silicone suds suppressor may be used, more preferably from about 0.25% to about 0.5%. As used herein, these weight percentage values include any silica that may be utilized in combination with polyorganosiloxane, as well as any adjunct materials that can be utilized. Monostearyl phosphates may be generally utilized in the amounts ranging from about 0.1% to about 2% by weight of the composition.

Examples of abrasive agents useful in the scouring detergent compositions of the present invention include calcium carbonate, precipitated calcium carbonate and the like. Typical levels of abrasive agent are from about 0% to about 65% by weight of the composition.

Examples of foam boosters/stabilizers useful in the present invention include $C_8$–$C_{18}$ fatty alkanolamides, $C_8$–$C_{18}$ alkyl carboxy betaines, $C_8$–$C_{18}$ alkyl sulfobetaines and $C_8$–$C_{18}$ alkyl alkylamine oxides as well as mixtures thereof. Typical levels of foam booster/stabilizer are from about 0% to about 7% by weight of the composition.

Examples of antioxidants useful in the present invention which prevent the oxidation of certain ingredients by air and prevent the development of unpleasant, rancid odors include vitamin E (tocopherol), lecithin, wheat germ oil, sodium sulfite, sodium bisulfite, uric acid, propyl gallate, butylated hydroxyanisole (BHA), toluhydroquinone (THQ) sold as Tenox PG, Tenox BHA and Tenox THQ by Eastman Chemical Products Inc., and butylated hydroxytoluene (BHT) sold as Sustane BHT by LJOP Process Division. Typical levels of antioxidant used to prevent oxidation, are from about 0% to about 4% by weight of the composition.

Examples of encapsulating agents useful in the present invention include those described in U.S. Pat. No. 5,281,355, and U.S. Pat. No. 5,281,356, issued Jan. 25, 1994, to Tsaur et al. as well as in European Patent Application 0,266,796 all of which are incorporated by reference. Such materials are generally designed to encapsulate sensitive detergent ingredients such as proteolytic enzymes, bleaches and the like, from degradation which are later released at a desirable time, particularly during the wash cycle. Encapsulating agents are generally water soluble polymers which can entrape the desired sensitive component. An example of a preferred water soluble polymer is a partially hydrolyzed polyvinyl alcohol (PVA) polymerized with styrene in about a 50:50 ratio. Typical levels of encapsulating agent are from about 0% to about 5% by weight of the composition.

Examples of ions useful in the present invention include magnesium ion ($Mg^{+2}$), which may be used at a level of up to 1.5%, more preferably from 0.01% to 1.0% by weight of the composition and calcium ion which may be used at a level of from 0.01% to 0.5% by weight of the composition.

Examples of antitarnish agents useful in the liquid detergent compostions of the present invention include, but are not limited to is adenine, gaunine, purine, xanthine, hypoxanthine, benzimidazole, 5-methyl benzimidazole, 2-phenyl imidazole, 2-benzyl imidazole, 4-allyl imidazole, 4-(β-hydroxyethyl)imidazole, 4-methyl imidazole, 2-methyl imidazole, 3-(β-hydroxyethyl)imdazole, 6-nitroindazole, 3,5-dimethyl pyrazole, 4-benzyl pyrazole, 4,5-dimethyl pyrazole, allyl pyrazole, benzotriazole, 4-phenyl-1,2,3-triazole, 1,3-triazole, 1,2-naphthotriazole, 4-nitrobenzotriazole, benz-oxytriazole, 1,3-azole and the like. A fuller description of such antitarnish agents and their application are disclosed in U.S. Pat. Nos. 2,618,606, 2,618,608 and 4,321,166 as well as in U.S. Ser. No. 08/301,459 all of which are incorporated herein by reference. Preferred antitarnish agents are the 1,3-azoles and the aromatic trazoles, particulary benzoxytriazole. Typical levels of antitarnish agent is from about 0% to about 3% by weight of the composition.

Examples of deflocculating polymers useful in the liquid detergent compostions of the present invention are thoses as described in U.S. Pat. No. 5,071,586 (Lever Brothers Company) which is incorporated herein by reference. Typical levels of deflocculating polymer are from about 0% to about 6% by weight of the composition.

Examples of a fillers useful in the powdered detergent compostions of the present invention are typically inorganic compounds such as sodium sulfate and potassium sulfate. Fillers may be considered formulation aids which help provide powdered detergent compositions with good flowability and dosing ability. Typical levels of filler are from about 0% to about 60% by weight of the composition, more preferably at least 0.1% by weight of the composition Examples of dye transfer inhibiting agents (colorcare agents) useful in the present invention which prevent the transfer of dyes between fabrics include, but are not limited to polyamine N-oxide polymers, alkoxy containing polymers (e.g. polyethylene glycol, copolymer of ethylene-propylene glycol polyethylene terephthalate etc.), hydroxy containing polymers (e.g. polyvinylalcohol etc.), thiol containing polymers, amide containing polymers (e.g. polyvinylpyrrolidone etc.), heterocyclic amine containing polymers (e.g. polyvinylimidazoline etc.), polyamines, polyurethanes, polyacrylonitriles, metallo porphins (e.g. iron porphin deriva-tives, metallo tetrasulfonated tetraphenylporphin etc.), metallo porphyrins, metallo phtalocyanines as well as mixtures thereof and the like. Such dye transfer inhibiting agents are described in EP Application Nos. 0,579,295, 0,581,751, 0,581,752, 0,581,753 to Abdennaceur et al. and EP Application No. 0,538,228 to Thoen et, al. which are all incorporated by reference. Highly preferred dye transfer inhibiting agents are polyvinylpyrrolidone (PVP), polyvinylimidazoline and polyamine N-oxide polymers. Typical levels of dye transfer inhibiting agent are from about 0% to about 10% by weight of the composition Many additional ingredients that are useful in the present invention are described in McCutcheon's, Detergents and Emulsifiers (Vol 1) and McCutcheon's, Functional Materials (Vol 2), 1996 Annual Edition, published by McCutcheon's MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

Water is the last essential component of the present invention and forms the remainder of the composition. When water is employed in the oral hygiene compositions of the present invention, it should be deionized and free of organic impurities. Water is generally present from about 1% to about 95%, preferably from about 45% to about 90

Industrial Application and Use

The glycacarbamate/urea compounds of the invention are useful as cleansing agents, surfactants, cosurfactants, detergents, surface tension reducing agents, soil release agents, stain/soil removal agents, antiredeposition agents, deposition agents, surface modification agents, absorption enhancing agents, solubilizing agents, clarity enhancing agents, wetting agents, rewetting agents, foaming agents, foam stabilizing agents, foam enhancing/boosting agents, pearlescent agents, opacifiers, suspending agents, enzyme stabilizing agents, bleach stabilizing agents, thickening agents, gelling agents, viscosity modifying agents, softening agents, moisturizering agents (occlusive), emollients, emulsifiers, humectants, dispersants, flow enhancing agents, processing agents, hardening agents, hygroscopicity masking agents, conditioning agents, antimicrobial agents/bactericides/fungicides, mildness enhancing agents, phase regulants and the like. In fact, by simple experimentation to those skilled in the art, additional beneficial properties of glycacarbamate/urea compounds of the invention can be determined and optimized.

In order to more fully illustrate the nature of the invention and the manner of practicing the same, the following examples are presented. These Examples are given solely for the purpose of illustration and are not to be construed as being limiting to the present invention since many variations are possible without departing from the spirit and scope of the invention.

EXAMPLES

Example 1

Preparation of N-Octyl D-Glucocarbamate

A four necked round bottom flask equipped with a mechanical stirrer, thermometer, nitrogen inlet and ammonia absorption trap was charged with N-octyl D-glucamine (2.00 g, 6.82×10$^{-3}$ mole) and urea (0.41 g, 6.82×10$^{-3}$ mole). The reaction mixture was heated to 140°–150° C. with agitation under a mild nitrogen blanket for several hours. After all the ammonia has evolved, the agitation was halted and the reaction mixture cooled to 40° C. Isopropanol (2.5 ml) was added and the reaction mixture heated to near reflux. After the product dissolves, the reaction mixture was slowly cooled to room temperature. A crystalline product soon forms which was filtered, washed with cold isopropanol (3×5 ml) and dried under high vacuum to give 1.6 g (73% yield) of N-octyl D-glucocarbamate.

| Proton Nuclear Magnetic Resonance Analysis ($^1$H NMR) in Dimethylsulfoxide/TMS | | |
|---|---|---|
| Proton # | Found Shift (δ) | Predicted Shift (δ) |
| 1 | 5.0d | 5.4s |
| 2 | 3.5m | 3.8d |
| 3 | 3.7m | 3.9m |
| 4 | 3.5m | 3.6m |
| 5 | 4.5m | 4.9q |
| 6 | 4.4m | 4.6m |
| 7 | 3.3m | 3.7d |
| 8 | 3.1m | 3.4t |
| 9 | 1.5bm | 1.4d |
| 10 | 1.5bm | 1.4m |
| 11–14 | 1.2s | 1.2m |
| 15 | 0.9t | 0.9t | s = singlet, d = doublet, t = triplet, q = quartet, m = multiplet, bm = broad multiplet

| Carbon Nuclear Magnetic Resonance Analysis ($^{13}$C NMR) in Dimethylsulfoxide/TMS | | |
|---|---|---|
| Carbon # | Found Shift (δ) | Predicted Shift (δ) |
| 1 | 157.5 | 157.3 |
| 2 | 63.2 | 65.3 |
| 3 | 70.9 | 67.2 |
| 4 | 71.0 | 71.2 |
| 5 | 74.8 | 79.4 |
| 6 | 69.8 | 67.4 |
| 7 | 45.7 | 49.1 |
| 8 | 43.2 | 44.1 |
| 9 | 26.9 | 28.5 |
| 10 | 26.1 | 28.4 |
| 11 | 28.7 | 29.9 |
| 12 | 28.7 | 29.8 |
| 13 | 31.3 | 32.4 |
| 14 | 22.1 | 23.1 |
| 15 | 14.0 | 14.2 |

From the above $^1$H and $^{13}$C NMR analysis it can be seen that N-octyl D-glucocarbamate was prepared.

Example 2

Preparation of N-Decyl D-Glucocarbamate

Prepared in a similiar manner as Example 1, however decyl D-glucamine was used. The yield was 74%.

Example 3

Preparation of N-Dodecyl D-Glucocarbamate

Prepared in a similiar manner as Example 1, however dodecyl D-glucamine was used. The yield was 66%.

Example 4

Preparation of N-Tetradecyl D-Glucocarbamate

Prepared in a similiar manner as Example 1, however tetradecyl D-glucamine was used. The yield was 67%.

Example 5

Preparation of N-Hexadecyl D-Glucocarbamate

Prepared in a similiar manner as Example 1, however hexadecyl D-glucamine was used. The yield was 71%.

Example 6

Preparation of N-Octadecyl D-Glucocarbamate

Prepared in a similiar manner as Example 1, however octadecyl D-glucamine was used. The yield was 74%.

Example 7

Preparation of N-Coconut D-Glucocarbamate (New)

Prepared in a similar manner as Example 1, however coconut D-glucamine was used and the product was not crystallized from isopropanol. The yield was 95%.

Example 8

Preparation of N-Tallow D-Glucocarbamate (New)

Prepared in a similar manner as Example 1, however tallow D-glucamine was used and the product was not crystallized from isopropanol. The yield was 94%.

Example 9

Preparation of N-Octyl/Decyloxypropyl D-Glucocarbamate (New)

Prepared in a similar manner as Example 1, however octyl/decyloxypropyl D-glucamine was used. The yield was 68%.

Example 10

Preparation of N-Dodecyl/Tetradecyloxypropyl D-Glucocarbamate (New)

Prepared in a similar manner as Example 1, however dodecyltetradecyloxypropyl D-glucamine was used. The yield was 44%.

Example 11

Preparation of N-Dodecyl D-Maltocarbamate (New)

Prepared in a similar manner as Example 1, however dodecyl D-maltamine was used. The yield was 54%.

Example 12

Preparation of N-Decyl D-Glucourea

A four necked round bottom flask equipped with a mechanical stirrer, thermometer, nitrogen inlet and outlet was charged with water (3 ml), N-decyl D-glucamine (3.2 g, 0.01 mole) and potassium cyanate (0.8 g, 0.01 mole). The reaction mixture was heated to 40° C. with agitation under a mild nitrogen blanket. Hydrochloric acid (2N, ~3 ml) was added dropwise from an addition funnel over one hour. The reaction mixture was heated to 70° C. for 7 hours and then slowly cooled to 0° C. in an ice bath. A crystalline product soon forms which was filtered, washed with cold water (3×5 ml) and dried under high vacuum to give 2.2 g (60% yield) of N-decyl D-glucourea.

Example 13

Preparation of N-Dodecyl D-Glucourea

Prepared in a similar manner as Example 12, however dodecyl D-glucamine was used. The yield was 57%.

Example 14

Preparation of N-Hexadecyl D-Glucourea

Prepared in a similar manner as Example 12, however hexadecyl D-glucamine was used. The yield was 44%.

Example 15

Preparation of N-Coconut D-Glucourea (New)

Prepared in a similar manner as Example 12, however coconut D-glucamine was used. The yield was 66%.

Example 16

Preparation of N-Octyl/Decyloxypropyl D-Glucourea (New)

Prepared in a similar manner as Example 12, however octyl/decyloxypropyl D-glucamine was used. The yield was 61%.

From Examples 1–16, it can be seen that Examples 7,8,9,10,11,15 and 16 represent novel glycacarbamate and glycaurea compounds of the invention. Examples 9,10,11 and 16 have enhanced water solubility and become less turbid in aqueous personal product and detergent compositions, particularily when compared to other known glycacarbamate and glycaurea compounds of the invention.

Examples 17–19

Physical Chemistry of Glycacarbamate/Urea Compounds

There are several unique characteristic properties that distinguish surface-active materials (sufactants) from other non-surface active materials. The following Examples will show that certain glycacarbamate/urea compounds of the invention to be surface-active and are therefore expected to deliver favorable surfactant benefits, whereas certain other glycacarbamate/urea compounds of the invention are not suface-active but instead provide pearlescence and suspending action.

Example 17

Water Solubility and Krafft Point of Glycacarbamate/Urea Compounds

The water solubility of several glycacarbamate/urea compounds of the invention were determined by preparing a 0.1% solution of a glycacarbamate or glycaurea in a 5 ml vial, heating that solution to 40° C. and observing the solubility of the glycacarbamate/urea compound in water. Materials that were soluble in water were considered have a krafft point below 40° C., whereas materials that were insoluble in water were considered have a krafft point above 40° C.

The temperature at which a surfactant forms micelles instead of precipitates is referred to as the Krafft point (Tk), and at or below this temperature the solubility of a surfactant becomes equal to its CMC (numerical value at which micelles are formed).

Micellization is the preferred interfacial phenomena, since certain surfactant benefits such as detergency (the solubilization of soils), foaming, wetting or emulsification depend on the formation of these aggregates in solution. Materials that do not form micelles do not provide any detergency, foaming, wetting or emulsification, but instead provide pearlescence and suspending action.

| The Water Solubility/Tk of Glycarbamate/Urea Compounds | | |
|---|---|---|
| Entry | Surfactant | H₂O Solubility/(Tk) at 40° C. |
| A | N-Octyl D-Glucocarbamate | Yes/Below Tk |
| B | N-Decyl D-Glucocarbamate | Yes/Below Tk |
| C | N-Dodecyl D-Glucocarbamate | Yes/Below Tk |
| D | N-Tetradecyl D-Glucocarbamate | Yes/Below Tk* |
| E | N-Hexadecyl D-Glucocarbamate | No/Above Tk |
| F | N-Octadecyl D-Glucocarbamate | No/Above Tk |
| G | N-Coconut D-Glucocarbamate | Yes/Below Tk |
| H | N-Tallow D-Glucocarbamate | No/Above Tk |
| I | N-Octyl/Decyloxypropyl D-Glucocarbamate | Yes/Below Tk |
| J | N-Dodecyl/Tetradecyl D-Glucocarbamate Hexaoxyethylene Ether | Yes/Below Tk |
| K | N-Dodecyl D-Maltocarbamate | Yes/Below Tk |
| L | N-Decyl D-Glucourea | Yes/Below Tk |
| M | N-Dodecyl D-Glucourea | Yes/Below Tk |
| N | N-Hexadecyl D-Glucourea | No/Above Tk |
| O | N-Coconut D-Glucourea | Yes/Below Tk |
| P | N-Octyl/Decyloxypropyl D-Glucourea | Yes/Below Tk |

*With slight Heating

From the above table it can be seen that several glycacarbamate/urea compounds of the invention are water soluble and exist below their Krafft points (A-D, G, I-M, O-P), whereas several other glycacarbamate/urea compounds of the invention are insoluble in water and exist above their Krafft points (E-F, H, N). This finding suggests that the water soluble glycacarbamate/urea compounds to be surface-active and are expected to deliver favorable surfactant benefits, whereas the insoluble glycacarbamate/urea compounds are not surface-active and are expected to deliver pearlescence and suspending action.

Example 18

Critical Micelle Concentration of Glycacarbamate/Urea Compounds

The critical micelle concentration (CMC) is defined as the concentration at which a surfactant forms micelles in aqueous solution. Micellization is the preferred interfacial phenomena, since certain surfactant benefits such as detergency (the solubilization of soils), foaming, wetting or emulsification depend on formation of these aggregates in solution. Materials that do not form micelles do not provide any detergency, foaming, wetting or emulsification, but instead provide pearlescence and suspending action. A necessary and sufficient condition for CMC formation and surface tension reduction is the presence of both hydrophilic and hydrophobic functional groups. The hydrophilic portion provides strong interaction between the surfactant at the interface and with the surrounding water phase. The hydrophobic portion provides spontaneous adsorption of the surfactant at the interface and strong interaction with the adjacent air phase. If any of these functions are not performed, then CMC formation and surface tension reduction will not occur. For significant surface activity, a properly balanced hydrophilic and hydrophobic character is essential.

| The Critical Micelle Concentration of Glycarbamate/Urea Compounds | | |
|---|---|---|
| Entry | Surfactant | CMC at 40° C. |
| A | N-Octyl D-Glucocarbamate | Yes |
| B | N-Decyl D-Glucocarbamate | Yes |
| C | N-Dodecyl D-Glucocarbamate | Yes |
| D | N-Tetradecyl D-Glucocarbamate | Yes* |
| E | N-Hexadecyl D-Glucocarbamate | No |
| F | N-Octadecyl D-Glucocarbamate | No |
| G | N-Coconut D-Glucocarbamate | Yes |
| H | N-Tallow D-Glucocarbamate | No |
| I | N-Octyl/Decyloxypropyl D-Glucocarbamate | Yes |
| J | N-Dodecyl/Tetradecyl D-Glucocarbamate Hexaoxyethylene Ether | Yes |
| K | N-Dodecyl D-Maltocarbamate | Yes |
| L | N-Decyl D-Glucourea | Yes |
| M | N-Dodecyl D-Glucourea | Yes |
| N | N-Hexadecyl D-Glucourea | No |
| O | N-Coconut D-Glucourea | Yes |
| P | N-Octyl/Decyloxypropyl D-Glucourea | Yes |

*With slight Heating

From the above table it can be seen that several glycacarbamate/urea compounds of the invention are properly balanced and form micelles (A-D, G, I-M, O-P) whereas, several other glycacarbamate/urea compounds of the invention are insoluble in water and do not form micelles (E,F,M). This finding suggests that the micelle forming glycacarbamate/urea compounds are surface-active and are expected to deliver favorable surfactant benefits, whereas the non-micelle forming glycacarbamate/urea compounds are not surface-active and are expected to deliver pearlescence and suspending action.

Example 19

Surface Tension Reduction of Glycacarbamate/Urea Compounds

An important characteristic feature that surfactants have is the tendency for them to absorb at the water/air interface in an oriented manner, thereby altering the interfacial free energy of that surface. The surface free energy per unit area or surface tension ($\gamma$), is a measure of this work and may be considered as the minimum amount of work required to bring sufficient surfactant molecules to the surface.

| The Surface Tension Reduction of Glycacarbamate/Urea Compounds | | |
|---|---|---|
| Entry | Surfactant | ($\gamma$) at 40° C. |
| A | N-Octyl D-Glucocarbamate | Yes |
| B | N-Decyl D-Glucocarbamate | Yes |
| C | N-Dodecyl D-Glucocarbamate | Yes |
| D | N-Tetradecyl D-Glucocarbamate | Yes* |
| E | N-Hexadecyl D-Glucocarbamate | No |
| F | N-Octadecyl D-Glucocarbamate | No |
| G | N-Coconut D-Glucocarbamate | Yes |
| H | N-Tallow D-Glucocarbamate | No |
| I | N-Octyl/Decyloxypropyl D-Glucocarbamate | Yes |
| J | N-Dodecyl/Tetradecyl D-Glucocarbamate Hexaoxyethylene Ether | Yes |
| K | N-Dodecyl D-Maltocarbamate | Yes |
| L | N-Decyl D-Glucourea | Yes |
| M | N-Dodecyl D-Glucourea | Yes |
| N | N-Hexadecyl D-Glucourea | No |
| O | N-Coconut D-Glucourea | Yes |
| P | N-Octyl/Decyloxypropyl D-Glucourea | Yes |

*With slight Heating

From the above table it can be seen that several glycacarbamate/urea compounds of the invention absorb strongly at the water/air interface and significantly reduce the surface tension of water (A-D, G, I-M, O-P) whereas, several other glycacarbamate/urea compounds of the invention do not significantly reduce the surface tension of water (E,F,M). This finding suggests that the surface tension reducing glycacarbamate/urea compounds are surface-active and are expected to deliver favorable surfactant benefits, whereas the non-surface tension reducing glycacarbamate/urea compounds are not surface-active and are expected to deliver pearlescence and suspending action.

Example 20

Mildness Potential of Glycacarbamate/Urea Compounds

The zein solubilization assay was developed to determine the biological effects of surfactants on the skin. The protein is normally in soluble in water, but can be brought into solution by interaction with surfactants. The extent of zein dissolbed is related to the irritation potential (M. J. Schwinger, Kolloid-Z. Z. Poly., 233, 848, 1969). The larger the zein solubilization, the greater the irrtation potential of that surfactant on the skin, and conversly, the smaller the zein solubilization, the lesser irritation potential of that surfactant.

In order to demonstrate the improved ability of the glycacarbamate/urea compounds of the invention to provide mildness benefits to the skin, mixtures of N-dodecyl D-glucocarbamate, N-dodecyl D-glucourea (50:50) and sodium lauryl sulfate (SLS) were tested and compared to pure SLS. Thus, a 1% solution of surfactant (30 mls) was added to 1.5 g of zein and stirred at room temperature for 1 hour. Residual zein was collected and dired to constant weight. Differences between starting and residual weights were used to calculate % zein solubilized. The results are as follows:

| Mildness Potential of Glycacarbamate/Urea Compounds (Zein Solubilization Assay) | |
|---|---|
| Active Ratio ([50/50] N-Coconut D-Glucocarbamate/Urea:SLS) | % Zein Solubilized |
| 0:100 | 84 |
| 25:75 | 61 |
| 50:50 | 45 |
| 75:25 | 20 |
| 100:0 | 7 |
| No Surfactant (Control) | 5 |

As indicated by the above table, the addition of a 50:50 mixture of N-coconut D-glucocarbamate and N coconut D-glucourea to sodium lauryl sulfate results in less zein solubilization. This result suggests that such formulations (25:75 to 100:0) are more mild than sodium lauryl sulfate alone, and so the glycacarbamate/urea compounds of the invention are mild to the skin and form mild surfactant mixtures.

Example 21–22

Pearlescent/Suspending Action of Glycacarbamate/Urea Compounds

In order to demonstrate the improved ability of glycacarbamate/urea compounds of the invention to provide pearlescence/suspending action, several prototype personal product compositions were prepared and their appearance were measured at room temperature (~21° C.). The formulations were placed in a clear jar and stored for 1 month. The prototype personal product compositions are as follows:

| Ingredients | Wt | Function |
|---|---|---|
| Personal Product Compositions Comprising Sodium Lauryl Sulfate and Glycacarbamate Compounds | | |
| Sodium Lauryl Sulfate | 15.0% | Cleansing Agent |
| N-Tallow D-Glucocarbamate | 0.5–4.0% | Pearlescent/Suspending Agent |
| Sodium Chloride | 2.0% | Viscosity Cobuilder |
| Distilled Water | Balance | |
| Total | 100.0% | |
| Personal Product Compositions Comprising Sodium Lauryl Sulfate and Glycaurea Compounds | | |
| Sodium Lauryl Sulfate | 15.0% | Cleansing Agent |
| N-Hexadecyl D-Glucourea | 0.5-4.0% | Pearlescent/Suspending Agent |
| Sodium Chloride | 2.0% | Viscosity Cobuilder |
| Distilled Water | Balance | |
| Total | 100.0% | |

The above formulations were prepared by admixing the above ingredients in listed order and heating the mixture to about 80° C. with rapid stirring. The mixture was then cooled to about 40° C., placed in a clear jar and stored at room temperature.

For a pearlecent personal product formulation to be successful it must have good shelf life and should not separate upon standing.

| The Pearlescence of Prototype Personal Product Compositions Comprising Sodium Lauryl Sulfate and Glycacarbamate/Urea Compounds | | |
|---|---|---|
| Wt | Opacifier | Appearance |
| 0.5% | N-Tallow D-Glucocarbamate | Pearlescent/Suspending Action |
| 0.5% | N-Hexadecyl D-Glucourea | Pearlescent/Suspending Action |
| 1.0% | N-Tallow D-Glucocarbamate | Pearlescent/Suspending Action |
| 1.0% | N-Hexadecyl D-Glucourea | Pearlescent/Suspending Action |
| 2.0% | N-Tallow D-Glucocarbamate | Pearlescent/Suspending Action |
| 2.0% | N-Hexadecyl D-Glucourea | Pearlescent/Suspending Action |
| 3.0% | N-Tallow D-Glucocarbamate | Pearlescent/Suspending Action |
| 3.0% | N-Hexadecyl D-Glucourea | Pearlescent/Suspending Action |
| 4.0% | N-Tallow D-Glucocarbamate | Pearlescent/Suspending Action |
| 4.0% | N-Hexadecyl D-Glucourea | Pearlescent/Suspending Action |

From the obove table it can be seen that N-tallow D-glucocarbamate and N-hexadecyl D-glucourea provide excellent pearlescence and therefore compositions comprising certain glycacarbamate/urea compounds of the inention exhibit a soft, silvery and pearly luster as well as uniform suspending action of performance ingredients.

Examples 23–25

Viscosity/Clarity Enhancement and Foam Stabilization of Glycacarbamate/Urea Compounds A) Viscosity/Clarity Enhancement The viscosity or thickness of a personal product or detergent composition plays an important role in the selection of that product, since consumers are accustomed to, and expect personal product and detergent compositions to be thick and viscous. If a personal product or detergent composition is thin and nonviscous, a consumer may conclude the product to be inferior. Furthermore, successful personal product and detergent compositions must have good shelf life and should not become turbid or produce sedimentation upon standing. Ideal personal product and detergent compositions should cleanse gently without overdrying the skin. Surprising the personal product and detergent compositions of the present invention that comprise certain glycacarbamate/urea compounds of the invention produce clear, stable, thick liquid composition with good foam and cleansing characteristics.

B) Foam Stabilization

The ability of a personal product or detergent composition to create a desirable rich lather is significant driving force in the selection of that product. This important psychological stimulus derived from tactile and visual perceptions by the consumer, make it necessary to formulate compositions with ingredients that generate a high level of stable foam or lather. Furthermore, the generation of a thick, persistent lather also serves as a vehicle to sispend dirt and prevent redeposition during the rinse cycle. Surprisingly the personal product compounds produce and enhanced thick, copious, persistent foam and lather.

By contrast, compositions that lack certain glycacarbamate/urea compounds exhibit low viscosity and poor foam

Example 23

Viscosity Modification of Sodium Lauryl Sulfate with Glycacarbamate/Urea Compounds In order to demonstrate the improved ability of glycacarbamate/urea compounds of the invention to enhance viscosity, several prototype detergent compositions were prepared and their viscosity measured using a Brookfield Digital Viscometer at 22° C. The prototype detergent compositions are as follows:

| Ingredients | Wt | Function |
|---|---|---|
| Detergent Compositions Comprising Sodium Lauryl Sulfate and Glycacarbamate Compounds | | |
| Sodium Lauryl Sulfate | 15.0% | Cleansing Agent |
| N-Dodecyl D-Glucocarbamate | 2.0–7.0% | Foam Stabilizer/Thickener |
| Sodium Chloride | 2.0% | Viscosity Cobuilder |
| Distilled Water | Balance | |
| Total | 100.0% | |
| Detergent Compositions Comprising Sodium Lauryl Sulfate and Glycaurea Compounds | | |
| Sodium Lauryl Sulfate | 15.0% | Cleansing Agent |
| N-Dodecyl D-Glucourea | 2.0–7.0% | Foam Stabilizer/Thickener |
| Sodium Chloride | 2.0% | Viscosity Cobuilder |
| Distilled Water | Balance | |
| Total | 100.0% | |

The above formulations were prepared by admixing the above ingredients in listed order and heating the mixture to about 80° C. with rapid stirring. The mixture was then cooled to about 40° C., placed in a clear jar and stored at room temperature.

It is well known that the viscosity of a liquid composition comprision of anionic surfactant can be modified by the addition of inorganic salts, such as sodium chloride. However, in the absence of an organic modifier, high levels of salt may be necessary to achieve the required viscosity which may lead to problems of storage at cold temperature or even salting our certain ingredients. In practice, however, the viscosity of a liquid compositionis modified by the simultaneous addition of thickener and small amounts of inorganic salt (viscosity cobuilder). The combined effect is greater than either one alone. The viscosity of the above prototype detergent compositions comprising various amounts of glycacarbamate/urea compound are as follows:

| Wt | Thickener | Viscosity Increase | Appearance |
|---|---|---|---|
| The Viscosity of Prototype Detergent Compositions Comprising Sodium Lauryl Sulfate and Glycacarbamate/Urea Compounds | | | |
| 2.0% | N-Dodecyl D-Glucocarbamate | Yes | Slightly Viscous |
| 2.0% | N-Dodecyl D-Glucourea | Yes | Slightly Viscous |
| 2.0% | D-Glucose (Comparative) | No | Purable Liquid |
| 4.0% | N-Dodecyl D-Glucocarbamate | Yes | Viscous |
| 4.0% | N-Dodecyl D-Glucourea | Yes | Viscous |
| 4.0% | D-Glucose (Comparative) | No | Purable Liquid |
| 7.0% | N-Dodecyl D-Glucocarbamate | Yes | Very Viscous |
| 7.0% | N-Dodecyl D-Glucourea | Yes | Very Viscous |
| 7.0% | D-Glucose (Comparative) | No | Purable Liquid |
| 0.0% | No Thickener (Control) | No | Purable Liquid |

From the above table it can be seen that the addition of a N-dodecyl D-glucocarbamate or N-dodecyl D-glucourea compound to a detergent formulation increases the viscosity of that composition more effectively than D-glucose. This finding suggests that glycacarbamate/urea compounds of the invention are useful as effective viscosity modifiers, thickeners or gelling agents.

Example 24

Clarity Enhancement of Glycacarbamate/Urea Compounds

In order to demonstrate the improved ability of glycacarbamate/urea compounds of the invention to enhance clarity, several prototype detergent compositions were prepared and their clarity were measured at room temperature (~21° C.). The formulations were placed in a clear jar and stored for 1 month. The prototype detergent compositions are as follows:

| Ingredients | Wt | Function |
|---|---|---|
| Detergent Compositions Comprising Sodium Lauryl Sulfate and Glycacarbamate Compounds | | |
| Sodium Lauryl Sulfate | 15.0% | Cleansing Agent |
| N-Coconut D-Glucocarbamate | 0.5–4.0% | Foam Stabilizer/Thickener |
| Sodium Chloride | 2.0% | Viscosity Cobuilder |
| Distilled Water | Balance | |
| Total | 100.0% | |
| Detergent Compositions Comprising Sodium Lauryl Sulfate and Glycacarbamate Compounds | | |
| Sodium Lauryl Sulfate | 15.0% | Cleansing Agent |
| N-$C_8$/$C_{10}$oxypropyl D-Glucocarb. | 0.5–4.0% | Foam Stabilizer/Thickener |
| Sodium Chloride | 2.0% | Viscosity Cobuilder |
| Distilled Water | Balance | |
| Total | 100.0% | |
| Detergent Compositions Comprising Sodium Lauryl Sulfate and Glycaurea Compounds | | |
| Sodium Lauryl Sulfate | 15.0% | Cleansing Agent |
| N-Dodecyl D-Glucourea | 0.5–4.0% | Foam Stabilizer/Thickener |
| Sodium Chloride | 2.0% | Viscosity Cobuilder |
| Distilled Water | Balance | |
| Total | 100.0% | |

The above formulations were prepared by admixing the above ingredients in listed order and heating the mixture to about 80° C. with rapid stirring. The mixture was then cooled to about 40° C., placed in a clear jar and stored at room temperature.

For a clear detergent formulation to be successful it must have good shelf life and should not become turbid or produce sedimentation upon standing.

| The Clarity of Prototype Detergent Compositions Comprising Sodium Lauryl Sulfate and Glycacarbamate/Urea Compounds | | |
|---|---|---|
| Wt | Thickener | Appearance |
| 0.5% | N-Coconut D-Glucocarbamate | Clear |
| 0.5% | N-Octyl/Decyloxypropyl D-Glucocarbamate | Clear |
| 0.5% | N-Coconut D-Glucourea | Clear |
| 1.0% | N-Coconut D-Glucocarbamate | Clear |
| 1.0% | N-Octyl/Decyloxypropyl D-Glucocarbamate | Clear |
| 1.0% | N-Coconut D-Glucourea | Clear |
| 2.0% | N-Coconut D-Glucocarbamate | Clear |
| 2.0% | N-Octyl/Decyloxypropyl D-Glucocarbamate | Clear |
| 2.0% | N-Coconut D-Glucourea | Clear |
| 3.0% | N-Coconut D-Glucocarbamate | Clear |
| 3.0% | N-Octyl/Decyloxypropyl D-Glucocarbamate | Clear |
| 3.0% | N-Coconut D-Glucourea | Clear |
| 4.0% | N-Coconut D-Glucocarbamate | Clear |
| 4.0% | N-Octyl/Decyloxypropyl D-Glucocarbamate | Clear |
| 4.0% | N-Coconut D-Glucourea | Clear |

From the above table it can be seen that the addition of a N-dodecyl D-glucocarbamate, N-octyl/decyloxypropyl D-glucocarbamate or N-dodecyl D-glucourea compound to a detergent formulation produces a formulation that is clear without sedimentation. This finding suggests that glycacarbamate/urea compounds of the invention are useful clarifying or solubilizing agents.

Example 25

Viscosity Enhancement/Foam Stabilization of Glycacarbamate/Urea Compounds

In order to further demonstrate the improved ability of the glycarcabamate/urea compounds of the invention to enhance viscoscity as well as stabilize foam, the viscocity and foam stabilization of several prototype detergent compositions in Example 24 were measured using a Brookfield Digital Viscometer at 22° C. The results are as follows:

| Viscosity Enhancement of Sodium/Ammonium Lauryl Sulfate with Glycacarbamate/Urea Compounds Formulation (Example 23) | | |
|---|---|---|
| Thickener (4.0%) | Viscosity (Centipoise) | Foam Stability |
| N-Dodecyl D-Glucocarbamate | 2176 | Yes |
| N-Dodecyl D-Glucourea | 2295 | Yes |
| Lauramide DEA | 2376 | Yes |
| Cocoamide MEA | 1720 | Yes |
| Neodol 91-6 | 212 | No |
| D-Glucose | 27 | No |
| No Thickener (Control) | 22 | No |

From the above table it can be seen that the addition of N-dodecyl D-glucocarbamate or N-dodecyl D-glucourea to a detergent formulation increases the viscosity of that composition 99–104 times and from its normal viscosity. Also closer comparison reveals that N-dodecyl D-glucocarbamate and N-dodecyl D-glucourea not only enhance the viscosity, but also stabilize foam. Both compounds enhance viscosity and stabilze foam compartively to lauramide diethanolamine (DEA), but better than cocoamide menoethanolamine (MEA), Neodol 91-6 ($C_9$–$C_{11}$ alcohol ethoxylate with 6 moles of ethylene oxide) and D-glucose. This finding suggests that the glycacarbamate/urea compounds of the invention are useful as effective foam enhancing/stabilizing agents, viscoscity modifiers, thickeners or gelling agents.

Detailed discussion of Examples 23–25

While not wishing to be bound to theory, it is believed that common thickener and foam stabilizers such as lauramide DEA and cocoamide MEA operate by being solubilized in the palisade layer of the ionic micelle. Here they act as "buffers" between repelling ionic head groups producing a closer-packed coherent suface film of foam that is more resilient and slow draining. The efficency of an additive to stabilize foam and enhance viscosity increases with the number of hydrogen bonding groups per molecule as well as the number of carbonds in the alkyl chain. Additive hydrogen bonding groups are attached to the ionic head groups of the sufactant by ion-dipole interactions whereas the hydrocarbon portions are attracted by Van der Waals forces. Therefore, the greater the intermolecular cohesive forces, the more effectively the additive is held in the palisade layer. Since long chained glycacarbamate/urea compounds of the invention contain multiple hydrogen bonding groups, they should be held tightly in the palisade layer and shoulc not be squeezed out of forced into the interior of the micelle. If the glycacarbamate/urea compound is of proper size, as those described in this disclosure, a composition will exhibit enhanced stable foam, clarity and increase viscosity as shown in Example 23–25.

Example 26

Glycacarbamate/Urea Compounds as Flow Aids (Intimate Admixtures)

It is known in the are that certain ingredients are hygroscopic in nature and liquify after exposure to moisture after a few days. For example, tetrasodium oxydisuccinate (ODS), tetrasodium sulfocarboxymethyloxysuccinate (SCMOS) as well as copolymers of maleic anhydride and acrylic acid (CP-5 and CP-7) are typical ingredients that are hygroscopic and liquify quickly. When these ingredients are formulated in powdered detergent compositions, particularly at high concentrations, such compositions tend to become sticky and are often hard to handle and exhibit poor flow characteristics.

In order to demonstrate the enhanced ability of glycarbamate/urea compounds of the invention to improve the handling and flow characteristics of hygroscopic detergent ingedients, several compositions comprising ODS, SCMOS, CP-5 or CP-7 and N-dodecyl D-glucocarbamate ($C_{12}$ Carb), N-dodecyl N-glucourea ($C_{12}$ Urea), N-tetradecyl D-glucocarbamate ($C_{14}$ Carb) or N-hexadecyl N-glucourea ($C_{16}$ Urea) were dry blended to form various intimate admixtures in a ratio of 1:1–1:2 by weight. All intimate admixtures were stored at 25° C., 65% relative humidity (R. H.) for variable periods of time. Samples were removed periodically, weighed and returned to R. H. chamber. Percent water uptake was based on the amound of builder present.

% $H_2O$ Uptake=grams of water absorbed/grams of builder×100

Identical mixtures of ODS, SCMOS, CP-5 or CP-7 and methyl α-D-glucose-6-O-monolaurate ($c_{12}$ Mgluc), dodecyl β-D-glucopyranoside ($C_{12}$ Gluc), dodecyl β-D-maltoside ($C_{12}$ Malt), D-glucose or D-sorbitol were also prepared and are used for comparison. When the comparative sugar surfactant of monosacchardie are used, percent water uptake was based on the amount of saccharide present.

% $H_2O$ Uptake=grams of water absorbed/grams of saccharide×100

| Compound(s) | Time (Days) | % $H_2O$ Uptake | Appearance |
|---|---|---|---|
| Intimate Admixture of Glycacarbamate/Urea Compounds and ODS | | | |
| $Na_4$ ODS | 4 | 59 | Liquid |
| $Na_4$ ODS/$C_{14}$ Carb (1:1) | 7 | 62 | Flowing Solid |
| $Na_4$ ODS/$C_{12}$ Carb (1:2) | 7 | 57 | Flowing Solid |
| $Na_4$ ODS/$C_{16}$ Urea (1:1) | 7 | 58 | Flowing Solid |
| $Na_4$ ODS/$C_{12}$ Urea (1:2) | 7 | 55 | Flowing Solid |
| $Na_4$ ODS/$C_{12}$ Mgluc (1:2) | 7 | 52 | Sl. Sticky Solid |
| $Na_4$ ODS/$C_{12}$ Gluc (1:2) | 7 | 59 | Sticky Solid |
| $Na_4$ ODS/$C_{12}$ Malt (1:2) | 7 | 60 | Sticky Solid |
| Intimate Admixture of Glycacarbamate/Urea Compounds and SCMOS | | | |
| $Na_4$ SCMOS | 9 | 38 | Sticky Paste |
| $Na_4$ SCMOS/$C_{14}$ Carb (1:2) | 9 | 39 | Flowing Solid |
| $Na_4$ SCMOS/$C_{14}$ Urea (1:2) | 9 | 36 | Flowing Solid |
| $Na_4$ SCMOS/Glucose (1:2) | 3 | 41 | Sticky Solid |
| $Na_4$ SCMOS/Sorbitol (1:2) | 2 | 56 | Sticky Solid |
| Intimate Admixture of Glycacarbamate/Urea Compounds and CP-5 and CP-7 | | | |
| CP-5 | 7 | 51 | Liquid |
| CP-7 | 7 | 30 | Sticky Paste |
| CP-5/$C_{14}$ Urea (1:2) | 7 | 36 | Flowing Solid |
| CP-7/$C_{14}$ Urea (1:1) | 7 | 32 | Flowing Solid |

From the above table it can be seen that intimate admixtures of N-dodecyl D-glucocarbamate, N-dodecyl D-glucourea, N-tetradecyl D-glucocarbamate or N-hexadecyl D-glucourea with ODS, SCMOS, CP-5 or CP-7 exhibit improved the handling and flowing characteristics, particularly when compared to mixtures containing other sugar surfactants or monosaccharides such as α-D-glucose-6-O-monolaurate, dodecyl β-D-glucopyranoside or dodecyl β-D-maltoside, D-glucose or D-sorbitol. Intimate admixtures of hygroscopic detergent ingredients and the compounds of the invention are free flowing and powdery in appearance. This finding suggests that the glycacarbamate/urea compounds of the invention are useful as flow aids for powdered or granular detergent compositions.

Example 27–30

Detergency Evaluation of Glycacarbamate/Urea Compounds

It is generally understood that detergency is defined as the cleansing quality of power of a detergent to remove soil and stains. While not wishing to be bound by theory, it is believed that glycacarbamate/urea compounds of the invention and cosurfactants remove soils together or independently through three different possible modes of action (which is dependent on the type of soil present). The first mode of action, involves an effective and efficient lowering of surface tension of water (as in Example 19), which results in a change in the interfacial properties of soil and fabric making the soil more susceptible to removal. The second mode of action is emulsification of greasy dirt or oily soil whereby the greasy dirt or oily soil are broken down up into tiny droplets which can be held in suspension (in solution) and rinsed away. The third mode of action is absorption of soil which is an active property of high foaming surfactants (as in Example 25) in which soil particle attach themselves to the surface of bubbles (foam) and are suspended on that surface and off the fabric. A stable persistant foam is required throughout the washing cycle for this mode of action to wor effectively.

A great number of test methods have been developed to determine the performace of detergents and various detergent ingredients. A preferred, well excepted test method involves applying various soils uniformly to a standard cloth under strict specifications yielding an "artifically soild test cloth", wich is then washed under controlled conditions in a Terg-o-tometer (washing machine simulator). The detergency of the sufactant is assessed electronically using a reflectometer (Colorgard 2000). Before washing, the initial relectance value of the soild test cloth is measure (front and back) giving a value which is represented as reflectance soiled ($R_s$). After washing, the final reflectance value of the soiled test cloth is measured (front and back) giving a value which is represented as reflectance-washed ($R_w$). From these values, the differences in reflectance $\Delta R = R_w - R_s$ can be calculated and used as a measure of soil removal. It shall be understood that higher $\Delta R$ values suggests better or enhanced detergency.

In general, textiles come in contact with a variety of soils, some of which are complicated mixtures of materials differing in their chemical and physical structure. The selection of a model soil representing a natural "real life" soil is a complicated problem. However, significant progress has been made in the area of fabric washing making artifical soiling more realistic. Since it is not practical to test the surfactant detergency with every possible soil that may be encountered, it must therefore be limited to typical model soils representing the most common natural soils. Artifical soils are usually selected to represent the following four types of common natural soils which includes (1) particulate soils, (2) fatty soils, (3) stains and (4) oily soils.

The detergency evaluation of glycacarbamate/urea compounds of the invention were determine on Lever Clay cloth, VCD cloth and WFK 30D cloth. Each of the cloths were soiled with the following materials and used in Examples 27–30:

| Cloth | Soil |
|---|---|
| Lever Clay Cloth | Polyester/cotton cloth (65:35) soiled with an extremely hydrophobic ditallowdiamine cation, kaolinitic clay and quartz (particulate and fatty soil). |
| VCD cloth | Polyester/cotton cloth (65:35) soiled with fatty material collected from vacuum bags (particulate and fatty soil). |
| WFK 30D cloth | Polyester soiled with pigment and sebum (particulate, fatty and oily soil). |

The WFK synthetic pigment consists of:

85.0% Kaolinite
8.0% Flame Soot 101
4.0% Iron Oxide Black
2.0% Iron Oxide Yellow

100%

The WFK synthetic sebum consists of:

18.0% Free Fatty Acids
32.8% Beef Tallow
3.6% Fatty Acid Triglycerides
18.3% Lanoline
3.7% Cholesterol
12.0% Hydrocarbon Mixture
11.6% Cutina

100%

The following wash conditions were used for Examples 27–30:

| Wash Conditions | |
| --- | --- |
| Apparatus | Tergotometer UR7227 |
| Wash Time | 20 minutes |
| Agitation | 70 rpm |
| Wash Liquid Level | 1000 ml |
| Surfactant System | 0.22 g/l |
| Zeolite 4A | 0.45 g/l |
| Sodium Carbonate | 0.30 g/l |
| pH | 10 |
| Hardness | 18 FH (4:1 Ca:Mg) |
| Temperature | 40° C. |
| Test Cloth/Pot Ratio | Four 3" × 4" Swatches/Pot |

Unless otherwise indicated, the above detergent conditions were used with varing amounts of surfactant ratio by weight. Each result ($\Delta R$), consists of an average of eight measurements (four swatches; front and back). A "bare" prototype formulation containing the minimum amount of ingredients was used to determine the detergency effects of surfactants on various stains and soils. The prototype formulation is as follows:

| Prototype Detergent Formulation Used for The Evaluation Glycacarbamate/Urea Compounds | |
| --- | --- |
| Ingredients (By Weight) | % |
| Total Surfactant System | 22.68 |
| Zeolite 4A | 46.39 |
| Sodium Carbonate | 30.93 |

The surfactant system was dissolved or slurried in about 15 to 25 ml of water according to the appropriate surfactant ratio and then heated to about 60° C. (if necessary). All surfactant systems were added wither as a clear solution or as an opacified mixture.

The following cosurfactants were used in Examples 27–30:

Cosurfactants Used in The
Detergency Evaluation ($\Delta R$) of Glycacarbamate/Urea Compounds $C_8$–$C_{14}$ Alkylbenzene Sulfonate (LAS = Linear Alkylbenzene Sulfonate)
$C_{12}$–$C_{15}$ Alcohol 7 Mole Ethoxylate ($C_{12-15}$ EO7 = Neodol$_{25-7}$)
$C_{12}$ Alcohol 5 Mole Ethoxylate ($C_{12}$ EO5)

Example 27

Detergency Evaluation ($\Delta R$) of Glycacarbamate/Urea Compounds with Linear Alkylbenzene Sulfonate on Lever Clay Cloth
Lever Clay $\Delta R$

| AS/NS (% Ratio by Weight) | T | 100/0 | 95/5 | 90/10 | 75/25 | 50/50 | 25/75 |
| --- | --- | --- | --- | --- | --- | --- | --- |
| LAS/$C_{12}$ maltocarbamate | 40 | 12.1 | 12.5 | 13.0 | 12.8 | 11.6 | 10.7 |

AS/NS = Anionic Surfactant/Nonionic Surfactant
T = Temperature (°C.)

As can be seen from the above table, several mixtures of LAS and ($C_{12}$) N-dodecyl D-maltocarbamate (95/5 to 75/25) which have higher $\Delta R$ values, generally out perform LAS alone (100/0). Based on the above table it can be concluded that glycacarbamate/urea compounds of the present invention effectively remove particulate fatty soil from polyester/cotton cloths.

Detergency Evaluation ($\Delta R$) of Glycacarbamate/Urea Compounds with Linear Alkylbenzene Sulfonate on Vacuum Cleaner Dust Cloth
VCD $\Delta R$

| AS/NS (% Ratio by Weight) | T | 100/0 | 95/5 | 90/10 | 75/25 | 50/50 | 25/75 |
| --- | --- | --- | --- | --- | --- | --- | --- |
| LAS/$C_{12}$ maltocarbamate | 40 | 32.3 | 32.6 | 33.0 | 32.9 | 31.5 | 30.1 |

AS/NS = Anionic Surfactant/Nonionic Surfactant
T = Temperature (°C.)

As can be seen from the above table, several mixtures of LAS and ($C_{12}$) N-dodecyl D-maltocarbamate (95/5 to 75/25) which have higher $\Delta R$ values, generally out perform LAS alone (100/0). Based on the above table it can be concluded that glycacarbamate/urea compounds of the present invention effectively remove particulate fatty soil from polyester/cotton cloths.

Detergency Evaluation ($\Delta R$) of Glycacarbamate/Urea Compounds with Linear Alkylbenzene Sulfonate on WFK 30D Cloth
WFK 30D $\Delta R$

| AS/NS (% Ratio by Weight) | T | 100/0 | 95/5 | 90/10 | 75/25 | 50/50 | 25/75 |
| --- | --- | --- | --- | --- | --- | --- | --- |
| LAS $C_{12}$ maltocarbamate | 40 | 23.0 | 23.4 | 23.8 | 22.9 | 19.8 | 19.0 |

AS/NS = Anionic Surfactant/Nonionic Surfactant
T = Temperature (°C.)

As can be seen from the above table, several mixtures of LAS and ($C_{12}$) N-dodecyl D-maltocarbamate (95/5 to 90/10) which have higher $\Delta R$ values, generally out perform LAS alone (100/0). Based on the above table it can be concluded that glycacarbamate/urea compounds of the present invention effectively remove particulate fatty oily soil from polyester cloths.

Detergency Evaluation ($\Delta R$) of Glycacarbamate/Urea Compounds with Linear Alkylbenzene Sulfonate and Neodol on WFK 30D Cloth
WFK 30D $\Delta R$

| AS/NS (% Ratio by Weight) | T | 100/0/0 | 75/18.7/6.3 | 50/37.5/12.5 | 25/56.4/18.7 |
| --- | --- | --- | --- | --- | --- |
| LAS $C_{12-15}$ EO7 and $C_{12}$ maltocarbamate | 40 | 23.0 | 24.9 | 24.2 | 22.2 |
| LAS $C_{12}$ EO5 and $C_{12}$ maltocarbamate | 40 | 23.0 | 24.4 | 23.6 | 22.3 |

AS/NS = Anionic Surfactant/Nonionic Surfactant
T = Temperature (°C.)

As can be seen from the above table, several mixtures of LAS, $C_{12-15}$ EO7 and $C_{12}$ maltocarbamate (75/18.7/6.3 to 50/37.5/12.5) as well as LAS, $C_{12}$ EO5 and N-dodecyl D-maltocarbamate (75/18.7/6.3) which have higher $\Delta R$ values, generally out perform LAS alone (100/0). Based on the above table it can be concluded that glycacarbamate/urea compounds of the present invention effectively remove particulate, fatty, oily soil from polyester cloths.

Shaving Cream

| Ingredients | % By Weight |
| --- | --- |
| Stearic Acid | 20–40 |
| Coconut Fatty Acid | 6–10 |
| Glycacarbamate, Glycaurea or mixtures thereof | 1–45 |
| Glycerol | 5–15 |
| Potassium Hydroxide | 2–6 |
| Sodium Hydroxide | 1–3 |
| Vegetable or Mineral Oil | 1–5 |
| Water and Optional Ingredients | Balance |

Example 32

Brushless Shaving Cream

| Ingredients | % By Weight |
| --- | --- |
| Glyceryl Monostearate | 10–35 |
| Glycerol | 5–15 |
| Glycacarbamate, Glycaurea or mixtures thereof | 1–45 |
| Mineral Oil | 1–5 |
| Water and Optional Ingredients | Balance |

Example 33

Brushless Shaving Cream

| Ingredients | % By Weight |
| --- | --- |
| Cellulose Alkyl Ether | 70–75 |
| Glycerol | 5–15 |
| Glycacarbamate, Glycaurea or mixtures thereof | 1–5 |
| Mineral Oil | 1–5 |
| Water and Optional Ingredients | Balance |

Example 34

Shower Gel

| Ingredients | % By Weight |
| --- | --- |
| Sodium Coconut Isethionate | 5–10 |
| Sodium Ether Lauryl Sulfate | 2–5 |
| Glycacarbamate, Glycaurea or mixtures thereof | 1–45 |
| Coconutamidopropyl Betaine | 8–15 |
| Ethyleneglycol Distearate | 4–10 |
| Isopropyl Palmitate | 0.5–1 |
| Moisturizer | 0.2–1 |
| Preservative | 0.05–0.1 |
| Sodium Chloride | 1–5 |
| Water and Optional Ingredients | Balance |

Example 35

Toilet Soap Bar

| Ingredients | % By Weight |
| --- | --- |
| Coconut Fatty Acid | 5–60 |
| Sodium Coconut Isethionate | 0–50 |
| Alkyl Sulfate | 0–5 |
| Glycacarbamate, Glycaurea or mixtures thereof | 1–45 |
| Water Soluble Polymer (Polyacrylate) | 0–10 |
| Moisturizer (Sorbitol or Glycerin) | 0.1–10 |

-continued

Toilet Soap Bar

| Ingredients | % By Weight |
| --- | --- |
| Sequestrant (Sodium Citrate) | 0.1–.5 |
| Dye | <0.1 |
| Brightener | <0.1 |
| Whitener | 0.1–0.4 |
| Fragrance | 0.1–2 |
| Water and Optional Ingredients | Balance |

Example 36

Shampoo

| Ingredients | % By Weight |
| --- | --- |
| Sodium Lauryl Sulfate | 0–13 |
| Glycacarbamate, Glycaurea or mixtures thereof | 1–17 |
| Cocoamidobetaine | 0–7 |
| Lauramide MEA | 0–5 |
| Moisturizer (Sorbitol or Glycerin) | 0.1–10 |
| Fragrance | 0.1–2 |
| Preservative | 0–1 |
| Water | Balance |

Example 37

Liquid Detergent

| Ingredients | % By Weight |
| --- | --- |
| Alkylbenzene Sulfonate | 1–70 |
| Glycacarbamate, Glycaurea or mixtures thereof | 0.5–50 |
| Builder | 0–50 |
| Electrolyte | 0–40 |
| Enzyme | 0.01–5 |
| Enzyme Stabilizer | 0.1–15 |
| Phase Regulant | 0–20 |
| Fragrance | 0–2 |
| Preservative | 0–1 |
| Water and Optional Ingredients | Balance |

Example 38

Powdered Detergent

| Ingredients | % By Weight |
| --- | --- |
| Alkylbenzene Sulfonate | 1–55 |
| Glycacarbamate, Glycaurea or mixtures thereof | 0.5–50 |
| Builder | 0–55 |
| Buffer | 0–30 |
| Salt | 0–30 |
| Enzyme | 0–4 |
| Enzyme Stabilizer | 0.1–15 |
| Bleach System | 0–37 |
| Fragrance | 0–2 |
| Preservative | 0–1 |
| Water and Optional Ingredients | Balance |

| Hand/Facial/Body Cleanser | |
|---|---|
| Ingredients | % By Weight |
| Sodium Lauryl Sulfate Glycacarbamate or Glycaurea | 0.5–50 |
| Builder | 0–55 |
| Buffer | 0–30 |
| Salt | 0–30 |
| Enzyme | 0–4 |
| Enzyme Stabilizer | 0.1–15 |
| Bleach System | 0–37 |
| Fragrance | 0–2 |
| Preservative | 0–1 |
| Water and Optional Ingredients | Balance |

This invention has been described with respect to certain preferred embodiments and various modifications and variations in light thereof will be suggest to persons skilled in the art and are to be included within the spirit and purview of this application and the scope of the appended claims.

What is claimed is:

1. A personal product composition comprising:

(1) a compound selected from the group consisting of cyclic glycacarbamate, glycaurea, and mixtures thereof; and (2) a surfactant selected from the group consisting of soaps, anionic surfactants, nonionic surfactants, amphoteric surfactants, zwitterionic surfactants, cationic surfactants, and mixtures thereof;

wherein said cyclic glycacarbamate has the formula:

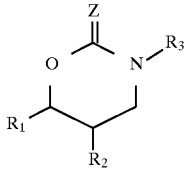

and said glycaurea has the formula:

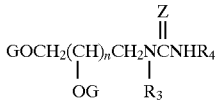

wherein:
   $R_1$ is $GOCH_2(CHOG)_n$—;
   $R_2$ is GO—;
   Z is oxygen (O);
   G is hydrogen, $SO_3M$, $PO_3M_2$, monosaccharide, $(CH_2CH_2O)_q$—H, $(CH_2CHCH_3O)_r$—H group or mixtures thereof;
   M is hydrogen, an alkali metal, alkaline earth metal, ammonium, substituted alkyl ammonium group, or mono-, di-, trialkanolammonium group comprising 1 to 3 carbon atoms,
   n is an interger from 0 to 5;
   q and r are intergers from 1 to 30;
   $R_3$ is selected from the group consisting of;

$R_4$ is hydrogen;
   $R_5$ is hydrogen, a straight or branched chain, saturated or unsaturated hydrocarbon radical comprising from 2 to 28 carbon atoms;
   X is hydrogen, a saturated hydrocarbon radical comprising 1 to 3 carbon atoms or mixtures thereof;
   W is an amine (NA), amine salt (NHA+M–), ether (O), hydroxyl (CHOH or HOCOH) or mixtures thereof;
   m is an interger from 1 to 5;
   p is an interger from 0 to 30;
   A is a straight or branched chain, saturated or unsaturated hydrocarbon radical comprising from 1 to 28 carbon atoms.

2. A personal product composition according to claim 1, wherein the composition is a toilet bar soap composition.

3. A personal product composition according to claim 1, wherein the composition is a hand/facial/body cleanser composition.

4. A personal product composition according to claim 1, wherein the composition is a shampoo composition.

5. A personal product composition according to claim 1, wherein the composition is a conditioner composition.

6. A personal product composition according to claim 1, wherein the composition is a oral hygiene composition.

7. A personal product composition according to claim 1, wherein the composition is a deodorant composition.

8. A personal product composition according to claim 1, wherein the composition is a shaving cream or shaving lotion composition.

9. A personal product composition according to claim 1, wherein the composition is a shower gel composition.

10. A personal product composition according to claim 1, wherein the composition is a cosmetic composition.

11. A personal product composition according to claim 1, wherein the composition is a bath composition.

12. A personal product composition according to claim 1, wherein the composition is a skin care composition.

13. A detergent composition comprising:

(1) a compound selected from the group consisting of cyclic glycacarbamate, glycaurea, and mixture thereof; and (2) a surfactant selected from the group consisting of soaps, anionic surfactants, nonionic surfactants, amphoteric surfactants, zwifterionic surfactants, catoionic surfactants, and mixtures thereof;

wherein said cyclic glycacarbamate has the formula:

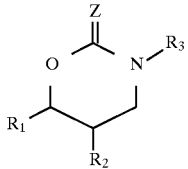

an said glycaurea has the formula:

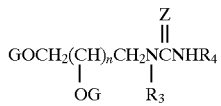

wherein:
R$_1$ is GOCH$_2$(CHOG)$_n$—;
R$_2$ is GO—;
Z is oxygen (O);
G is hydrogen, SO$_3$M, PO$_3$M$_2$, monosaccharide, (CH$_2$CH$_2$O)$_q$—H, (CH$_2$CHCH$_3$O)$_r$—H group or mixtures thereof;
M is hydrogen, an alkali metal, alkaline earth metal, ammonium, substituted alkyl ammonium group, or mono-, di-, trialkanciammonium group comprising 1 to 3 carbon atoms,
n is an interger from 0 to 5;
q and r are intergers from 1 to 30;
R$_3$ is selected from the group consisting of;

R$_4$ is hydrogen;

R$_5$ is hydrogen, a straight or branched chain, saturated or unsaturated hydrocarbon radical comprising from 2 to 28 carbon atoms;
X is hydrogen, a saturated hytdrocarbon radical comprising 1 to 3 carbon atoms or mixtures thereof;
W is an amine (NA), amine salt (NHA+M−), ether (O), hydroxyl (CHOH or HOCOH) or mixtures thereof,
m is an interger from 1 to 5;
p is an interger from 0 to 30;
A is a straight or branched chain, saturated or unsaturated hydrocarbon radical comprising from 1 to 28 carbon atoms.

14. A detergent composition according to claim 13, wherein the composition is a liquid detergent composition.

15. A detergent composition according to claim 13, wherein the composition is a powdered or granular composition.

16. A detergent composition according to claim 13, wherein the composition is a light-duty manual dishwashing composition.

17. A detergent composition according to claim 13, wherein the composition is automatic dishwashing composition.

18. A detergent composition according to claim 13, wherein the composition is a softening rinse composition.

* * * * *